US006830828B2

(12) United States Patent
Thompson et al.

(10) Patent No.: US 6,830,828 B2
(45) Date of Patent: Dec. 14, 2004

(54) ORGANOMETALLIC COMPLEXES AS PHOSPHORESCENT EMITTERS IN ORGANIC LEDS

(75) Inventors: Mark E. Thompson, Anaheim, CA (US); Peter Djurovich, Long Beach, CA (US); Sergey Lamansky, Camarillo, CA (US); Stephen R. Forrest, Princeton, NJ (US); Marc A. Baldo, Princeton, NJ (US); Paul E. Burrows, Kennewick, WA (US)

(73) Assignees: The Trustees of Princeton University, Princeton, NJ (US); The University of Southern California, Los Angeles, CA (US)

( * ) Notice: Subject to any disclaimer, the term of this patent is extended or adjusted under 35 U.S.C. 154(b) by 0 days.

(21) Appl. No.: 09/883,734

(22) Filed: Jun. 18, 2001

(65) Prior Publication Data

US 2002/0034656 A1 Mar. 21, 2002

Related U.S. Application Data

(63) Continuation-in-part of application No. 09/274,609, filed on Mar. 23, 1999, now abandoned, and a continuation-in-part of application No. 09/452,346, filed on Dec. 1, 1999, now abandoned, and a division of application No. 09/311,126, filed on May 13, 1999, now abandoned.

(51) Int. Cl.[7] .............................................. H05B 33/14
(52) U.S. Cl. ....................... 428/690; 428/917; 313/504; 313/506; 257/102; 257/103
(58) Field of Search ................................ 428/690, 917; 313/504, 506; 252/301.16; 257/102, 103

(56) References Cited

U.S. PATENT DOCUMENTS

| 4,455,506 A | 6/1984 | Ayyagari et al. ............ 313/506 |
| 4,539,507 A | 9/1985 | VanSlyke et al. ........... 313/504 |
| 4,758,765 A | 7/1988 | Mitsumori ................... 313/506 |
| 4,769,292 A | 9/1988 | Tang et al. .................. 428/690 |
| 4,950,950 A | 8/1990 | Perry et al. .................. 313/504 |
| 5,128,587 A | 7/1992 | Skotheim et al. ........... 313/504 |
| 5,203,974 A | 4/1993 | Kokado et al. |
| 5,231,329 A | 7/1993 | Nishikitani et al. ......... 313/503 |
| 5,247,190 A | 9/1993 | Friend et al. ................. 257/40 |
| 5,294,810 A | 3/1994 | Egusa et al. .................. 257/40 |
| 5,294,870 A | 3/1994 | Tang et al. .................. 313/504 |
| 5,439,794 A | 8/1995 | Barton |
| 5,457,565 A | 10/1995 | Namiki et al. ............... 359/273 |
| 5,504,183 A | 4/1996 | Shi et al. ..................... 528/272 |
| 5,540,999 A | 7/1996 | Yamamoto et al. ....... 428/411.1 |
| 5,554,220 A | 9/1996 | Forrest et al. |
| 5,601,903 A | 2/1997 | Fujii et al. ................... 428/212 |
| 5,663,573 A | 9/1997 | Epstein et al. ................ 257/40 |
| 5,674,597 A | 10/1997 | Fuji et al. .................... 428/212 |
| 5,698,048 A | 12/1997 | Friend et al. ................ 136/263 |
| 5,703,436 A | 12/1997 | Forrest et al. ............... 313/506 |
| 5,707,745 A | 1/1998 | Forrest et al. ............... 428/432 |
| 5,756,224 A | 5/1998 | Börner et al. ................ 428/690 |
| 5,757,026 A | 5/1998 | Forrest et al. ................ 257/40 |
| 5,757,139 A | 5/1998 | Forrest et al. ............ 315/169.3 |
| 5,811,833 A | 9/1998 | Thompson .................... 257/40 |
| 5,811,834 A | 9/1998 | Tamano et al. ............... 257/40 |
| 5,834,130 A | 11/1998 | Kido et al. .................. 428/690 |

(List continued on next page.)

FOREIGN PATENT DOCUMENTS

| EP | 0 704 915 | 4/1996 |
| JP | 3-289090 | 12/1991 |
| WO | 96/19792 | 6/1996 |
| WO | 97/33296 | 9/1997 |
| WO | 97/48115 | 12/1997 |
| WO | 97/48139 | 12/1997 |
| WO | 98/50989 | 11/1998 |
| WO | WO 98/58037 | 12/1998 |
| WO | 02/02714 | 1/2002 |
| WO | 02/15645 | 2/2002 |

OTHER PUBLICATIONS

B.N. Cockburn, et al., "Reactivity of Co–ordinated Ligands. Part XV. Formation of Complexes containing Group V Donor Atoms and Metal–Carbon –bonds", Journal of the Chemical Society, Dalton Transactions, vol. 4 (1973), pp. 404–410. (no month).

J.K. Lee, et al., "Thin film light emitting devices from an electroluminescent ruthenium complex", Appl. Phys. Lett., 69 (12), pp. 1686–1688, Sep. 16, 1996.

D. Yoo, et al., "New Electro–Active Self–Assembled Multilayer Thin Films Based on Alternately Adsorbed Layers of Polyelectrolytes and Functional Dye Molecules", Synthetic Metals, 85, pp. 1425–1426, 1997. (no month).

J–K. Lee et al., "Thin Film Light Emitting Heterostructures: From Conjugated Polymers to Ruthenium Complexes to Inorganic Nanocrystallites," Abstracts of Papers, Part 2, 213th ACS National Meeting, American Chemical Society, San Francisco, CA, Apr. 13–17, 1997, No. 200.

(List continued on next page.)

Primary Examiner—Marie Yamnitzky
(74) Attorney, Agent, or Firm—Kenyon & Kenyon

(57) ABSTRACT

Organic light emitting devices are described wherein the emissive layer comprises a host material containing an emissive molecule, which molecule is adapted to luminesce when a voltage is applied across the heterostructure, and the emissive molecule is selected from the group of phosphorescent organometallic complexes, including cyclometallated platinum, iridium and osmium complexes. The organic light emitting devices optionally contain an exciton blocking layer. Furthermore, improved electroluminescent efficiency in organic light emitting devices is obtained with an emitter layer comprising organometallic complexes of transition metals of formula $L_2MX$, wherein L and X are distinct bidentate ligands. Compounds of this formula can be synthesized more facilely than in previous approaches and synthetic options allow insertion of fluorescent molecules into a phosphorescent complex, ligands to fine tune the color of emission, and ligands to trap carriers.

29 Claims, 51 Drawing Sheets

U.S. PATENT DOCUMENTS

| | | | | |
|---|---|---|---|---|
| 5,834,893 | A | 11/1998 | Bulovic et al. | 313/506 |
| 5,840,897 | A | 11/1998 | Kirlin et al. | |
| 5,844,363 | A | 12/1998 | Gu et al. | 313/506 |
| 5,861,219 | A | 1/1999 | Thompson et al. | 428/690 |
| 5,874,803 | A | 2/1999 | Garbuzov et al. | 313/506 |
| 5,917,280 | A | 6/1999 | Burrows et al. | 313/506 |
| 5,932,895 | A | 8/1999 | Shen et al. | 257/89 |
| 5,953,587 | A | 9/1999 | Forrest et al. | 438/99 |
| 5,981,306 | A | 11/1999 | Burrows et al. | 438/22 |
| 5,986,268 | A | 11/1999 | Forrest et al. | 250/372 |
| 5,986,401 | A | 11/1999 | Thompson et al. | 313/504 |
| 5,989,738 | A | 11/1999 | Haase et al. | 428/690 |
| 5,998,803 | A | 12/1999 | Forrest et al. | 257/40 |
| 6,013,429 | A | 1/2000 | Franke et al. | 430/551 |
| 6,013,538 | A | 1/2000 | Burrows et al. | 438/22 |
| 6,013,982 | A | 1/2000 | Thompson et al. | 313/506 |
| 6,030,715 | A | 2/2000 | Thompson et al. | 428/690 |
| 6,045,930 | A | 4/2000 | Thompson et al. | 428/690 |
| 6,046,543 | A | 4/2000 | Bulovic et al. | 313/504 |
| 6,048,630 | A | 4/2000 | Burrows et al. | 428/690 |
| 6,083,634 | A | 7/2000 | Shi | 428/690 |
| 6,091,195 | A | 7/2000 | Forrest et al. | 313/504 |
| 6,091,382 | A | 7/2000 | Shioya et al. | 345/76 |
| 6,097,147 | A | 8/2000 | Baldo et al. | 313/506 |
| 6,111,902 | A | 8/2000 | Kozlov et al. | 372/39 |
| 6,125,226 | A | 9/2000 | Forrest et al. | 385/131 |
| 6,160,828 | A | 12/2000 | Kozlov et al. | 372/39 |
| 6,242,115 | B1 | 6/2001 | Thompson et al. | 428/690 |
| 6,303,238 | B1 | 10/2001 | Thompson et al. | 428/690 |
| 6,337,102 | B1 | 1/2002 | Forrest et al. | 427/64 |
| 6,358,631 | B1 | 3/2002 | Forrest et al. | 428/690 |
| 6,524,727 | B1 | 2/2003 | Kathirgamanathan | 428/690 |

OTHER PUBLICATIONS

J. Lee, et al., "Synthesis and Characterization of an Electroluminescent Polyester Containing the Ru(II) Complex", Chem. Mater., 1997, vol. 9, No. 8, pp. 1710–1712. (no month).

H. Gilman, et al., J. Am. Chem. Soc., 71, 1870–1871 (May 1949).

M.A. Baldo, et al., "Very high efficiency green organic light–emitting device based on electrophosphorescence", Applied Physics Letters, vol. 75, No. 1, pp. 4–6, (Jul. 1999).

D.F. O'Brien, et al., "Improved energy transfer in electrophosphorescent devices", Applied Physics Letters, vol. 74, No. 3, pp. 442–444, (Jan. 18, 1999).

M.A. Baldo, et al., "Highly efficient phosphorescent emission from organic electroluminescent devices", Nature, vol. 395, pp. 151–154, (Sep. 1998).

G.R. Newkome, et al., 86 Chem. Rev., 451–489 (1986). (no month).

A.D. Ryabov, 90 Chem. Rev., 403–424 (1990). (no month).

M. Maestri, et al., Adv. Photochem., vol. 17, pp. 1–68 (1992). (no month).

L. Chassot, et al., 66 Helv. Chim. Acta., 2443–2444 (1983). (no month).

L. Chassot, et al., 23 Inorg. Chem., 4249–4253 (Dec. 1984).

S. Bonafede, et al., 90 J. Phys. Chem., 3836–3841 (Jul. 1986).

L. Chassot, et al., 108, J. Am. Chem. Soc., 6084–6085 (1986). (no month).

Ch. Cornioley–Deuschel, et al., 26 Inorg. Chem., 3354–3358 (Oct. 1987).

L. Chassot, et al., 26 Inorg. Chem., 2814–2818 (Aug. 1987).

A. von Zelewsky, et al., 32 Inorg. Chem., 4585–4593 (Oct. 1993).

A. von Zelewsky, et al., 132 Coord. Chem. Rev., 75–85 (1994). (no month).

P. Jolliet, et al., 35 Inorg. Chem., 4883–4888 (Aug. 1996).

H. Wiedenhofer, et al., 99 J. Phys. Chem., 13385–13391 (1995),.(no month).

M. Gianini, et al., 36 Inorg. Chem., 6094–6098 (1997). (no month).

M. Maestri, et al., 122 Chem. Phys. Lett., 375–379 (Dec. 1985).

M. Maestri, et al., 71 Helv. Chim. Acta., 1053–1059 (1988). (no month).

T. Kaufmann, et al. 116 Chem. Ber., 992–1000 (1983). (no month).

D.H. Hey, et al., J. Chem. Soc., 3963–3969 (1955). (no month).

R.A. Abramovitch, et al., J. Chem. Soc., 2175–2187 (1964). (no month).

J.C.W. Evans, et al., 2 Org. Synth. 517–519 (1943). (no month).

R. E. Moore, et al., 23 J. Org. Chem., 1504–1506 (Oct. 1958).

A. Uehara, et al., 239 J. Organomet. Chem., 1–10 (1982). (no month).

H. Takaya, et al., 67 Org. Synth., 20–33 (1989). (no month).

G.B. Kauffman, et al., 6 Inorg. Synth., 211–215 (1957), (no month).

A. Shoustikov, et al., 91 Synth. Met., 217–221 (1997). (no month).

C. W. Tang, et al., "Organic Electroluminescent Diodes", 51 Appl. Phys. Lett., 913–915 (Sep. 1987).

S. R. Forrest, et al., "Organic Emitters Promise a New Generation of Displays", Laser Focus World, (Feb. 1995).

H.J.A. Dartnall, et al., 220 Proc. Roy. Soc. B (London), 115–130 (1983). (no month).

Kido, J., et al., Applied Physics Letters, 73, 2721–2723 (Nov. 1998).

I.G. Hill, et al., "Combined photoemission/in vacuo transport study of the indium tin oxide/copper phthalocyanine/ N,N'–diphenyl–N,N' –bis (I–naphthyl)–1,1' biphenyl–4,4" diamine molecular organic semiconductor system", Journal of Applied Physics, vol. 86, No. 4, 2116–2122, (Aug. 1999).

K. A. King, et al., "Excited–State Properties of a Triply Ortho–Metalated Iridium (III) Complex", J. Am. Chem. Soc., (1985), 107, 1431–1432. (no month).

L. S. Hung, "Enhanced electron injection in organic electroluminescence devices using an Al/LiF electrode", Appl. Phys. Lett., 70(2), 152–154, (Jan. 1997).

G. Gu, et al., "High–external–quantum–efficiency organic light–emitting devices", Optics Letters, vol. 22, No. 6, 396–398, (Mar. 1997).

Hoshino et al., "Electroluminescence from triplet excited states of benzophenone", Appl. Phys. Lett. 69(2), 224–226, (Jul. 1996).

C.H. Chen, et al., "Recent developments in molecular organic electroluminescent materials", Macromolecular Symposia, 125, 1–48 (1997). (no month).

C. W. Tang, et al., "Electroluminescence of doped organic films," 65 J. Appl. Phys., 3610–3616, (May 1989).

V. Bulovic, et al., "Bright, saturated, red–to–yellow organic light–emitting devices based on polarization–induced spectral shifts," Chem. Phys. Lett., 287, 455–460 (1998). (no month).

M. A. Baldo et al., "Excitonic singlet–triplet ration in a semiconducting organic thin film", *Physical Review B*, pp. 14422–14428 (Nov. 15, 1999).

M. A. Baldo, et al., "High–Efficiency fluorescent organic light–emitting devices using a phosphorescent sensitizer", *Nature*, vol. 403, pp. 750–753, Feb. 17, 2000.

C. Adachi, et al., "Electroluminescence mechanisms in organic light emitting devices employing a europium chelate doped in a wide energy gap bipolar conducting host", *J. Appl. Phys.*, vol. 87, No. 11, pp. 8049–8055, Jun. 1, 2000.

Y. Kunugi, et al., "A Vapochromic LED", *J. Am. Chem. Soc.*, vol. 120, No. 3, pp. 589–590, 1998. (published on Web Jan. 7, 1998).

J. Kido, et al., "Electroluminsecence in a Terbium Complex", Chemistry Letters, 1990, pp. 657–660, (no month).

J. Kido, et al., "Organic electroluminescence devices using lanthanide complexes", J. Alloys and Compounds, 1993, 192, pp. 30–33, (no month).

J. Kido, et al., "Bright red light–emitting organic electroluminescent devices having a europium as an emitter", Appl Phys. Lett., Oct. 1994, 65, pp. 2124–2126.

J. Kido, et la., "White–Light–Emitting Organic Electroluminescent Device Using Lanthanide Complexes," Jpn. J. Appl. Phys., 35, pp. L394–L396, Mar. 1996.

S. R. Forrest, "Ultrathin Organic Films Grown by Organic Molecular Beam Deposition and Related Techniques," Chemical Reviews, Sep./Oct. 1997, vol. 97, No. 6, pp. 1793–1896.

Butovic et al., "Tranparent Light–emitting Devices", Nature 380, 29 (Mar. 1996).

Whitlock et al., "Investigation of Materials and Devices Structures for Organic Semiconductor Solar Cells", Optical Eng., vol. 32, No. 8, 1921–1934 (Aug. 1993).

Adachi et al., Jpn. J. Appl. Phys, 27:L269–L271, Feb. 1988.

Dirr, S. et al., "Vacuum–deposited thin films oflanthanide complexes: spectral properties and applications in OLEDs", SID 97 Digest, pp. 778–781, Soc. for Information Display, Santa Ana, CA, May, 1997.

T. Tsutsui et al., "Electroluminescence in Organic Thin Films", *Photochemical Processes in Organized Molecular Systems*, edited by K. Honda, North Holland, Amsterdam, 1991, pp. 437–450, (no month).

M. Morikawa et al., "Electrostatic Luminous Cells with the Emitter Layer of Phosphosrescent Dyes", Extended Abstracts, The 51$^{st}$ Autumn Meeting of the Japan Society of Applied Physics, 1990, p. 1041, Article 28a–PB–8.* (no month).

A. Shoustikov, et al.,"Electroluminescence Color Tuning by Dye Doping Organic Light Emitting Diodes," *IEEE Journal of Special Topics in Quantum Electronics*, 4, 3–14, (Jan. / Feb. 1998).

C. H. Chen, et al., "Improved red dopants for organic luminescent devices," *Macromolecules Symposia*, 125, 49–58, (1997), (no month).

V. Bulovic, et al., "Tuning the color emission of thin film molecular organic light emitting devices by the solid state solvation effect," *Chemical Physics Letters*, (Jul. 23, 1999), 317–322.

Gary L. Miessler, et al., *Inorganic Chemistry*, 2nd Edition, Prentice–Hall, pp. 1–3, 422–424, 442 (early 1999 version).

Gary L. Miessler, et al., *Inorganic Chemistry*, 2nd Edition, Prentice–Hall, pp. 1–3, 422–424, 442 (Aug. 1999 version).

Baldo, et al., Nature, vol. 43, pp. 750–753, Feb. 17, 2000.

Tsutsui, et al., "High Quantum Efficiency in Organic Light–Emitting Devices with Iridium–Complex as a Triplet Emissive Center", Jpn. J. Appl. Phys., vol. 38 (1999), pp. L 1502–L 1504.

Lee et al., "Polymer phosphorescent light–emitting devices doped with tris (2–phenylpyridine) iridium as a triplet emitter", Appl. Phys. Lett., vol. 77, No. 15, pp. 2280–2282, Oct. 9, 2000.

C. Tang, *SPIE's OE Magazine*, pp. 18–21, Feb. 2001.

Cleave et al., "Harvesting Singlet and Triplet Energy in Polymer LEDs", Adv. Mater., 1999, 11, No. 4, pp. 285–288. (no month).

Friend, et al., "Electroluminescence in conjugated polymers", Nature, vol. 397, pp. 121–128, Jan. 14, 1999.

P.F. Schewe et al, "Electrophosphorescence gets the green light", Physics News Update No. 437, Story #2, The American Institute of Physics Bulletin of Physics News, Jul. 2, 1999.

Y. Ma, et al., "High Luminescence Gold (I) and Copper (I) Complexes with a Triplet Excited State for Use in Light–Emitting Diodes", Advanced Materials 1999, 11, No. 10, pp. 852–857. no month.

S. W. Depp and W. E. Howard, "Flat Panel Displays," *Scientific American* (Mar. 1993), pp. 90–97.

D. Z. Garbuzov et al., "Photoluminescence Efficiency and Absorption of Aluminum Tris–Quinolate ($Alq_3$) Thin Films," 249 *Chemical Physics Letters* 433–437 (Feb. 1996).

C. E. Johnson et al., "Luminescent Iridium (I), Rhodium (I), and Platinum (II) Dithiolate Complexes," 105 *Journal of the American Chemical Society* 1795–1802 (1983). no month.

Hosokawa et al., "Highly efficient blue electroluminescence from a distyrylarylene emitting layer with a new dopant," 67 *Appl. Phys. Lett.* 3853–3855 (Dec. 1995).

Adachi et al., "Blue light–emitting organic electroluminescent devices," 56 *Appl. Phys. Lett.* 799–801 (Feb. 1990).

C. C. Wu et al., "Integrated three–color organic light–emitting devices," 69 *Appl. Phys. Lett.* 3117–3119 (Nov. 1996).

H. Vestweber et al., "Electroluminescense from polymer blends and molecularly doped polymers," 64 *Synthetic Metals* 141–145 (1994). no month.

Burrows et al., "Color Tunable Organic Light Emitting Devices," 69 *Appl. Phys. Lett.* 2959 (Nov. 11, 1996).

D. Z. Garbuzov et al., "Organic films deposited on Si p–n junctions: Accurate measurements of fluorescence internal efficiency, and application to luminescent antireflection coatings," 80 *J. Appl. Phys.* 4644–4648 (Oct. 1996).

P.E. Burrows et al., "Reliability and degradation of organic light emitting devices," 65 *Appl. Phys. Lett.* 2922–2924 (Dec. 1994).

H. A. MacLeod, *Thin Film Optical Filters*, pp. 94–110 (1969). no month.

Johnson et al., "Electroluminescence from Single Layer Molecularly doped polymer films," 67 *Pure & Appl. Chem.*, 175–182 (1995). no month.

G. Calogero, et al., "Absorption spectra, luminescence properties, and electrochemical behavior of cyclometalated Iridium (III) and Rhodium (III) complexes with a Bis(pyridyl) triazole ligand", Inorg. Chem. 1995, 34, pp. 541–545. no month.

G. Di Marco, et al., "Luminescent mononuclear and dinuclear Iridium (III) cyclometalated complexes immobilized in a polymeric matrix as solid–state oxygen sensors", Anal. Chem. Dec. 1998, 70, pp. 5019–5023.

C. Berg–Brennan, et al., "Luminescent ruthenium polypyridyl complexes containing pendant pyridinium acceptors", Inorg. Chem. 1996, 35, pp. 3719–3722. no month.

H. Zollinger, *Color Chemistry, Syntheses, Properties and Applications of Organic Dyes and Pigments*, Second, revised edition, VCH Publishers, (1991). no month.

I. Omae, *Organometallic Intramolecular–coordination compounds*, Elsevier Publishing Company Inc., N.Y. (1986). no month.

Lamansky et al., *Optical Properties of Pt (II) Cyclometalated Complexes in Polymer Matrices, Preparation and Potential Uses in OLEDs, Abstracts of Papers*, Part 1, 217th ACS National Meeting, Anaheim, CA (Mar. 21–25, 1999). Chemistry.ORG, The Website of the American Chemical Society, Internet Schedule of 217th ACS National Meeting, (Mar. 21–25, 1999); printed on Jul. 22, 2003.

Y. Ma, et al. "Electroluminescence from triplet metal–ligand charge–transfer excited state of transition metal complexes", Synthetic Metals 94 (1998), pp. 245–248. (no month).

H. F. Wittmann, et al., "Optical spectroscopy of platinum and palladium containing poly–ynes", J. Chem. Phys., vol. 101, No. 4, pp. 2693–2698, Aug. 15, 1994.

M.A. Baldo, et al., "Phosphorescent materials for application to organic light emitting devices", Pure Appl. Chem., vol. 71, No. 11, pp. 2095–2106, 1999. (no month).

G. DiMarco, et al., "A Luminescent Iridium(III) Cyclometallated Complex Immobilized in a Polymeric Matrix as a Solid–State Oxygen Sensor", Advanced Materials, vol. 8, pp. 576–580, Jul. 1996.

J.N. Demas, et al., "Design and Applications of Highly Luminescent Transition Metal Complexes", Analytical Chemistry, vol. 63, No. 17, pp. 829–837, Sep. 1, 1991.

K. Vinodgopal, et al., "Photochemistry of Ru(bpy)2(dcbpy)2+ on Al2O3 and TiO2 Surfaces. An Insight into the Mechanism of Photosensitization", J. Phys. Chem. 1995, 99, pp. 10883–10889. (no month).

R. Holmlin et al., "Os(phen)2dppz2+ in Photoinduced DNA–Mediated Electron Transfer Reactions", J. Am. Chem. Soc. 1996, 118, pp. 5236–5244. (no month).

Electronic absorbance spectra of Pt(thpy)$_2$, Pt(thq)$_2$, Pt(bph)(bpy).

Emission spectra of the complexes.

Energy transfer from PVK to Pt(thpy)$_2$ in the solid film.

—□— PVK
—○— PVK:Pt 100:1.7
—△— PVK:Pt 100:3.9
—✕— PVK:Pt 100:6.3
—▽— PVK:Pt 100:9.8

I-V characteristic of the device.

Quantum efficiency of the device as a function of applied voltage.

other L ligands phenylimines     vinylpyridines     arylquinolines     pyridylnapthalenes pyridylpyroles     pyridylimidazoles     phenylindoles other X ligands aminoacids     salicylaldehydes     iminoacetonates

LL'L"M

M(ppy)(bq)(thpy)

LL'MX

M(ppy)(bq)(acac)

M(ppy)(thpy)(acac)

LMXX'

M(ppy)(sd)(acac)

ORGANOMETALLIC COMPLEXES AS PHOSPHORESCENT EMITTERS IN ORGANIC LEDS

This is a continuation-in-part of application Ser. No. 09/274,609, filed Mar. 23, 1999, now abandoned; application Ser. No. 09/452,346, filed Dec. 1, 1999, now abandoned; and application Ser. No. 09/311,126, filed May 13, 1999, now abandoned.

GOVERNMENT RIGHTS

This invention was made with Government support under Contract No. F33615-94-1-1414 awarded by DARPA. The government has certain rights in this invention.

FIELD OF INVENTION

The present invention is directed to organic light emitting devices (OLEDs) comprised of emissive layers that contain an organometallic phosphorescent compound.

BACKGROUND OF THE INVENTION

Organic light emitting devices (OLEDs) are comprised of several organic layers in which one of the layers is comprised of an organic material that can be made to electroluminesce by applying a voltage across the device, C. W. Tang et al., Appl. Phys. Lett. 1987, 51, 913. Certain OLEDs have been shown to have sufficient brightness, range of color and operating lifetimes for use as a practical alternative technology to LCD-based full color flat-panel displays (S. R. Forrest, P. E. Burrows and M. E. Thompson, Laser Focus World, Feb. 1995). Since many of the thin organic films used in such devices are transparent in the visible spectral region, they allow for the realization of a completely new type of display pixel in which red (R), green (G), and blue (B) emitting OLEDs are placed in a vertically stacked geometry to provide a simple fabrication process, a small R-G-B pixel size, and a large fill factor, International Patent Application No. PCT/US95/15790.

A transparent OLED (TOLED), which represents a significant step toward realizing high resolution, independently addressable stacked R-G-B pixels, was reported in International Patent Application Ser. No. PCT/US97/02681 in which the TOLED had greater than 71% transparency when turned off and emitted light from both top and bottom device surfaces with high efficiency (approaching 1% quantum efficiency) when the device was turned on. The TOLED used transparent indium tin oxide (ITO) as the hole-injecting electrode and a Mg—Ag—ITO electrode layer for electron-injection. A device was disclosed in which the ITO side of the Mg—Ag—ITO electrode layer was used as a hole-injecting contact for a second, different color-emitting OLED stacked on top of the TOLED. Each layer in the stacked OLED (SOLED) was independently addressable and emitted its own characteristic color. This colored emission could be transmitted through the adjacently stacked, transparent, independently addressable, organic layer or layers, the transparent contacts and the glass substrate, thus allowing the device to emit any color that could be produced by varying the relative output of the red and blue color-emitting layers.

The PCT/US95/15790 application disclosed an integrated SOLED for which both intensity and color could be independently varied and controlled with external power supplies in a color tunable display device. The PCT/US95/15790 application, thus, illustrates a principle for achieving integrated, full color pixels that provide high image resolution, which is made possible by the compact pixel size. Furthermore, relatively low cost fabrication techniques, as compared with prior art methods, may be utilized for making such devices.

Because light is generated in organic materials from the decay of molecular excited states or excitons, understanding their properties and interactions is crucial to the design of efficient light emitting devices currently of significant interest due to their potential uses in displays, lasers, and other illumination applications. For example, if the symmetry of an exciton is different from that of the ground state, then the radiative relaxation of the exciton is disallowed and luminescence will be slow and inefficient. Because the ground state is usually anti-symmetric under exchange of spins of electrons comprising the exciton, the decay of a symmetric exciton breaks symmetry. Such excitons are known as triplets, the term reflecting the degeneracy of the state. For every three triplet excitons that are formed by electrical excitation in an OLED, only one symmetric state (or singlet) exciton is created. (M. A. Baldo, D. F. O'Brien, M. E. Thompson and S. R. Forrest, Very high-efficiency green organic light-emitting devices based on electrophosphorescence, Applied Physics Letters, 1999, 75, 4–6.) Luminescence from a symmetry-disallowed process is known as phosphorescence. Characteristically, phosphorescence may persist for up to several seconds after excitation due to the low probability of the transition. In contrast, fluorescence originates in the rapid decay of a singlet exciton. Since this process occurs between states of like symmetry, it may be very efficient.

Many organic materials exhibit fluorescence from singlet excitons. However, only a very few have been identified which are also capable of efficient room temperature phosphorescence from triplets. Thus, in most fluorescent dyes, the energy contained in the triplet states is wasted. However, if the triplet excited state is perturbed, for example, through spin-orbit coupling (typically introduced by the presence of a heavy metal atom), then efficient phosphoresence is more likely. In this case, the triplet exciton assumes some singlet character and it has a higher probability of radiative decay to the ground state. Indeed, phosphorescent dyes with these properties have demonstrated high efficiency electroluminescence.

Only a few organic materials have been identified which show efficient room temperature phosphorescence from triplets. In contrast, many fluorescent dyes are known (C. H. Chen, J. Shi, and C. W. Tang, "Recent developments in molecular organic electroluminescent materials," Macromolecular Symposia, 1997, 125, 1–48; U. Brackmann, Lambdachrome Laser Dyes (Lambda Physik, Gottingen, 1997)) and fluorescent efficiencies in solution approaching 100% are not uncommon. (C. H. Chen, 1997, op. cit.) Fluorescence is also not affected by triplet-triplet annihilation, which degrades phosphorescent emission at high excitation densities. (M. A. Baldo, et al., "High efficiency phosphorescent emission from organic electroluminescent devices," Nature, 1998, 395, 151–154; M. A. Baldo, M. E. Thompson, and S. R. Forrest, "An analytic model of triplet-triplet annihilation in electrophosphorescent devices," 1999). Consequently, fluorescent materials are suited to many electroluminescent applications, particularly passive matrix displays.

To understand the different embodiments of this invention, it is useful to discuss the underlying mechanistic theory of energy transfer. There are two mechanisms commonly discussed for the transfer of energy to an acceptor molecule. In the first mechanism of Dexter transport (D. L.

Dexter, "A theory of sensitized luminescence in solids," J. Chem. Phys., 1953, 21, 836–850), the exciton may hop directly from one molecule to the next. This is a short-range process dependent on the overlap of molecular orbitals of neighboring molecules. It also preserves the symmetry of the donor and acceptor pair (E. Wigner and E. W. Wittmer, Uber die Struktur der zweiatomigen Molekelspektren nach der Quantenmechanik, Zeitschrift fur Physik, 1928, 51, 859–886; M. Klessinger and J. Michl, Excited states and photochemistry of organic molecules (VCH Publishers, New York, 1995)). Thus, the energy transfer of Eq. (1) is not possible via Dexter mechanism. In the second mechanism of Förster transfer (T. Förster, Zwischenmolekulare Energiewanderung and Fluoreszenz, Annalen der Physik, 1948, 2, 55–75; T. Förster, Fluoreszenz organischer Verbindugen (Vandenhoek and Ruprecht, Gottinghen, 1951 ), the energy transfer of Eq. (1) is possible. In Förster transfer, similar to a transmitter and an antenna, dipoles on the donor and acceptor molecules couple and energy may be transferred. Dipoles are generated from allowed transitions in both donor and acceptor molecules. This typically restricts the Forster mechanism to transfers between singlet states.

Nevertheless, as long as the phosphor can emit light due to some perturbation of the state such as due to spin-orbit coupling introduced by a heavy metal atom, it may participate as the donor in Förster transfer. The efficiency of the process is determined by the luminescent efficiency of the phosphor (F Wilkinson, in Advances in Photochemistry (eds. W. A. Noyes, G. Hammond, and J. N. Pitts), pp. 241–268, John Wiley & Sons, New York, 1964), i.e., if a radiative transition is more probable than a non-radiative decay, then energy transfer will be efficient. Such triplet-singlet transfers were predicted by Förster (T. Förster,"Transfer mechanisms of electronic excitation," Discussions of the Faraday Society, 1959, 27, 7–17) and confirmed by Ermolaev and Sveshnikova (V. L. Ermolaev and E. B. Sveshnikova, "Inductive-resonance transfer of energy from aromatic molecules in the triplet state," Doklady Akademii Nauk SSSR, 1963, 149, 1295–1298), who detected the energy transfer using a range of phosphorescent donors and fluorescent acceptors in rigid media at 77K or 90K. Large transfer distances are observed; for example, with triphenylamine as the donor and chrysoidine as the acceptor, the interaction range is 52 Å.

The remaining condition for Förster transfer is that the absorption spectrum should overlap the emission spectrum of the donor assuming the energy levels between the excited and ground state molecular pair are in resonance. In one example of this application, we use the green phosphor fac tris(2-phenylpyridine) iridium (Ir(ppy)$_3$; M. A. Baldo, et al., Appl. Phys. Lett., 1999, 75, 4–6) and the red fluorescent dye [2-methyl-6-[2-(2,3,6,7-tetrahydro-1H,5H-benzo[ij] quinolizin-9-yl) ethenyl]-4H-pyran-ylidene] propanedinitrile] ("DCM2"; C. W. Tang, S. A. VanSlyke, and C. H. Chen, "Electroluminescence of doped organic films," J. Appl. Phys., 1989, 65, 3610–3616). DCM2 absorbs in the green, and, depending on the local polarization field (V. Bulovic, et al., "Bright, saturated, red-to-yellow organic light-emitting devices based on polarization-induced spectral shifts," Chem. Phys. Lett., 1998, 287, 455–460), it emits at wavelengths between $\lambda$=570 nm and $\lambda$=650 nm.

It is possible to implement Förster energy transfer from a triplet state by doping a fluorescent guest into a phosphorescent host material. Unfortunately, such systems are affected by competitive energy transfer mechanisms that degrade the overall efficiency. In particular, the close proximity of the host and guest increase the likelihood of Dexter transfer between the host to the guest triplets. Once excitons reach the guest triplet state, they are effectively lost since these fluorescent dyes typically exhibit extremely inefficient phosphorescence.

To maximize the transfer of host triplets to fluorescent dye singlets, it is desirable to maximize Dexter transfer into the triplet state of the phosphor while also minimizing transfer into the triplet state of the fluorescent dye. Since the Dexter mechanism transfers energy between neighboring molecules, reducing the concentration of the fluorescent dye decreases the probability of triplet-triplet transfer to the dye. On the other hand, long range Förster transfer to the singlet state is unaffected. In contrast, transfer into the triplet state of the phosphor is necessary to harness host triplets, and may be improved by increasing the concentration of the phosphor.

Devices whose structure is based upon the use of layers of organic optoelectronic materials generally rely on a common mechanism leading to optical emission. Typically, this mechanism is based upon the radiative recombination of a trapped charge. Specifically, OLEDs are comprised of at least two thin organic layers separating the anode and cathode of the device. The material of one of these layers is specifically chosen based on the material's ability to transport holes, a "hole transporting layer" (HTL), and the material of the other layer is specifically selected according to its ability to transport electrons, an "electron transporting layer" (ETL). With such a construction, the device can be viewed as a diode with a forward bias when the potential applied to the anode is higher than the potential applied to the cathode. Under these bias conditions, the anode injects holes (positive charge carriers) into the hole transporting layer, while the cathode injects electrons into the electron transporting layer. The portion of the luminescent medium adjacent to the anode thus forms a hole injecting and transporting zone while the portion of the luminescent medium adjacent to the cathode forms an electron injecting and transporting zone. The injected holes and electrons each migrate toward the oppositely charged electrode. When an electron and hole localize on the same molecule, a Frenkel exciton is formed. Recombination of this short-lived state may be visualized as an electron dropping from its conduction potential to a valence band, with relaxation occurring, under certain conditions, preferentially via a photoemissive mechanism. Under this view of the mechanism of operation of typical thin-layer organic devices, the electroluminescent layer comprises a luminescence zone receiving mobile charge carriers (electrons and holes) from each electrode.

As noted above, light emission from OLEDs is typically via fluorescence or phosphorescence. There are issues with the use of phosphorescence. It has been noted that phosphorescent efficiency decreases rapidly at high current densities. It may be that long phosphorescent lifetimes cause saturation of emissive sites, and triplet-triplet annihilation may produce efficiency losses. Another difference between fluorescence and phosphorescence is that energy transfer of triplets from a conductive host to a luminescent guest molecule is typically slower than that of singlets; the long range dipole-dipole coupling (Förster transfer) which dominates energy transfer of singlets is (theoretically) forbidden for triplets by the principle of spin symmetry conservation. Thus, for triplets, energy transfer typically occurs by diffusion of excitons to neighboring molecules (Dexter transfer); significant overlap of donor and acceptor excitonic wavefunctions is critical to energy transfer. Another issue is that triplet diffusion lengths are typically long (e.g., >1400 Å)

compared with typical singlet diffusion lengths of about 200 Å. Thus, if phosphorescent devices are to achieve their potential, device structures need to be optimized for triplet properties. In this invention, we exploit the property of long triplet diffusion lengths to improve external quantum efficiency.

Successful utilization of phosphorescence holds enormous promise for organic electroluminescent devices. For example, an advantage of phosphorescence is that all excitons (formed by the recombination of holes and electrons in an EL), which are (in part) triplet-based in phosphorescent devices, may participate in energy transfer and luminescence in certain electroluminescent materials. In contrast, only a small percentage of excitons in fluorescent devices, which are singlet-based, result in fluorescent luminescence.

An alternative is to use phosphorescence processes to improve the efficiency of fluorescence processes. Fluorescence is in principle 75% less efficient due to the three times higher number of symmetric excited states.

Because one typically has at least one electron transporting layer and at least one hole transporting layer, one has layers of different materials, forming a heterostructure. The materials that produce the electroluminescent emission are frequently the same materials that function either as the electron transporting layer or as the hole transporting layer. Such devices in which the electron transporting layer or the hole transporting layer also functions as the emissive layer are referred to as having a single heterostructure. Alternatively, the electroluminescent material may be present in a separate emissive layer between the hole transporting layer and the electron transporting layer in what is referred to as a double heterostructure. The separate emissive layer may contain the emissive molecule doped into a host or the emissive layer may consist essentially of the emissive molecule.

That is, in addition to emissive materials that are present as the predominant component in the charge carrier layer, that is, either in the hole transporting layer or in the electron transporting layer, and that function both as the charge carrier material as well as the emissive material, the emissive material may be present in relatively low concentrations as a dopant in the charge carrier layer. Whenever a dopant is present, the predominant material in the charge carrier layer may be referred to as a host compound or as a receiving compound. Materials that are present as host and dopant are selected so as to have a high level of energy transfer from the host to the dopant material. In addition, these materials need to be capable of producing acceptable electrical properties for the OLED. Furthermore, such host and dopant materials are preferably capable of being incorporated into the OLED using starting materials that can be readily incorporated into the OLED by using convenient fabrication techniques, in particular, by using vacuum-deposition techniques.

The exciton blocking layer used in the devices of the present invention (and previously disclosed in U.S. appl. Ser. No. 09/153,144, now U.S. Pat. No. 6,097,147) substantially blocks the diffusion of excitons, thus substantially keeping the excitons within the emission layer to enhance device efficiency. The material of blocking layer of the present invention is characterized by an energy difference ("band gap") between its lowest unoccupied molecular orbital (LUMO) and its highest occupied molecular orbital (HOMO). In accordance with the present invention, this band gap substantially prevents the diffusion of excitons through the blocking layer, yet has only a minimal effect on the turn-on voltage of a completed electroluminescent device. The band gap is thus preferably greater than the energy level of excitons produced in an emission layer, such that such excitons are not able to exist in the blocking layer. Specifically, the band gap of the blocking layer is at least as great as the difference in energy between the triplet state and the ground state of the host.

It is desirable for OLEDs to be fabricated using materials that provide electroluminescent emission in a relatively narrow band centered near selected spectral regions, which correspond to one of the three primary colors, red, green and blue so that they may be used as a colored layer in an OLED or SOLED. It is also desirable that such compounds be capable of being readily deposited as a thin layer using vacuum deposition techniques so that they may be readily incorporated into an OLED that is prepared entirely from vacuum-deposited organic materials.

Co-pending application U.S. Ser. No. 08/774,087, filed Dec. 23, 1996, now U.S. Pat. No. 6,048,630, is directed to OLEDs containing emitting compounds that produce a saturated red emission.

SUMMARY OF THE INVENTION

The present invention is directed to organic light emitting devices wherein the emissive layer comprises an emissive molecule, optionally with a host material (wherein the emissive molecule is present as a dopant in said host material), which molecule is adapted to luminesce when a voltage is applied across the heterostructure, wherein the emissive molecule is selected from the group of phosphorescent organometallic complexes. The emissive molecule may be further selected from the group of phosphorescent organometallic platinum, iridium or osmium complexes and may be still further selected from the group of phosphorescent cyclometallated platinum, iridium or osmium complexes. A specific example of the emissive molecule is fac tris(2-phenylpyridine) iridium, denoted (Ir(ppy)₃) of formula

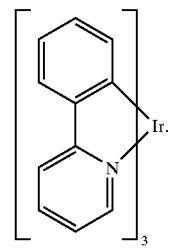

[In this, and later figures herein, we depict the dative bond from nitrogen to metal (here, Ir) as a straight line.]

The general arrangement of the layers is hole transporting layer, emissive layer, and electron transporting layer. For a hole conducting emissive layer, one may have an exciton blocking layer between the emissive layer and the electron transporting layer. For an electron conducting emissive layer, one may have an exciton blocking layer between the emissive layer and the hole transporting layer. The emissive layer may be equal to the hole transporting layer (in which case the exciton blocking layer is near or at the anode) or to the electron transporting layer (in which case the exciton blocking layer is near or at the cathode).

The emissive layer may be formed with a host material in which the emissive molecule resides as a guest or the emissive layer may be formed of the emissive molecule itself. In the former case, the host material may be a hole-transporting material selected from the group of substituted tri-aryl amines. The host material may be an electron-transporting material selected from the group of metal quinoxolates, oxadiazoles and triazoles. An example of a host material is 4,4'-N,N'-dicarbazole-biphenyl (CBP), which has the formula:

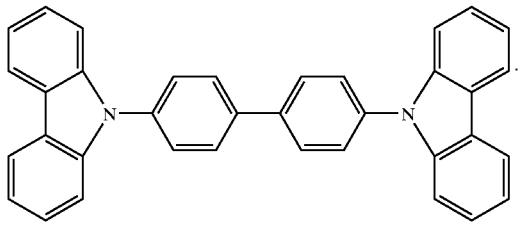

The emissive layer may also contain a polarization molecule, present as a dopant in said host material and having a dipole moment, that affects the wavelength of light emitted when said emissive dopant molecule luminesces.

A layer formed of an electron transporting material is used to transport electrons into the emissive layer comprising the emissive molecule and the (optional) host material. The electron transporting material may be an electron-transporting matrix selected from the group of metal quinoxolates, oxadiazoles and triazoles. An example of an electron transporting material is tris-(8-hydroxyquinoline) aluminum ($Alq_3$).

A layer formed of a hole transporting material is used to transport holes into the emissive layer comprising the emissive molecule and the (optional) host material. An example of a hole transporting material is 4,4'-bis[N-(1-naphthyl)-N-phenyl-amino] biphenyl ["α-NPD"].

The use of an exciton blocking layer ("barrier layer") to confine excitons within the luminescent layer ("luminescent zone") is greatly preferred. For a hole-transporting host, the blocking layer may be placed between the luminescent layer and the electron transport layer. An example of a material for such a barrier layer is 2,9-dimethyl-4,7-diphenyl-1,10-phenanthroline (also called bathocuproine or BCP), which has the formula:

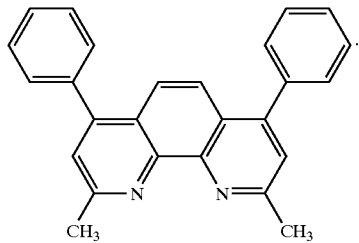

For a situation with a blocking layer between a hole-conducting host and the electron transporting layer (as is the case in Example 2 below), one seeks the following characteristics, which are listed in order of relative importance.

1. The difference in energy between the LUMO and HOMO of the blocking layer is greater than the difference in energy between the triplet and ground state singlet of the host material.
2. Triplets in the host material are not quenched by the blocking layer.
3. The ionization potential (IP) of the blocking layer is greater than the ionization potential of the host. (Meaning that holes are held in the host.)
4. The energy level of the LUMO of the blocking layer and the energy level of the LUMO of the host are sufficiently close in energy such that there is less than 50% change in the overall conductivity of the device.
5. The blocking layer is as thin as possible subject to having a thickness of the layer that is sufficient to effectively block the transport of excitons from the emissive layer into the adjacent layer.

That is, to block excitons and holes, the ionization potential of the blocking layer should be greater than that of the HTL, while the electron affinity of the blocking layer should be approximately equal to that of the ETL to allow for facile transport of electrons.

[For a situation in which the emissive ("emitting") molecule is used without a hole transporting host, the above rules for selection of the blocking layer are modified by replacement of the word "host" by "emitting molecule."]

For the complementary situation with a blocking layer between a electron-conducting host and the hole-transporting layer one seeks characteristics (listed in order of importance):

1. The difference in energy between the LUMO and HOMO of the blocking layer is greater than the difference in energy between the triplet and ground state singlet of the host material.
2. Triplets in the host material are not quenched by the blocking layer.
3. The energy of the LUMO of the blocking layer is greater than the energy of the LUMO of the (electron-transporting) host. (Meaning that electrons are held in the host.)
4. The ionization potential of the blocking layer and the ionization potential of the host are such that holes are readily injected from the blocker into the host and there is less than a 50% change in the overall conductivity of the device.
5. The blocking layer is as thin as possible subject to having a thickness of the layer that is sufficient to effectively block the transport of excitons from the emissive layer into the adjacent layer.

[For a situation in which the emissive ("emitting") molecule is used without an electron transporting host, the above rules for selection of the blocking layer are modified by replacement of the word "host" by "emitting molecule."]

The present invention covers articles of manufacture comprising OLEDs comprising a new family of phosphorescent materials, which can be used as dopants in OLEDs, and methods of manufacturing the articles. These phosphorescent materials are cyclometallated platinum, iridium or osmium complexes, which provide electroluminiscent emission at a wavelength between 400 nm and 700 nm. The present invention is further directed to OLEDs that are capable of producing an emission that will appear blue, that will appear green, and that will appear red.

More specifically, OLEDs of the present invention comprise, for example, an emissive layer comprised of platinum (II) complexed with Bis[2-(2-phenyl)pyridinato-N,C2], Bis[2-(2'-thienyl)pyridinato-N,C3], and Bis[benzo (h)quinolinato-N,C]. The compound cis-Bis[2-(2'-thienyl) pyridinato-N,C3] Pt(II) gives a strong orange to yellow emission.

The invention is further directed to emissive layers wherein the emissive molecule is selected from the group of phosphorescent organometallic complexes, wherein the emissive molecule contains substituents selected from the class of electron donors and electron acceptors. The emissive molecule may be further selected from the group of phosphorescent organometallic platinum, iridium or osmium complexes and may be still further selected from the group of phosphorescent cyclometallated platinum, iridium or osmium complexes, wherein the organic molecule contains substituents selected from the class of electron donors and electron acceptors.

The invention is further directed to an organic light emitting device comprising a heterostructure for producing luminescence, wherein the emissive layer comprises a host material, an emissive molecule, present as a dopant in said host material, adapted to luminesce when a voltage is applied across the heterostructure, wherein the emissive molecule is selected from the group consisting of cyclometallated platinum, iridium or osmium complexes and wherein there is a polarization molecule, present as a dopant in the host material, which polarization molecule has a dipole moment and which polarization molecule alters the wavelength of the luminescent light emitted by the emissive dopant molecule. The polarization molecule may be an aromatic molecule substituted by electron donors and electron acceptors.

The present invention is directed to OLEDs, and a method of fabricating OLEDs, in which emission from the device is obtained via a phosphorescent decay process wherein the phosphorescent decay rate is rapid enough to meet the requirements of a display device. More specifically, the present invention is directed to OLEDs comprised of a material that is capable of receiving the energy from an exciton singlet or triplet state and emitting that energy as phosphorescent radiation.

The OLEDs of the present invention may be used in substantially any type of device which is comprised of an OLED, for example, in OLEDs that are incorporated into a larger display, a vehicle, a computer, a television, a printer, a large area wall, theater or stadium screen, a billboard or a sign.

The present invention is also directed to complexes of formula L L'L" M, wherein L, L', and L" are distinct bidentate ligands and M is a metal of atomic number greater than 40 which forms an octahedral complex with the three bidentate ligands and is preferably a member of the third row (of the transition series of the periodic table) transition metals, most preferably Ir and Pt. Alternatively, M can be a member of the second row transition metals, or of the main group metals, such as Zr and Sb. Some of such organometallic complexes electroluminesce, with emission coming from the lowest energy ligand or MLCT state. Such electroluminescent compounds can be used in the emitter layer of organic light emitting diodes, for example, as dopants in a host layer of an emitter layer in organic light emitting diodes. This invention is further directed to organometallic complexes of formula L L'L" M, wherein L, L', and L" are the same (represented by $L_3M$) or different (represented by L L'L" M), wherein L, L', and L" are bidentate, monoanionic ligands, wherein M is a metal which forms octahedral complexes, is preferably a member of the third row of transition metals, more preferably Ir or Pt, and wherein the coordinating atoms of the ligands comprise $sp^2$ hybridized carbon and a heteroatom. The invention is further directed to compounds of formula $L_2MX$, wherein L and X are distinct bidentate ligands, wherein X is a monoanionic bidentate ligand, wherein L coordinates to M via atoms of L comprising $sp^2$ hybridized carbon and heteroatoms, and wherein M is a metal forming an octahedral complex, preferably iridium or platinum. It is generally expected that the ligand L participates more in the emission process than does X. The invention is directed to meridianal isomers of $L_3M$ wherein the heteroatoms (such as nitrogen) of two ligands L are in a trans configuration. In the embodiment in which M is coordinated with an $sp^2$ hybridized carbon and a heteroatom of the ligand, it is preferred that the ring comprising the metal M, the $SP^2$ hybridized carbon and the heteroatom contains 5 or 6 atoms. These compounds can serve as dopants in a host layer which functions as a emitter layer in organic light emitting diodes.

Furthermore, the present invention is directed to the use of complexes of transition metal species M with bidentate ligands L and X in compounds of formula $L_2MX$ in the emitter layer of organic light emitting diodes. A preferred embodiment is compounds of formula $L_2IrX$, wherein L and X are distinct bidentate ligands, as dopants in a host layer functioning as an emitter layer in organic light emitting diodes.

The present invention is also directed to an improved synthesis of organometallic molecules which function as emitters in light emitting devices. These compounds of this invention can be made according to the reaction:

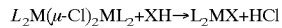

$$L_2M(\mu\text{-Cl})_2ML_2 + XH \rightarrow L_2MX + HCl$$

wherein $L_2M(\mu\text{-Cl})_2ML_2$ is a chloride bridged dimer with L a bidentate ligand, and M a metal such as Ir; XH is a Bronsted acid which reacts with bridging chloride and serves to introduce a bidentate ligand X, where XH can be, for example, acetylacetone, 2-picolinic acid, or N-methylsalicyclanilide, and H represents hydrogen. The method involves combining the $L_2M(\mu\text{-Cl})_2ML_2$ chloride bridged dimer with the XH entity. The resultant product of the form $L_2MX$ has approximate octahedral disposition of the bidentate ligands L, L, and X about M.

The resultant compounds of formula $L_2MX$ can be used as phosphorescent emitters in organic light emitting devices. For example, the compound wherein L=(2-phenylbenzothiazole), X=acetylacetonate, and M=Ir (the compound abbreviated as BTIr) when used as a dopant in 4,4'-N,N'-dicarbazole-biphenyl (CBP) (at a level 12% by mass) to form an emitter layer in an OLED shows a quantum efficiency of 12%. For reference, the formula for CBP is:

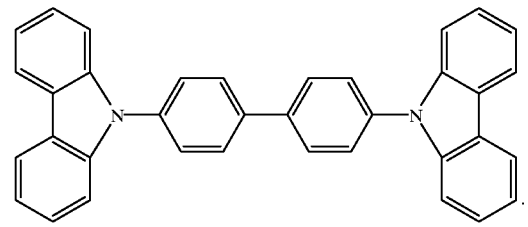

The synthetic process to make $L_2MX$ compounds of the present invention may be used advantageously in a situation in which L, by itself, is fluorescent but the resultant $L_2MX$ is phosphorescent. One specific example of this is where L=coumarin-6.

The synthetic process of the present invention facilitates the combination of L and X pairs of certain desirable characteristics. For example, the present invention is further directed to the appropriate selection of L and X to allow color tuning of the complex $L_2MX$ relative to $L_3M$. For example, $Ir(ppy)_3$ and $(ppy)_2Ir(acac)$ both give strong green emission with a $\lambda_{max}$ of 510 nm (ppy denotes phenyl pyridine). However, if the X ligand is formed from picolinic acid instead of from acetylacetone, there is a small blue shift of about 15 nm.

Furthermore, the present invention is also directed to a selection of X such that it has a certain HOMO level relative to the $L_3M$ complex so that carriers (holes or electrons) might be trapped on X (or on L) without a deterioration of emission quality. In this way, carriers (holes or electrons) which might otherwise contribute to deleterious oxidation or reduction of the phosphor would be impeded. The carrier that is remotely trapped could readily recombine with the opposite carrier either intramolecularly or with the carrier from an adjacent molecule.

The present invention, and its various embodiments, are discussed in more detail in the examples below. However, the embodiments may operate by different mechanisms. Without limitation and without limiting the scope of the invention, we discuss the different mechanisms by which various embodiments of the invention may operate.

DETAILED DESCRIPTION OF THE INVENTION

Figure 1:
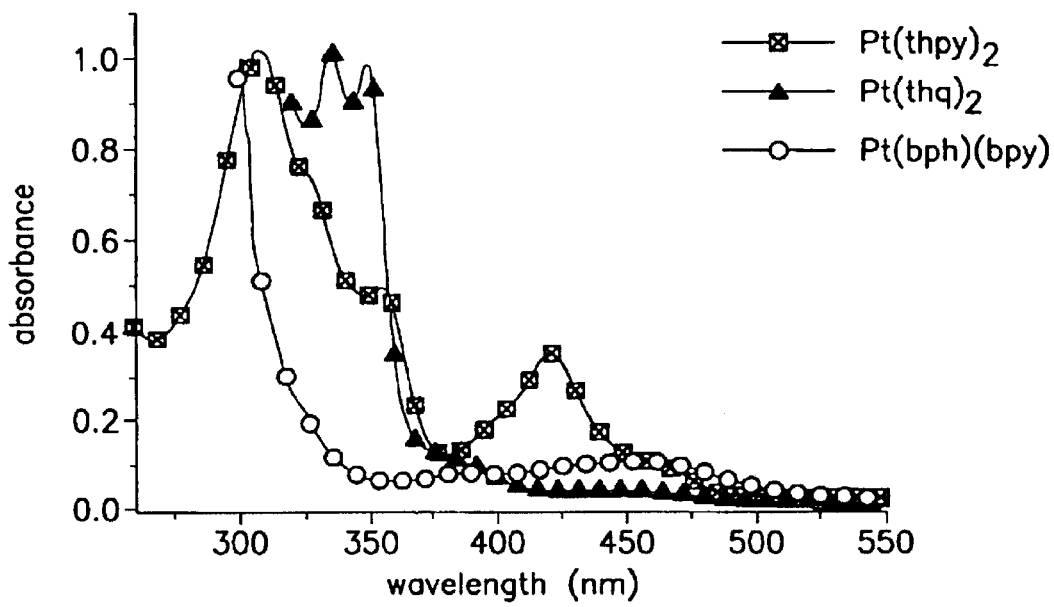
FIG. 1. Electronic absorbance spectra of $Pt(thpy)_2$, $Pt(thq)_2$, and $Pt(bph)(bpy)$.

The present invention is generally directed to emissive molecules, which luminesce when a voltage is applied across a heterostructure of an organic light-emitting device and which molecules are selected from the group of phosphorescent organometallic complexes, and to structures, and correlative molecules of the structures, that optimize the emission of the light-emitting device. The term "organometallic" is as generally understood by one of ordinary skill, as given, for example, in "Inorganic Chemistry" (2nd edition) by Gary L. Miessler and Donald A. Tarr, Prentice-Hall (1998). The invention is further directed to emissive molecules within the emissive layer of an organic light-emitting device which molecules are comprised of phosphorescent cyclometallated platinum, iridium or osmium complexes. On electroluminescence, molecules in this class may produce emission which appears red, blue, or green. Discussions of the appearance of color, including descriptions of CIE charts, may be found in H. Zollinger, Color Chemistry, VCH Publishers, 1991 and H. J. A. Dartnall, J. K. Bowmaker, and J. D. Mollon, Proc. Roy. Soc. B (London), 1983, 220, 115–130.

The present invention will now be described in detail for specific preferred embodiments of the invention, it being understood that these embodiments are intended only as illustrative examples and the invention is not to be limited thereto.

Synthesis of the Cyclometallated Platinum Complexes

We have synthesized a number of different Pt cyclometallated complexes.

Numerous publications, reviews and books are dedicated to the chemistry of cyclometallated compounds, which also are called intramolecular-coordination compounds. (I.Omae, Organometallic Intramolecular-coordination compounds. N.Y. 1986. G. R. Newkome, W. E. Puckett, V. K. Gupta, G. E. Kiefer, *Chem. Rev.* 1986,86, 451. A. D. Ryabov, *Chem. Rev.* 1990, 90, 403). Most of the publications depict mechanistical aspects of the subject and primarily on the cyclometallated compounds with one bi- or tri-dentate ligand bonded to metal by C-M single bond and having cycle closed with one or two other X-M bonds where X may be N, S, P, As, O. Not so much literature was devoted to bis- or tris-cyclometallated complexes, which do not possess any other ligands but C,N type bi-dentate ones. Some of the subject of this invention is in these compounds because they are not only expected to have interesting photochemical properties as most cyclometallated complexes do, but also should exhibit increased stability in comparison with their monocyclometallated analogues. Most of the work on bis-cyclopaladated and bis-cycloplatinated compounds was performed by von Zelewsky et al (For a review see: M.Maestri, V.Balzani, Ch.Deuschel-Comioley, A.von Zelewsky, *Adv. Photochem.* 1992 17, 1. L.Chassot, A.Von Zelewsky, *Helv. Chim.Acta* 1983, 66, 243. L.Chassot, E.Muler, A. von Zelewsky, *Inorg. Chem.* 1984, 23, 4249. S Bonafede, M.Ciano, F.Boletta, V.Balzani, L.Chassot, A. von Zelewsky, *J.Phys. Chem.* 1986, 90, 3836. L.Chassot, A.von Zelewsky, D.Sandrini, M.Maestri, V.Balzani, *J.Am. Chem. Soc.* 1986, 108, 6084. Ch.Cornioley-Deuschel, A.von Zelewsky, *Inorg. Chem.* 1987, 26, 3354. L.Chassot, A.von Zelewsky, *Inorg.Chem.* 1987, 26, 2814. A.von Zelewsky, A. P. Suckling, H.Stoeckii-Evans, *Inorg.Chem.* 1993, 32, 4585. A. von Zelewsky, P.Belser, P.Hayoz, R.Dux, X.Hua, A.Suckling, H.Stoeckii-Evans, *Coord. Chem.Rev.* 1994, 132, 75. P.Jolliet, M.Gianini, A.von Zelewsky, G.Bemardinelli, H.Stoeckii-Evans, *Inorg.Chem.* 1996, 35, 4883. H.Wiedenhofer, S.Schutzenmeier, A.von Zelewsky, H.Yersin, *J.Phys. Chem.* 1995, 99, 13385. M. Gianini, A.von Zelewsky, H. Stoeckii-Evans, *Inorg. Chem.* 1997,36, 6094.) In one of their early works, (M.Maestri, D.Sandrini, V.Balzani, L.Chassot, P.Jolliet, A.von Zelewsky, *Chem.Phys.Lett.* 1985,122,375) luminescent properties of three bis-cycloplatinated complexes were investigated in detail. The summary of the previously reported results on Pt bis-cyclometallated complexes important for our current research is as follows:

i. in general, cyclometallated complexes having a 5-membered ring formed between the metal atom and C,X ligand are more stable.

ii. from the point of view of stability of resulting compounds, complexes not containing anionic ligands are preferred; thus, bis-cyclometallated complexes are preferred to mono-cyclometallated ones.

iii. a variety of Pt(Pd) cyclometallated complexes were synthesized, homoleptic (containing similar C,X ligands), heteroleptic (containing two different cyclometallating C,X ligands) and complexes with one C,C cyclometallating ligand and one N,N coordinating ligand.

iv. most bis-cyclometallated complexes show $M^+$ ions upon electron impact ionization in their mass spectra; this can be a base for our assumption on their stability upon vacuum deposition.

v. on the other hand, some of the complexes are found not to be stable in certain solvents; they undergo oxidative addition reactions leading to Pt(IV) or Pd(IV) octahedral complexes.

vi. optical properties are reported only for some of the complexes; mostly absorption data is presented. Low-energy electron transitions observed in both their absorption and emission spectra are assigned to MLCT transitions.

vii. reported luminescent properties are summarized in Table 1. Used abbreviations are explained in Scheme 1. Upon transition from bis-cyclometalated complexes with two C,N ligands to the complexes with one C,C and one N,N ligand batochromic shift in emission was observed. (M.Maestri, D.Sandrini, V.Balzani, A.von Zelewsky, C.Deuschel-Cornioley, P.Jolliet, *Helv. Chim.Acta* 1988, 71, 1053.

TABLE 1

Absorption and emission properties of several cycloplatinated complexes. Reproduced from A.von Zelewsky et. al (Chem. Phys. Lett., 1985, 122, 375 and Helv. Chim. Acta 1988, 17, 1053). Abbreviation explanations are given in Scheme 1.

| | | | emission spectra | |
|---|---|---|---|---|
| | solvent | absorption $\lambda max(\epsilon)$ | 77K $\lambda max(\tau)$ | 293K $\lambda max(\tau)$ |
| $Pt(Phpy)_2(1)$ | $CH_3CN$ | 402(12800) 291(27700) | 491(4.0) | — |
| $Pt(Thpy)_2(2)$ | $CH_3CN$ | 418(10500) 303(26100) | 570(12.0) | 578(2.2) |
| $Pt(Bhq)_2(3)$ | $CH_3CN$ | 421(9200) 367(12500) 307(15000) | 492(6.5) | — |
| $Pt(bph)(bpy)(4)$ | | | | |

Scheme 1
Explanations for abbreviations used in table 1.

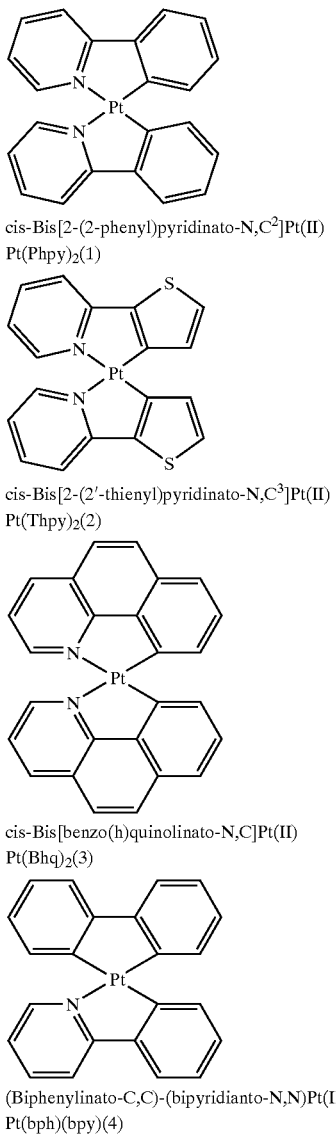

cis-Bis[2-(2-phenyl)pyridinato-N,C$^2$]Pt(II)
Pt(Phpy)$_2$(1)

cis-Bis[2-(2'-thienyl)pyridinato-N,C$^3$]Pt(II)
Pt(Thpy)$_2$(2)

cis-Bis[benzo(h)quinolinato-N,C]Pt(II)
Pt(Bhq)$_2$(3)

(Biphenylinato-C,C)-(bipyridianto-N,N)Pt(II)
Pt(bph)(bpy)(4)

We synthesized different bis-cycloplatinated complexes in order to investigate their optical properties in different hosts, both polymeric and molecular, and utilize them as dopants in corresponding hosts for organic light-emitting diodes (OLEDs). Usage of the complexes in molecular hosts in OLEDs prepared in the vacuum deposition process requires several conditions to be satisfied. The complexes should be sublimable and stable at the standard deposition conditions (vacuum~10$^{-6}$ torr). They should show emission properties interesting for OLED applications and be able to accept energy from host materials used, such as Alq$_3$ or NPD. On the other hand, in order to be useful in OLEDs prepared by wet techniques, the complexes should form true solutions in conventional solvents (e.g., CHCl$_3$) with a wide range of concentrations and exhibit both emission and efficient energy transfer from polymeric hosts (e.g., PVK). All these properties of cycloplatinated complexes were tested. In polymeric hosts we observe efficient luminescence from some of the materials.

Syntheses proceeded as follows:
2-(2-thienyl)pyridine. Synthesis is shown in Scheme 2, and was performed according to procedure close to the published one (T.Kauffmann, A.Mitschker, A.Woltermann, *Chem.Ber.* 1983, 116, 992). For purification of the product, instead of recommended distillation, zonal sublimation was used (145-145-125° C., 2–3 hours). Light brownish white solid (yield 69%). Mass-spec: m/z: 237(18%), 161 (100%, M$^+$), 91 (71%). $^1$H NMR (250 MHZ, DMSO-d$_6$) δ,ppm: 6.22–6.28 (d. of d., 1H), 6.70–6.80 (d. of d., 1H), 6.86–7.03 (m,3H), 7.60–7.65 (m,1H). $^{13}$C NMR (250 MHZ, DMSO-d$_6$): 118.6, 122.3, 125.2, 128.3, 128.4, 137.1, 144.6, 149.4, 151.9.

Scheme 2
Synthesis of 2-(2-thienyl)pyridine.

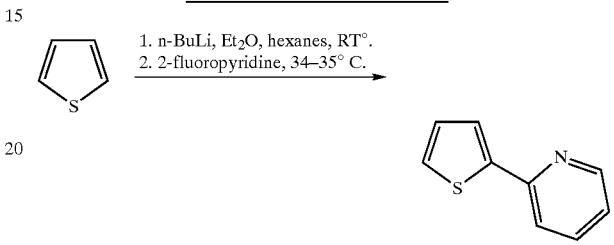

2-(2-thienyl)quinoline. Synthesis is displayed in Scheme 3, and was made according to published procedure (K. E. Chippendale, B.Iddon, H.Suschitzky, *J Chem.Soc.* 1949, 90, 1871). Purification was made exactly following the literature as neither sublimation nor column chromatography did not give as good results as recrystallizations from (a) petroleum ether, and (b) EtOH—H$_2$O (1:1) mixture. Pale yellow solid, gets more yellow with time (yield 84%). Mass-spec: m/z: 217 (32%), 216 (77%), 215 (83%), 214 (78%), 213 (77%), 212 (79%), 211(100%, M$^+$), 210 (93%), 209 (46%). $^1$H NMR (250 MHZ, DMSO-d$_6$) δ,ppm: 7.18–7.24 (d. of d.,1H), 7.48–7.58 (d. of d. of d.,1H), 7.67–7.78 (m,2H), 7.91–7.97 (m,3H), 8.08–8.11 (d,1H), 8.36–8.39 (d,1H).

Scheme 3
Synthesis of 2-(2-thienyl)quinoline.

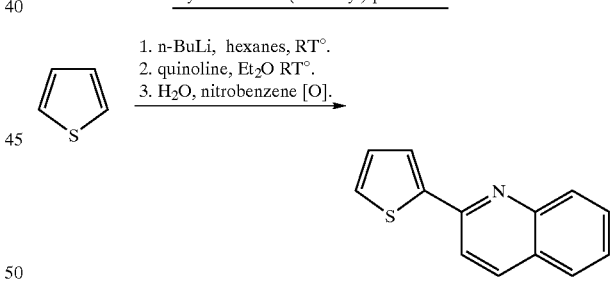

2-(2'-bromophenyl)pyridine. Synthesis was performed according to literature (D. H. Hey, C. J. M. Stirling, G. H. Williams, *J.Chem. Soc.* 1955, 3963; R. A. Abramovich, J. G. Saha, *J. Chem.Soc.* 1964, 2175). It is outlined in Scheme 4. Literature on the subject was dedicated to the study of aromatic substitution in different systems, including pyridine, and study of isomeric ratios in the resulting product. Thus in order to resolve isomer mixtures of different substituted phenylpyridines, not 2-(2'-bromophenyl)pyridine, the authors utilized 8 ft.×¼ in. column packed with ethylene glycol succinate (10%) on Chromosorb W at 155° C. and some certain helium inlet pressure. For resolving the reaction mixture we obtained, we used column chromatography with hexanes:THF (1:1) and haxanes:THF:PrOH-1 (4:4:1) mixtures as eluents on silica gel because this solvent mixture gave best results in TLC (three well resolved spots).

Only the first spot in the column gave mass spec major peak corresponding to n-(2'-bromophenyl)pyridines (m/z: 233, 235), in the remaining spots this peak was minor. Mass spec of the first fraction: m/z: 235 (97%), 233 (100%,M+), 154 (86%), 127 (74%). $^1$H NMR of the first fraction (250 MHZ, DMSO-d6) δ, ppm: 7.27–7.51 (m,4H), 7.59–7.96 (m,2H), 8.57–8.78 (m,2H).

Scheme 4
Synthesis of n-(2'-bromophenyl)pyridines.

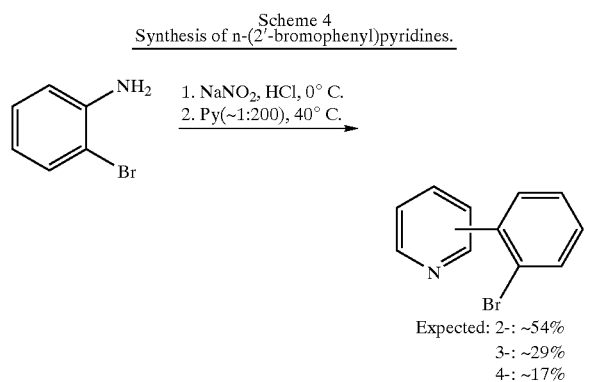

Expected: 2-: ~54%
3-: ~29%
4-: ~17%

Sublimation of the 1$^{st}$ fraction product after column did not lead to disappearance of the peaks of contaminants in $^1$H NMR spectrum, and we do not expect the sublimation to lead to resolving the isomers if present.

2-phenylpyridine. Was synthesized by literature procedure (J. C. W. Evans, C. F. H. Allen, *Org. Synth. Cell.* 1943, 2, 517) and is displayed in Scheme 5. Pale yellow oil darkening in the air (yield 48%). $^1$H NMR (250 MHZ, DMSO-d$_6$) of the product after vacuum distillation: δ,ppm: 6.70–6.76 (m,1H), 6.92–7.10 (m,3H), 7.27–7.30 (m,1H), 7.36–7.39 (q,1H), 7.60–7.68 (m,2H), 8.16–8.23 (m,1H)).

Scheme 5
Synthesis of 2-phenylpyridine

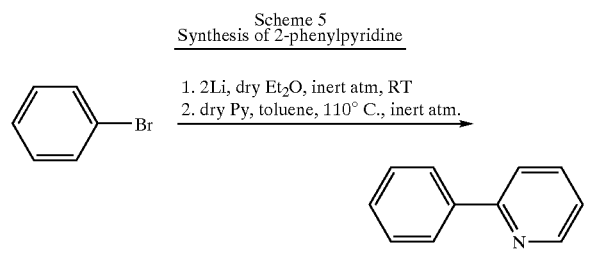

2,2'-diaminobiphenyl. Was prepared by literature method (R. E. Moore, A. Furst, *J. Org. Chem.* 1958, 23, 1504) (Scheme 6). Pale pink solid (yield 69%). $^1$H NMR (250 MHZ, DMSO-d$_6$) δ,ppm: 5.72–5.80 (t. of d.,2H), 5.87–5.93 (d. of d., 2H), 6.03–6.09 (d. of d.,2H), 6.13–6.23 (t. of d.,2H). Mass spec: m/z: 185 (40%), 184 (100%, M+), 183 (73%), 168 (69%), 167 (87%), 166 (62%), 139 (27%).

Scheme 6
Synthesis of 2,2'-dibromobiphenyl from 2,2'-dinitrobiphenyl.

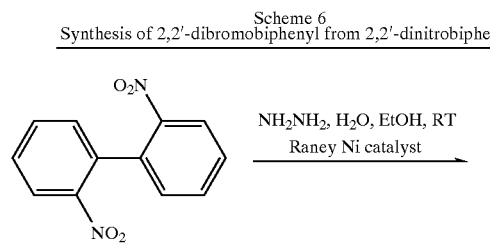

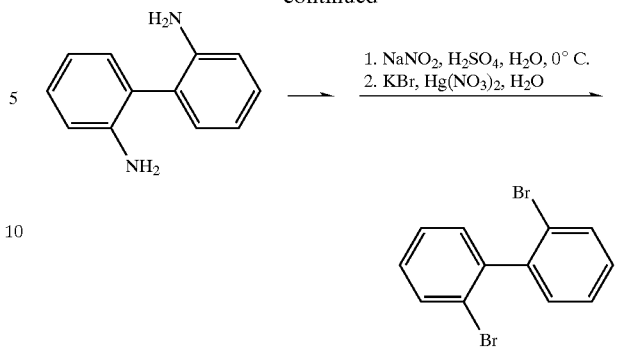

2,2'-dibromobiphenyl. (Scheme 6) (A. Uehara, J. C. Bailar, Jr., *J.Organomet. Chem.*1982, 239,1).

2,2'-dibromo-1, 1'-binaphthyl. Was synthesized according to literature (H.Takaya, S. Akutagawa, R.Noyori, *Org.Synth.* 1989, 67,20) (Scheme 7).

Scheme 7
Synthesis of 2,2'-dibromo-1,1'-binaphthyl.

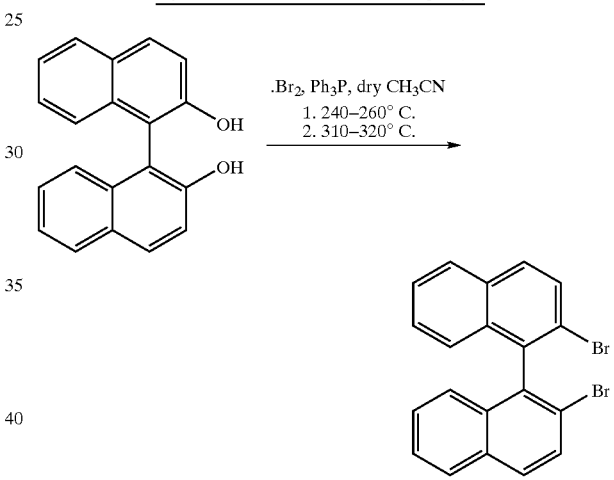

trans-Dichloro-bis-(diethyl sulfide) platinum (II). Prepared by a published procedure (G. B. Kauffman, D. O. Cowan, *Inorg. Synth.* 1953, 6, 211) (Scheme 8). Bright yellow solid (yield 78%).

cis-Dichloro-bis-(diethyl sulfide) platinum (II). Prepared by a published procedure (G. B. Kauffman, D. O. Cowan, *Inorg. Synth.* 1953, 6, 211). (Scheme 8). Yellow solid (63%).

Scheme 8:
Syntheses of cis- and trans-Dichloro-bis-(diethyl sulfide) platinum (II).

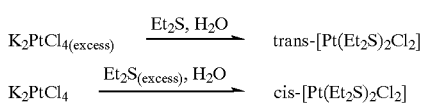

cis-Bis[2-(2'-thienyl)pyridinato-N, C$^{5'}$ platinum (II). Was synthesized according to literature methods (L. Chassot, A. von Zelewsky, *Inorg. Chem.* 1993, 32, 4585). (Scheme 9). Bright red crystals (yield 39%). Mass spec: m/z: 518 (25%), 517 (20%), 516 (81%), 513 (100%,M+), 514 (87%), 481 (15%), 354 (23%).

Scheme 9
Synthesis of cis-bis[2-(2'-thienyl)pyridinato-N,C3]platinum (II).

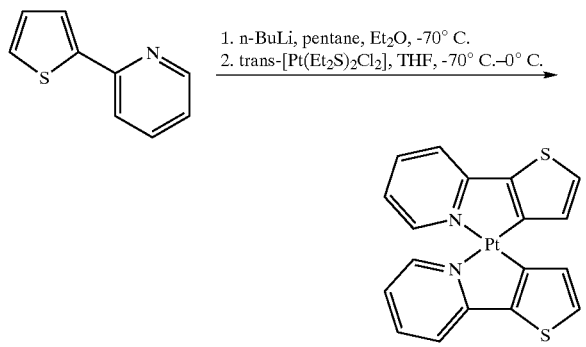

cis-Bis[2-(2'-thienyl)quinolinato-N, $C^3$) platinum (II). Was prepared following published procedures (P. Jolliet, M. Gianini, A. von Zelewsky, G. Bemardinelli, H. Stoeckii-Evans, *Inorg. Chem.* 1996, 35, 4883). (Scheme 10). Dark red solid (yield 21%).

Scheme 10
Synthesis of cis-Bis[2-(2'-thienyl)quinolinato-N,$C^{5'}$]platinum (II).

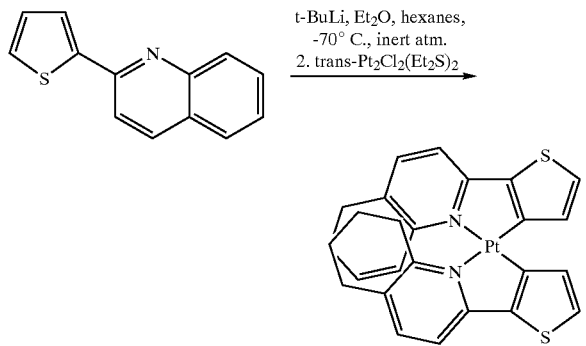

Absorption spectra were recorded on AVIV Model 14DS-UV-Vis-IR spectrophotometer and corrected for background due to solvent absorption. Emission spectra were recorded on PTI QuantaMaster Model C-60SE spectrometer with 1527 PMT detector and corrected for detector sensitivity inhomogeneity.

Vacuum deposition experiments were performed using standard high vacuum system (Kurt J.Lesker vacuum chamber) with vacuum ~$10^{-6}$ torr. Quartz plates (ChemGlass Inc.) or borosilicate glass-IndiumTin Oxide plates (ITO, Delta Technologies,Lmtd.), if used as substrates for deposition, were precleaned according to the published procedure for the later (A. Shoustikov, Y. You, P. E. Burrows, M. E. Thomspon, S. R. Forrest, *Synth. Met.* 1997, 91, 217).

Thin film spin coating experiments were done with standard spin coater (Specialty Coating Systems, Inc.) with regulatable speed, acceleration speed, and deceleration speed. Most films were spun coat with 4000 RPM speed and maximum acceleration and deceleration for 40 seconds.
Optical properties of the Pt cyclometallated complexes are shown above in Table 1.
Optical Properties in Solution:

Absorbance spectra of the complexes Pt(thpY)$_2$, Pt(thq)$_2$ and Pt(bph)(bpy) in solution (CHCl$_3$ or CH$_2$Cl$_2$) were normalized and are presented in FIG. 1. Absorption maximum for Pt(phpy)$_2$ showed a maximum at ca. 400 nm, but because the complex apparently requires further purification, the spectrum is not presented.

Figure 2:
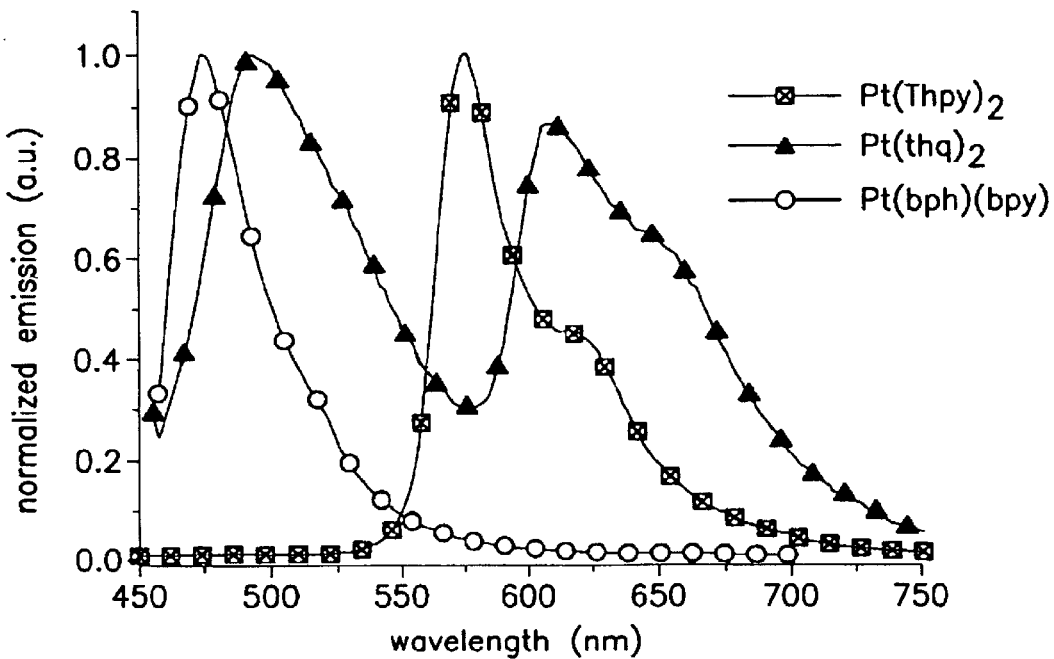
FIG. 2. Emission spectra of $Pt(thpy)_2$, $Pt(thq)_2$, and $Pt(bph)(bpy)$.

Normalized emission spectra are shown in FIG. 2. Excitation wavelengths for Pt(thpy)$_2$, Pt(thq)$_2$ and Pt(bph)(bpy) are correspondingly 430 nm, 450 nm, and 449 nm (determined by maximum values in their excitation spectra). Pt(thpy)$_2$ gives strong orange to yellow emission, while Pt(thq)$_2$ gives two lines at 500 and 620 nm. The emission form these materials is due to efficient phosphorescence. Pt(bph)(bpy) gives blue emission, centered at 470 nm. The emission observed for Pt(bph)(bpy) is most likely due to fluorescence and not phosphorescence.

Emission Lifetimes and Quantum Yields in Solution:

| | | |
|---|---|---|
| Pt(thPy)$_2$: | 3.7 µs (CHCl$_3$, deoxygenated for 10 min) | 0.27 |
| Pt(thq)$_2$: | 2.6 µs (CHCl$_3$, deoxygenated for 10 min) | not measured |
| Pt(bph)(bpy): | not in µs region (CH$_2$O$_2$, deoxygenated for 10 min) | not measured |

Optical Properties in PS Solid Matrix:

Pt(thpy)$_2$: Emission maximum is at 580 nm (lifetime 6.5 µs) upon excitation at 400 nm. Based on the increased lifetime for the sample in polystyrene we estimate a quantum efficiency in polystyrene for Pt(thpy)$_2$ of 0.47.

Pt(thq)$_2$: Emission maximum at 608 nm (lifetime 7.44 µs) upon excitation at 450 nm.

Figure 3:
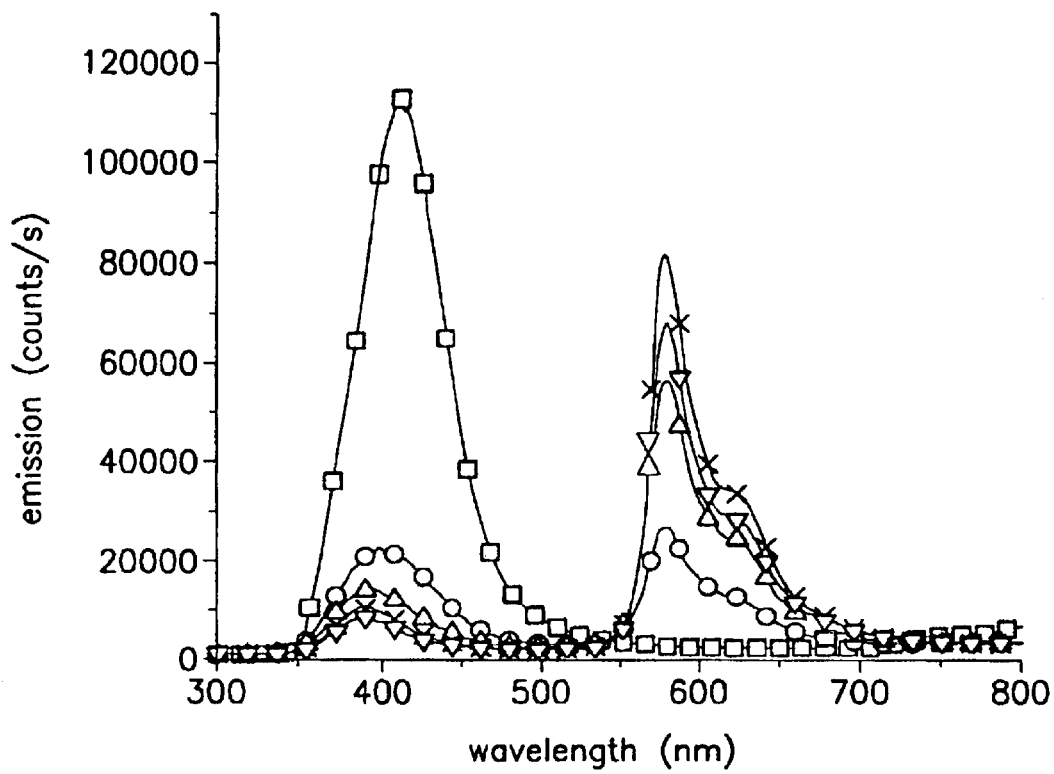
FIG. 3. Energy transfer from polyvinylcarbazole (PVK) to $Pt(thpy)_2$ in the solid film.

Optical Properties of the Complexes in PVK Film:

These measurements were made for Pt(thpy)$_2$ only. Polyvinylcarbazole (PVK) was excited at 250 nm and energy transfer from PVK to Pt(thpy)$_2$ was observed (FIG. 3). The best weight PVK:Pt(thpy)$_2$ ratio for the energy transfer was found to be ca. 100:6.3.

EXAMPLES OF LIGHT EMITTING DIODES

Example 1

ITO/PVK:PBD.Pt(thpy)$_2$ (100:40:2)/Ag:Mg/Ag

Figure 4A:
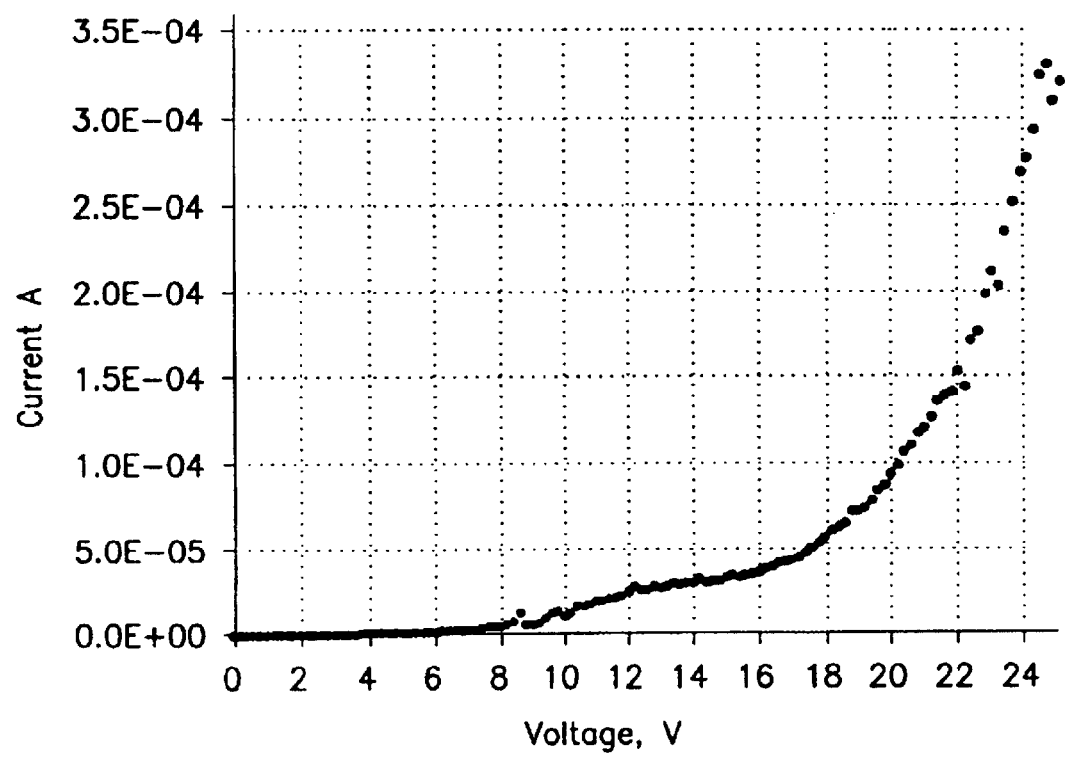
FIG. 4. Characteristics of OLED with $Pt(thpy)_2$ dopant: (a) I-V characteristic; (b) Light output curve.
Figure 4B:
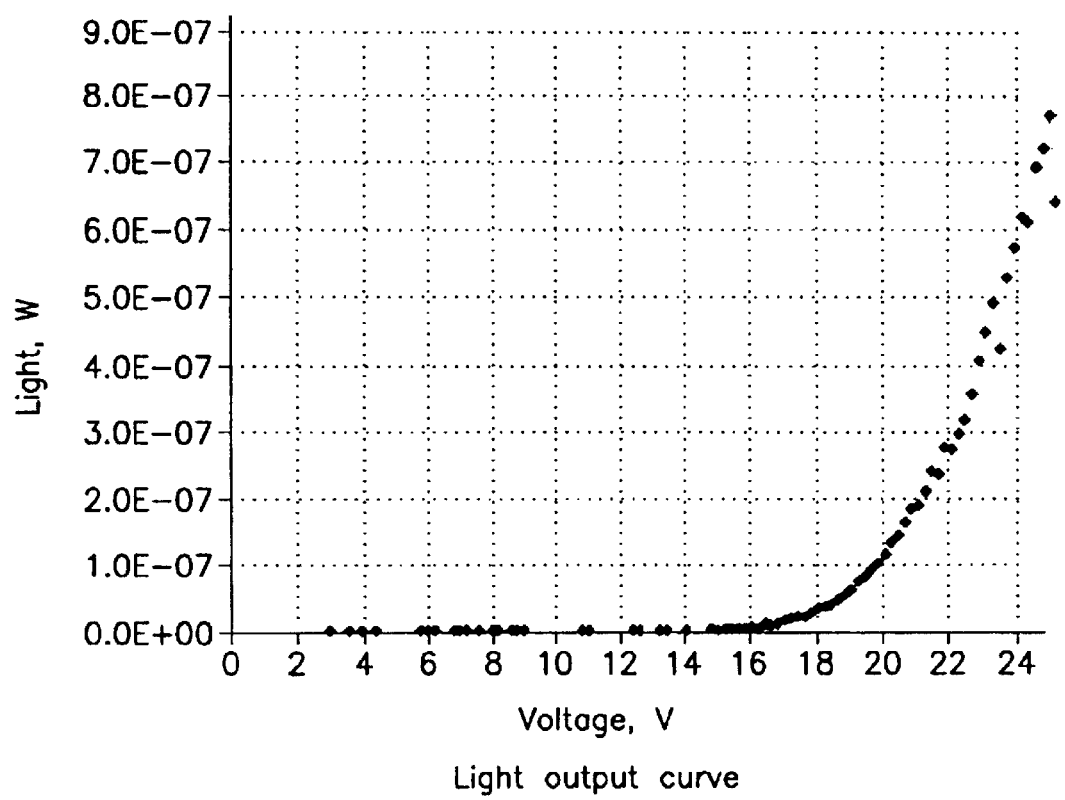
Figure 5:
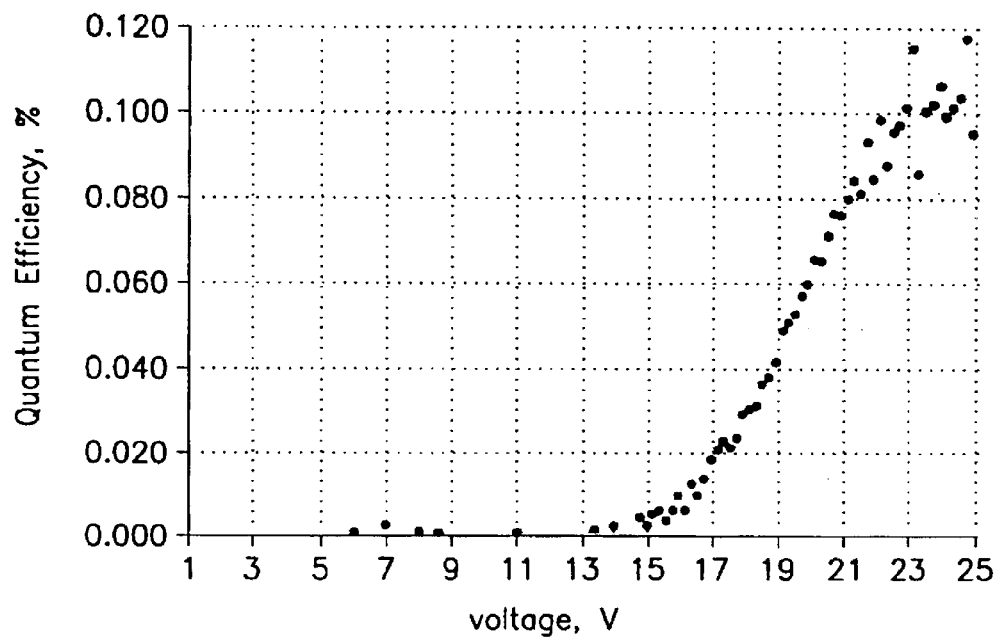
FIG. 5. Quantum efficiency dependence on applied voltage for OLED with $Pt(thpy)_2$ dopant.
Figure 6A:
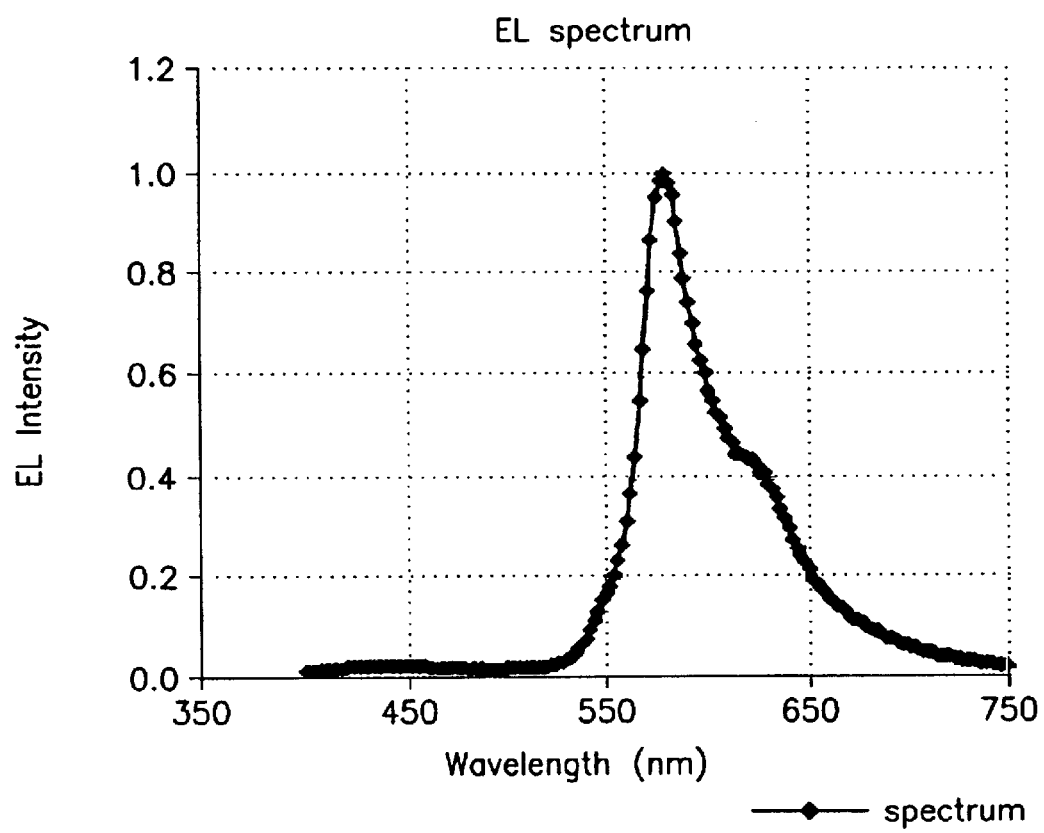
FIG. 6. Characteristics of the OLED device with $Pt(thpy)_2$ dopant: (a) normalized electroluminescence (EL) spectrum of the device at 22 V (b) CIE diagram based on normalized EL spectrum.
Figure 6B:
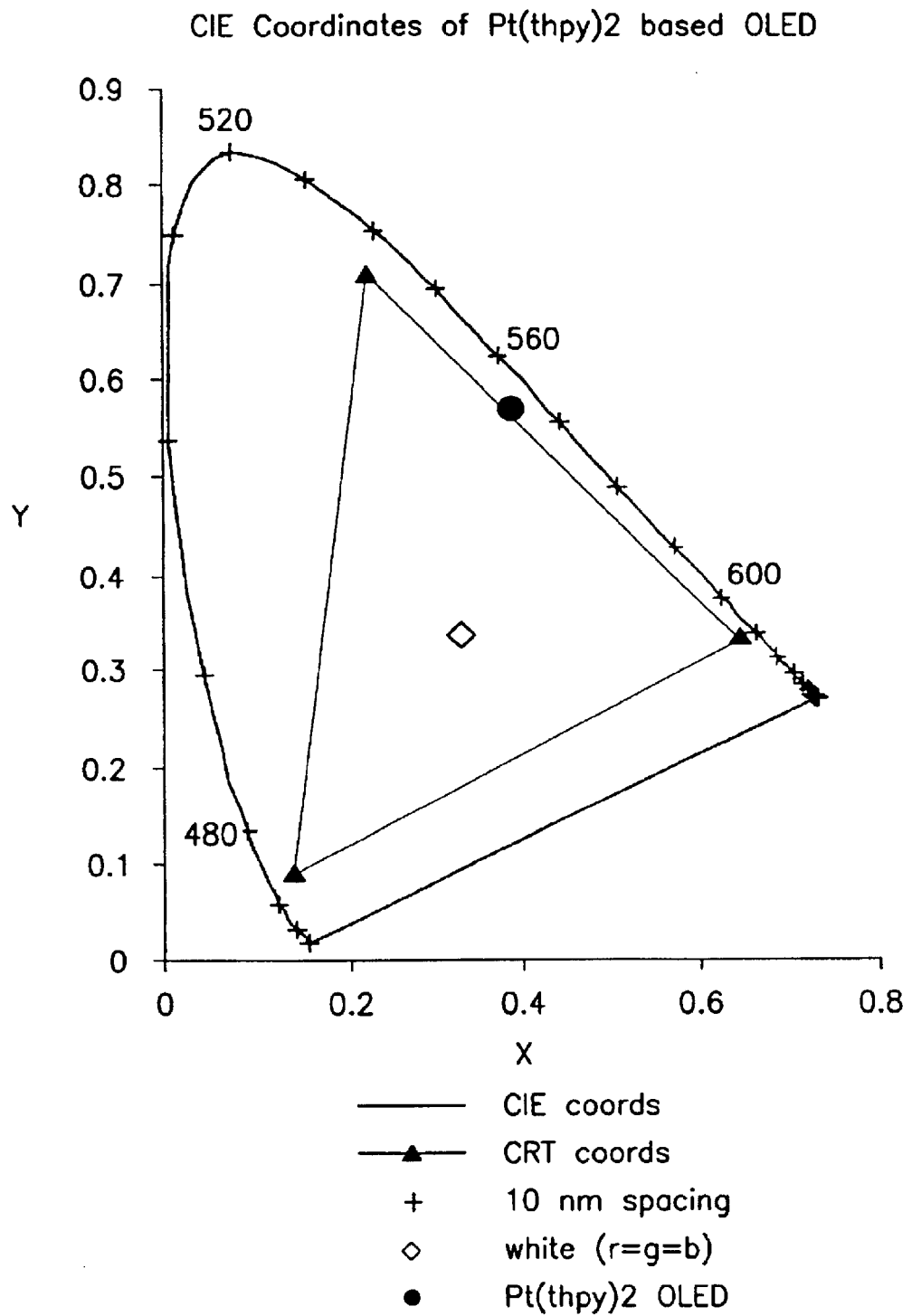

Pt(thpy)$_2$ does not appear to be stable toward sublimation. In order to test it in an OLED we have fabricated a polymer blended OLED with Pt(thpy)$_2$ dopant. The optimal doping level was determined by the photoluminescence study described above. The emission from this device comes exclusively from the Pt(thpy)$_2$ dopant. Typical current-voltage characteristic and light output curve of the device are shown in FIG. 4. Quantum efficiency dependence on applied voltage is demonstrated in FIG. 5. Thus, at 22 V quantum efficiency is ca. 0.11%. The high voltage required to drive this device is a result of the polymer blend OLED structure and not the dopant. Similar device properties were observed for a polymer blend device made with a coumarin dopant in place of Pt(thpy)$_2$. In addition, electroluminescence spectrum and CIE diagram are shown in FIG. 6.

Example 2

In this example, we describe OLEDs employing the green, electrophosphorescent materialfac tris(2-phenylpyridine) iridium (Ir(ppy)$_3$). This compound has the following formulaic representation:

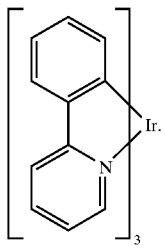

The coincidence of a short triplet lifetime and reasonable photolumine scent efficiency allows Ir(ppy)$_3$-based OLEDs to achieve peak quantum and power efficiencies of 8.0% (28 cd/A) and ~30 lm/W respectively. At an applied bias of 4.3V, the luminance reaches 100 cd/m$^2$ and the quantum and power efficiencies are 7.5% (26 cd/A) and 19 lm/W, respectively.

Figure 7:
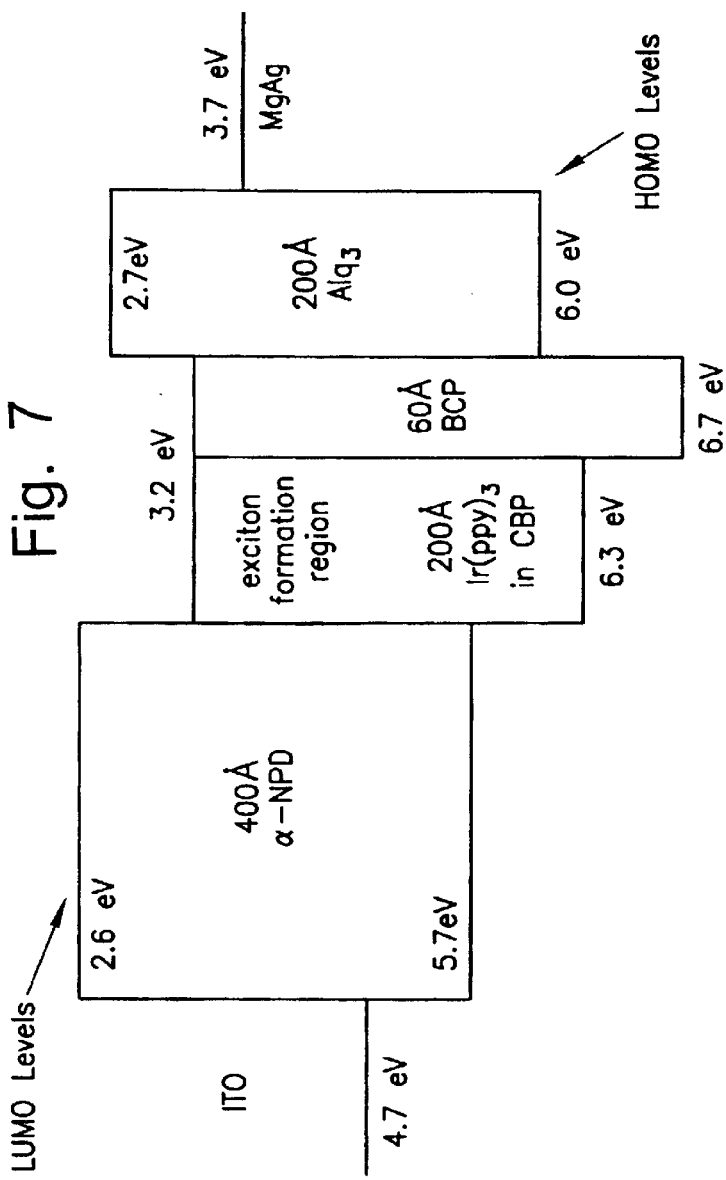
FIG. 7. Proposed energy level structure of the electrophosphorescent device of Example 2. The highest occupied molecular orbital (HOMO) energy and the lowest unoccupied molecular orbital (LUMO) energy are shown (see I. G. Hill and A. Kahn, J. Appl. Physics (1999)). Note that the HOMO and LUMO levels for $Ir(ppy)_3$ are not known. The bottom portion of FIG. 7 shows structural chemical formulae for: (a) $Ir(ppy)_3$; (b) CBP; and (c) BCP.
Figure 7:
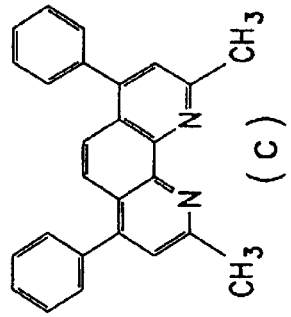
Figure 7:
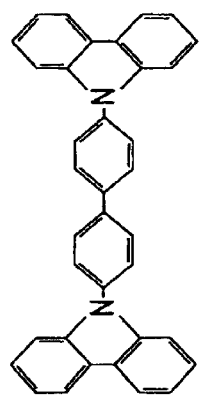
Figure 7:
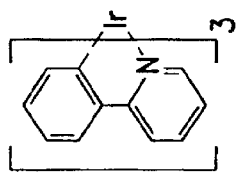

Organic layers were deposited by high vacuum (10$^{-6}$Torr) thermal evaporation onto a cleaned glass substrate precoated with transparent, conductive indium tin oxide. A 400Å thick layer of 4,4'-bis(N-(1-naphthyl)-N-phenyl-amino) biphenyl (α-NPD) is use d to transport holes to the luminescent layer consisting of Ir(ppy)$_3$ in CBP. A 200 Å thick layer of the electron transport material tris-(8-hydroxyquinoline) aluminum (Alq$_3$) is used to transport electrons into the Ir(ppy)$_3$:CBP layer, and to reduce Ir(ppy)$_3$ luminescence absorption at the cathode. A shadow mask with 1 mm diameter openings was used to define the cathode consisting of a 1000 Å thick layer of 25:1 Mg:Ag, with a 500Å thick Ag cap. As previously (O'Brien, et al., App. Phys. Lett. 1999, 74, 442–444), we found that a thin (60Å) barrier layer of 2,9-dimethyl-4,7-diphenyl-1,10-phenanthroline (bathocuproine, or BCP) inserted between the CBP and the Alq$_3$was necess ary to confine excitons within the luminescent zone and hence maintain high efficiencies. In O'Brien et al., Appl. Phys. Lett. 1999, 74, 442–444, it was argued that this layer prevents triplets from diffusing outside of the doped region. It was also suggested that CBP may readily transport holes and that BCP may be required to force exciton formation within the luminescent layer. In either case, the use of BCP clearly serves to trap excitons within the luminescent region. The molecular structural formulae of some of the materials used in the OLEDs, along with a proposed energy level diagram, is shown in FIG. 7.

Figure 8:
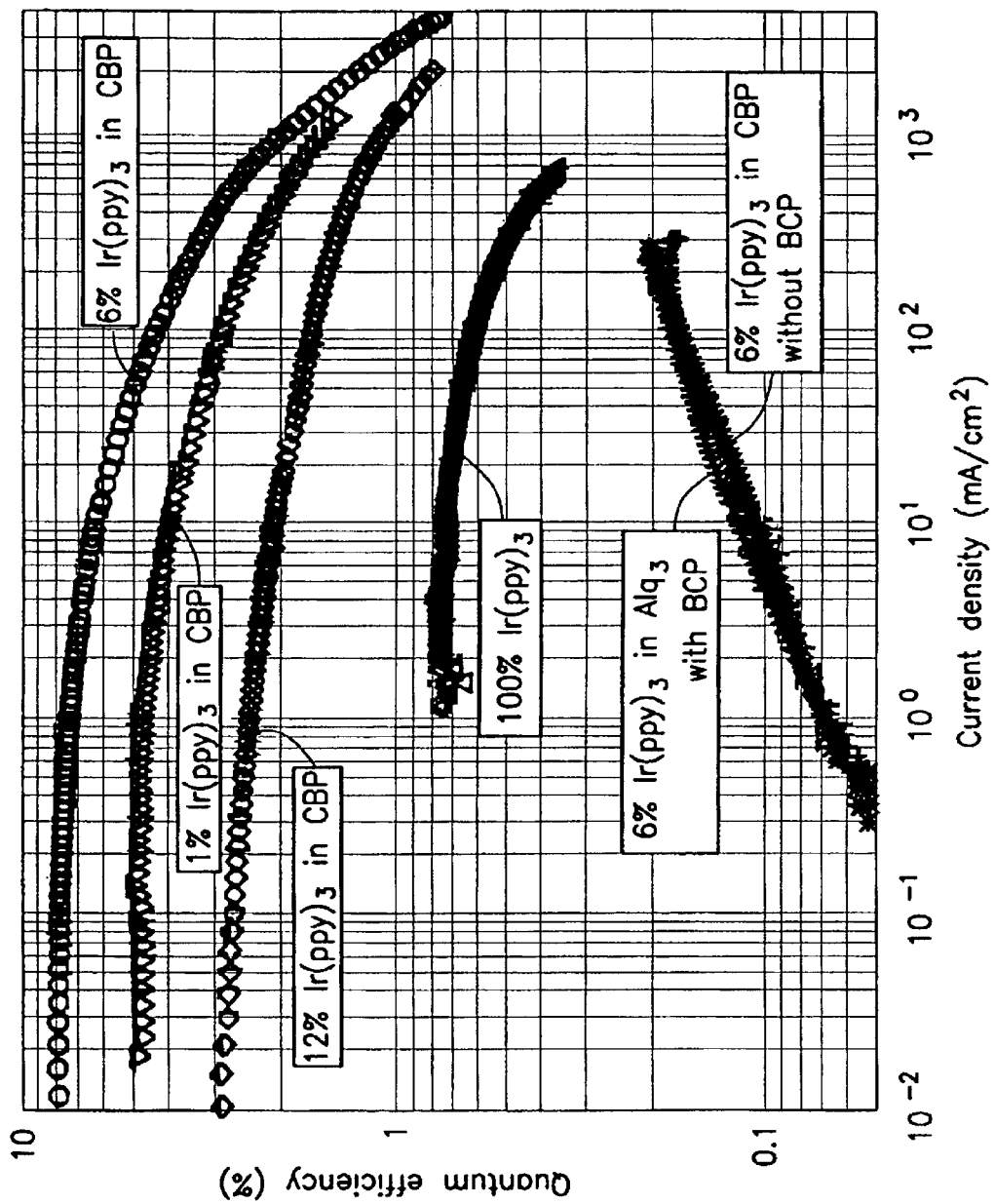
FIG. 8. The external quantum efficiency of OLEDs using $Ir(ppy)_3$ : CBP luminescent layers. Peak efficiencies are observed for a mass ratio of 6% $Ir(ppy)_3$ to CBP. The 100% $Ir(ppy)_3$ device has a slightly different structure than shown in FIG. 7. In it, the $Ir(ppy)_3$ layer is 300 Å thick and there is no BCP blocking layer. The efficiency of a 6% $Ir(ppy)_3$ : CBP device grown without a BCP layer is also shown.

FIG. 8 shows the external quantum efficiencies of several Ir(ppy)$_3$-based OLEDs. The doped structures exhibit a slow decrease in quantum efficiency with increasing current. Similar to the results for the Alq$_3$:PtOEP system the doped devices achieve a maximum efficiency (~8%) for mass ratios of Ir(ppy)$_3$:CBP of approximately 6–8%. Thus, the energy transfer pathway in Ir(ppy)$_3$:CBP is likely to be similar to that in PtOEP:Alq$_3$ (Baldo, et al., Nature, 1998, 395, 151; O'Brien, 1999, op. cit.) i.e. via short range Dexter transfer of triplets from the host. At low Ir(ppy)$_3$ concentrations, the lumophores often lie beyond the Dexter transfer radius of an excited Alq$_3$ molecule, while at high concentrations, aggregate quenching is increased. Note that dipole-dipole (Forster) transfer is forbidden for triplet transfer, and in the PtOEP:Alq$_3$ system direct charge trapping was not found to be significant.

Example 3

In addition to the doped device, we fabricated a heterostructure where the luminescent region was a homogeneous film of Ir(Ppy)$_3$. The reduction in efficiency (to ~0.8% ) of neat Ir(ppy)$_3$ is reflected in the transient decay, which has a lifetime of only ~100 ns, and deviates significantly from mono-exponential behavior. A 6% Ir(ppy)$_3$:CBP device without a BCP barrier layer is also shown together with a 6% Ir(ppy)$_3$:Alq$_3$ device with a BCP barrier layer. Here, very low quantum efficiencies are observed to increase with current. This behavior suggests a saturation of nonradiative sites as excitons migrate into the Alq$_3$, either in the luminescent region or adjacent to the cathode.

Example 4

Figure 9:
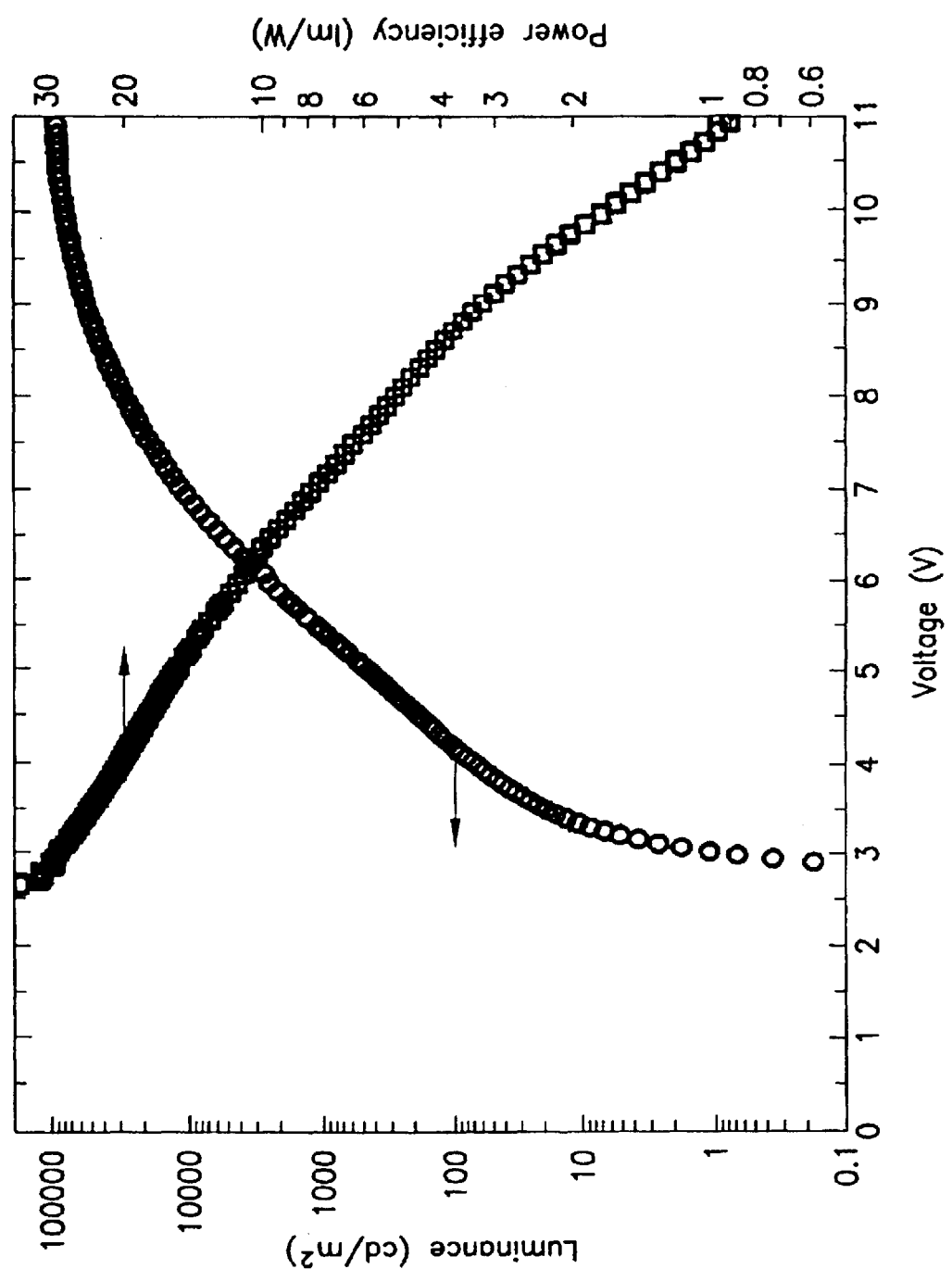
FIG. 9. The power efficiency and luminance of the 6% $Ir(ppy)_3$: CBP device. At 100 cd/m², the device requires 4.3 V and its power efficiency is 19 lm/W.

In FIG. 9 we plot luminance and power efficiency as a function of voltage for the device of Example 2. The peak power efficiency is ~30 lm/W with a quantum efficiency of 8%, (28 cd/A). At 100 cd/m$^2$, a power efficiency of 19 lm/W with a quantum efficiency of 7.5% (26 cd/A) is obtained at a voltage of 4.3V. The transient response of Ir(ppy)$_3$ in CBP is a mono-exponential phosphorescent decay of ~500 ns, compared with a measured lifetime (e.g., King, et al., J. Am. Chem. Soc., 1985, 107, 1431–1432) of 2 μs in degassed toluene at room temperature. These lifetimes are short and indicative of strong spin-orbit coupling, and together with the absence of Ir(ppy)$_3$, fluorescence in the transient response, we expect that Ir(ppy)$_3$ possesses strong intersystem crossing from the singlet to the triplet state. Thus all emission originates from the long lived triplet state. Unfortunately, slow triplet relaxation can form a bottleneck in electrophosphorescence and one principal advantage of Ir(ppy)$_3$ is that it possesses a short triplet lifetime. The phosphorescent bottleneck is thereby substantially loosened. This results in only a gradual decrease in efficiency with increasing current, leading to a maximum luminance of ~100,000 cd/m$^2$.

Example 5

Figure 10:
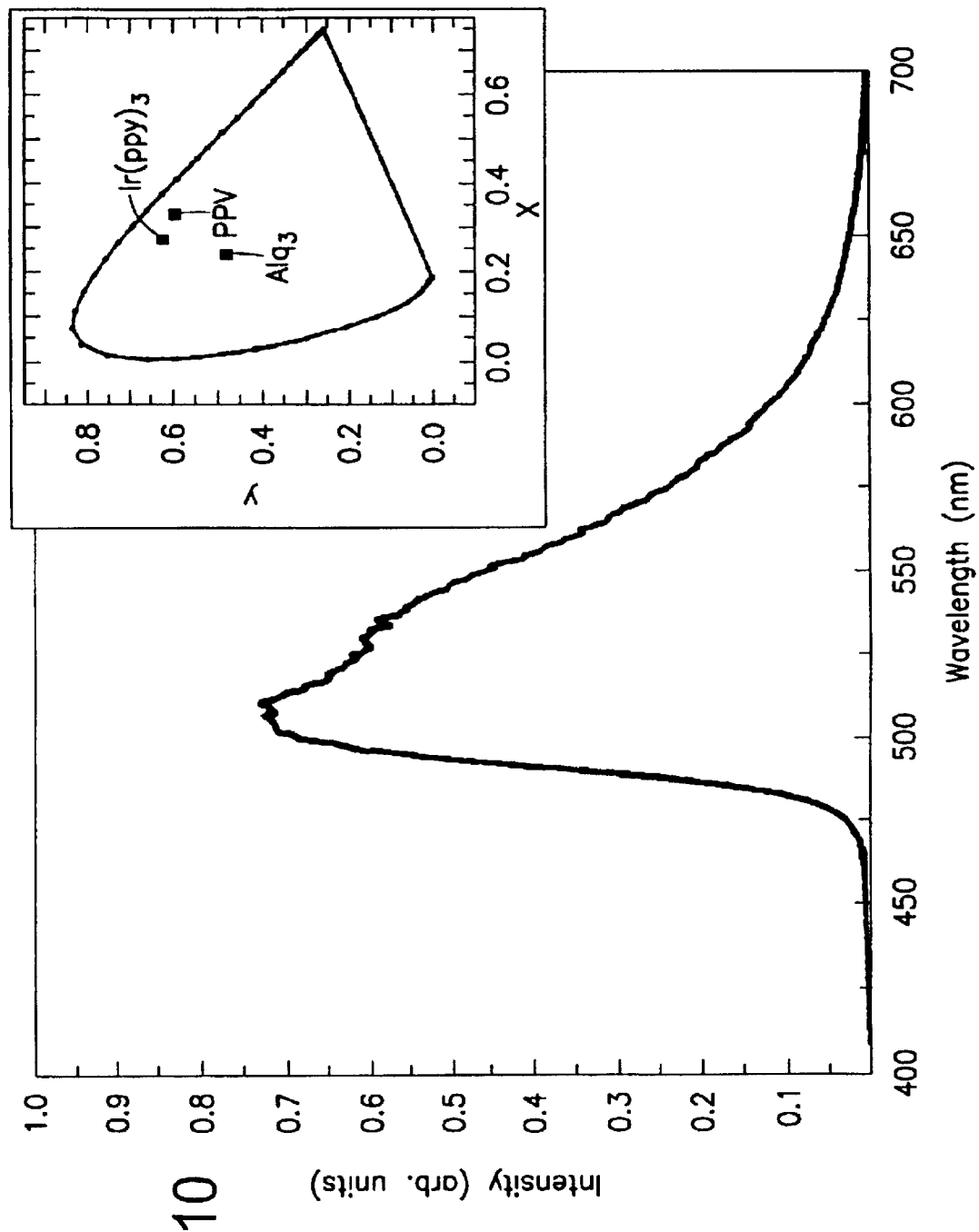
FIG. 10. The electroluminescent spectrum of 6% $Ir(Ppy)_3$: CBP. Inset: The Commission Internationale de L'Eclairage (CIE) chromaticity coordinates of $Ir(ppy)_3$ in CBP are shown relative to fluorescent green emitters $Alq_3$ and poly (p-phenylenevinylene) (PPV).

In FIG. 10, the emission spectrum and Commission Internationale de L'Eclairage (CIE) coordinates of Ir(ppy)$_3$ are shown for the highest efficiency device. The peak wavelength is λ=510 nm and the full width at half maximum is 70 nm. The spectrum and CIE coordinates (x=0.27,y= 0.63) are independent of current. Even at very high current densities (~100 mA/cm$^2$ ) blue emission from CBP is negligible—an indication of complete energy transfer.

Other techniques known to one of ordinary skill may be used in conjunction with the present invention. For example, the use of LiF cathodes (Hung, et al., Appl. Phys. Lett., 1997, 70, 152–154), shaped substrates (G. Gu, et al., Optics Letters, 1997, 22, 396–398), and novel hole transport materials that result in a reduction in operating voltage or increased quantum efficiency (B. Kippelen, et al., MRS (San Francisco, Spring, 1999) are also applicable to this work. These methods have yielded power efficiencies of ~20 lm/W in fluorescent small molecule devices (Kippelen, Id.). The quantum efficiency in these devices (Kido and Iizumi, App. Phys. Lett., 1998, 73, 2721) at 100 cd/m$^2$ is typically ≦4.6% (lower than that of the present invention), and hence greenemitting electrophosphorescent devices with power efficiencies of >40 lm/W can be expected. Purely organic materials (Hoshino and Suzuki, Appl. Phys. Lett., 1996, 69, 224–226) may sometimes possess insufficient spin orbit coupling to show strong phosphorescence at room temperature. While one should not rule out the potential of purely organic phosphors, the preferred compounds may be transition metal complexes with aromatic ligands. The transition metal mixes singlet and triplet states, thereby enhancing intersystem crossing and reducing the lifetime of the triplet excited state.

The present invention is not limited to the emissive molecule of the examples. One of ordinary skill may modify the organic component of the Ir(ppy)$_3$ (directly below) to obtain desirable properties.

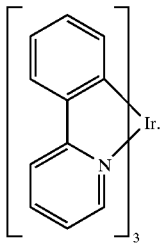

One may have alkyl substituents or alteration of the atoms of the aromatic structure.

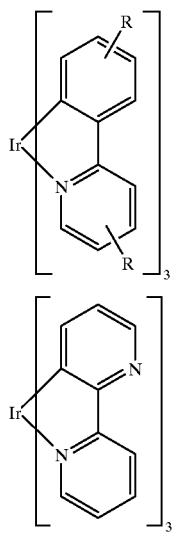

These molecules, related to Ir(ppy)$_3$, can be formed from commercially available ligands. The R groups can be alkyl or aryl and are preferably in the 3, 4, 7 and/or 8 positions on the ligand (for steric reasons). The compounds should give different color emission and may have different carrier transport rates. Thus, the modifications to the basic Ir(ppy)$_3$ structure in the three molecules can alter emissive properties in desirable ways.

Other possible emitters are illustrated below, by way of example.

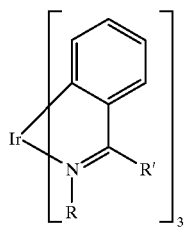

This molecule is expected to have a blue-shifted emission compared to Ir(Ppy)$_3$. R and R' can independently be alkyl or aryl.

Organometallic compounds of osmium may also be used in this invention. Examples include the following.

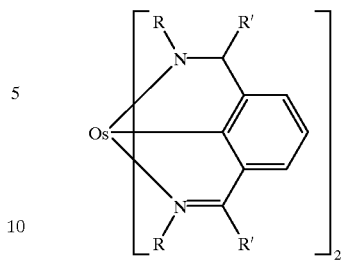

These osmium complexes will be octahedral with 6d electrons (isoelectronic with the Ir analogs) and may have good intersystem crossing efficiency. R and R' are independently selected from the group consisting of alkyl and aryl. They are believed to be unreported in the literature.

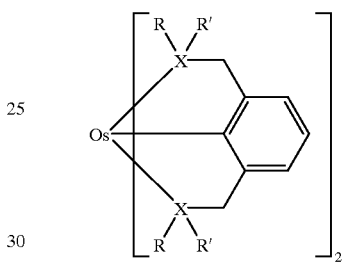

Herein, X can be selected from the group consisting of N or P. R and R' are independently selected from the group alkyl and aryl.

The molecule of the hole-transporting layer of Example 2 is depicted below.

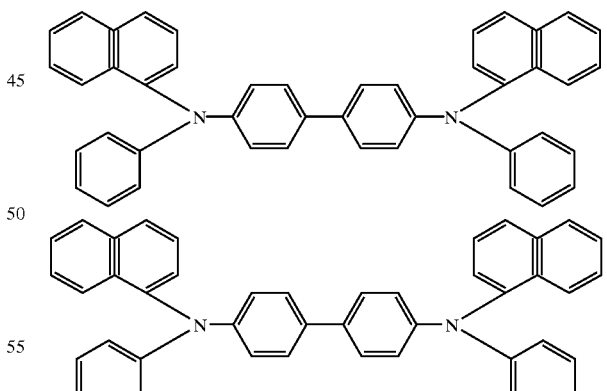

The present invention will work with other hole-transporting molecules known by one of ordinary skill to work in hole transporting layers of OLEDs.

The molecule used as the host in the emissive layer of Example 2 is depicted below.

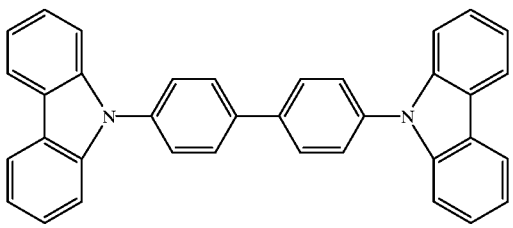

The present invention will work with other molecules known by one of ordinary skill to work as hosts of emissive layers of OLEDs. For example, the host material could be a hole-transporting matrix and could be selected from the group consisting of substituted tri-aryl amines and polyvinylcarbazoles.

The molecule used as the exciton blocking layer of Example 2 is depicted below. The invention will work with other molecules used for the exciton blocking layer, provided they meet the requirements listed in the summary of the invention.

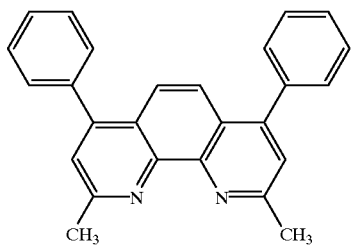

Molecules which are suitable as components for an exciton blocking layer are not necessarily the same as molecules which are suitable for a hole blocking layer. For example, the ability of a molecule to function as a hole blocker depends on the applied voltage, the higher the applied voltage, the less the hole blocking ability. The ability to block excitons is roughly independent of the applied voltage.

Figure 49:
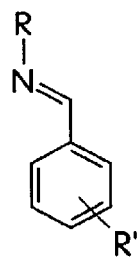
FIG. 49. Other suitable L and X ligands for $L_2MX$ compounds. In all of these ligands listed, one can easily substitute S for O and still have a good ligand.
Figure 49:
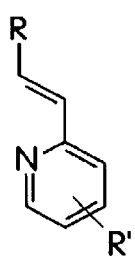
Figure 49:
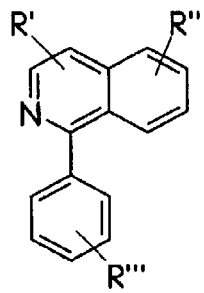
Figure 49:
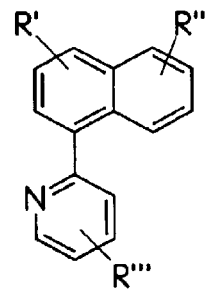
Figure 49:
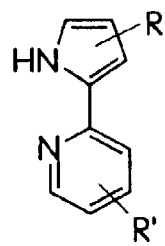
Figure 49:
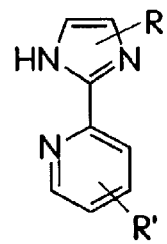
Figure 49:
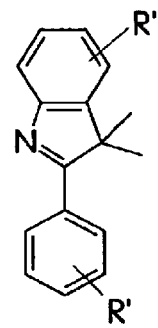
Figure 49:
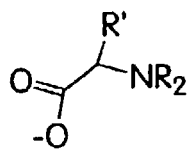
Figure 49:
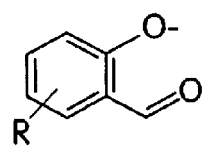
Figure 49:
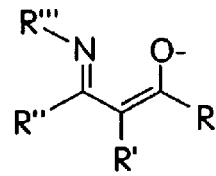
Figure 49:
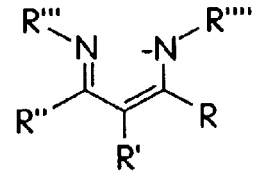
Figure 50:
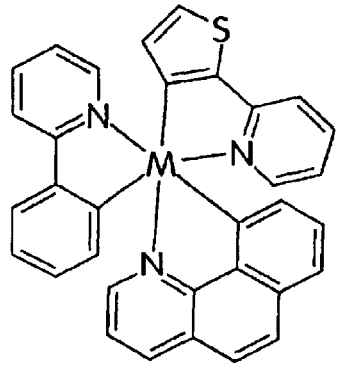
FIG. 50. Examples of L L'L" M compounds. In the listed examples of L L'L" M and L L' M X compounds, the compounds would be expected to emit from the lowest energy ligand or the MLCT state, involving the bq or thpy ligands. In the listed example of an L M X X' compound, emission therefrom is expected from the ppy ligand. The X and X' ligands will modify the physical properties (for example, a hole trapping group could be added to either ligand).
Figure 50:
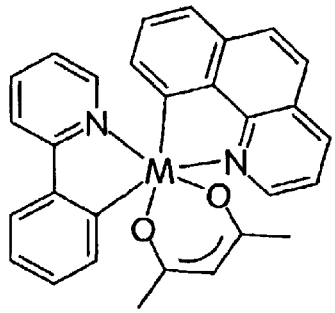
Figure 50:
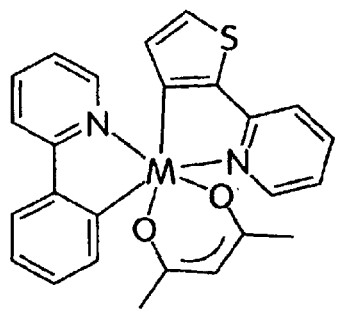
Figure 50:
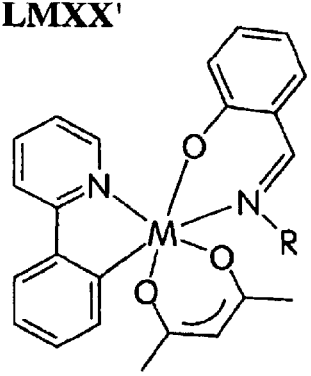

This invention is further directed to the synthesis and use of certain organometallic molecules of formula $L_2MX$ which may be doped into a host phase in an emitter layer of an organic light emitting diode. Optionally, the molecules of formula $L_2MX$ may be used at elevated concentrations or neat in the emitter layer. This invention is further directed to an organic light emitting device comprising an emitter layer comprising a molecule of the formula $L_2MX$ wherein L and X are inequivalent, bidentate ligands and M is a metal, preferably selected from the third row of the transition elements of the periodic table, and most preferably Ir or Pt, which forms octahedral complexes, and wherein the emitter layer produces an emission which has a maximum at a certain wavelength $\lambda_{max}$. The general chemical formula for these molecules which are doped into the host phase is $L_2MX$, wherein M is a transition metal ion which forms octahedral complexes, L is a bidentate ligand, and X is a distinct bidentate ligand. Examples of L are 2-(1-naphthyl) benzoxazole)), (2-phenylbenzoxazole), (2-phenylbenzothiazole), (2-phenylbenzothiazole), (7,8-benzoquinoline), coumarin, (thienylpyridine), phenylpyridine, benzothienylpyridine, 3-methoxy-2-phenylpyridine, thienylpyridine, and tolylpyridine. Examples of X are acetylacetonate ("acac"), hexafluoroacetylacetonate, salicylidene, picolinate, and 8-hydroxyquinolinate. Further examples of L and X are given in FIG. 49 and still further examples of L and X may be found in Comprehensive Coordination Chemistry, Volume 2, G. Wilkinson (editor-in-chief), Pergamon Press, especially in chapter 20.1 (beginning at page 715) by M. Calligaris and L. Randaccio and in chapter 20.4 (beginning at page 793) by R. S. Vagg.

Synthesis of Molecules of Formula $L_2MX$

The compounds of formula $L_2MX$ can be made according to the reaction:

$$L_2M(\mu\text{-Cl})_2ML_2 + XH \rightarrow L_2MX + HCl$$

wherein $L_2M(\mu\text{-Cl})_2ML_2$ is a chloride bridged dimer with L a bidentate ligand, and M a metal such as Ir; XH is a Bronsted acid which reacts with bridging chloride and serves to introduce a bidentate ligand X, wherein XH can be, for example, acetylacetone, hexafluoroacetylacetone, 2-picolinic acid, or N-methylsalicylanilide; and $L_2MX$ has approximate octahedral disposition of the bidentate ligands L, L, and X about M.

$L_2Ir(\mu\text{-Cl})_2IrL_2$ complexes were prepared from $IrCl_3 \cdot nH_2O$ and the appropriate ligand by literature procedures (S. Sprouse, K. A. King, P. J. Spellane, R. J. Watts, J. Am. Chem. Soc., 1984, 106, 6647–6653; for general reference: G. A. Carlson, et al., Inorg. Chem., 1993, 32, 4483; B. Schmid, et al., Inorg. Chem., 1993, 33, 9; F. Garces, et al.; Inorg. Chem., 1988, 27, 3464; M. G. Colombo, et al., Inorg. Chem., 1993, 32, 3088; A. Mamo, et al., Inorg. Chem., 1997, 36, 5947; S. Serroni, et al.; J. Am. Chem. Soc., 1994, 116, 9086; A. P. Wilde, et al., J. Phys. Chem., 1991, 95, 629; J. H. van Diemen, et al., Inorg. Chem., 1992, 31, 3518; M. G. Colombo, et al., Inorg. Chem., 1994, 33, 545), as described below.

Figure 17:
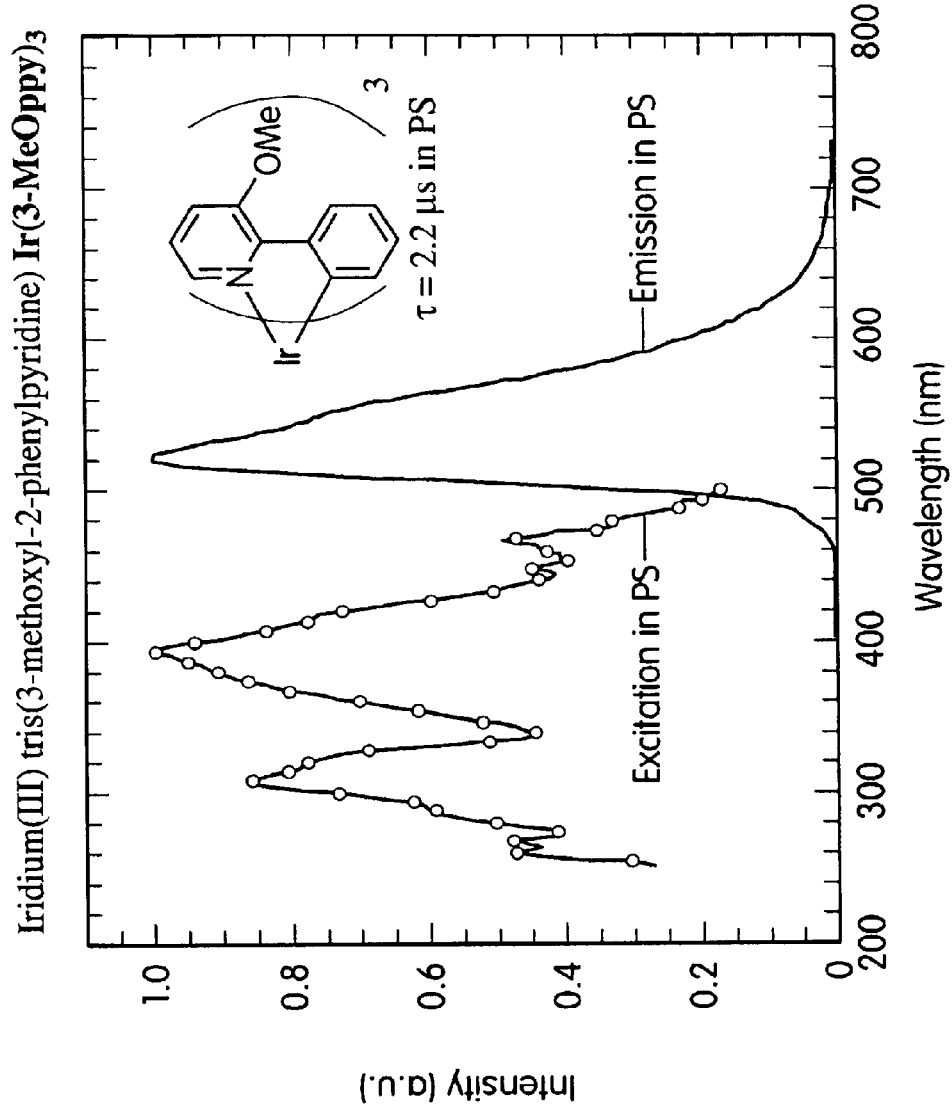
FIG. 17. Emission spectrum of $Ir(3-MeOppy)_3$.
Figure 18:
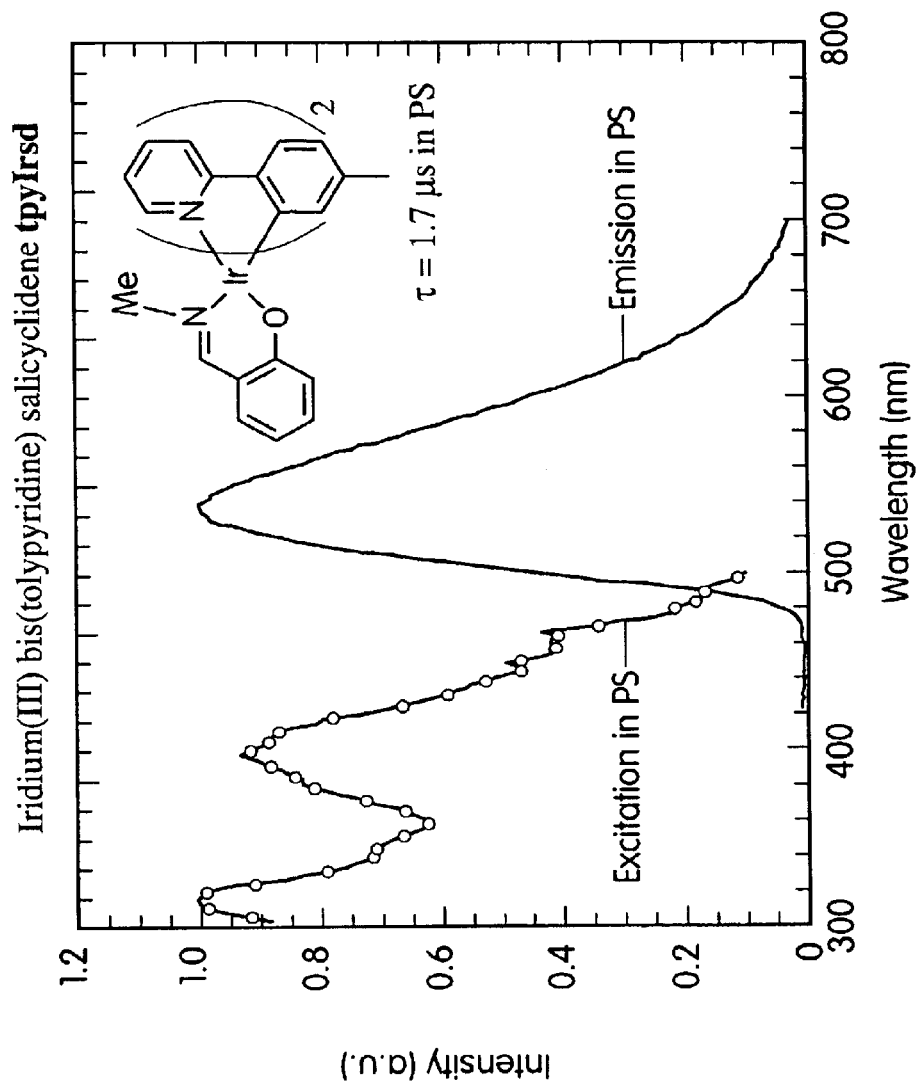
FIG. 18. Emission spectrum of tpyIrsd.
Figure 19:
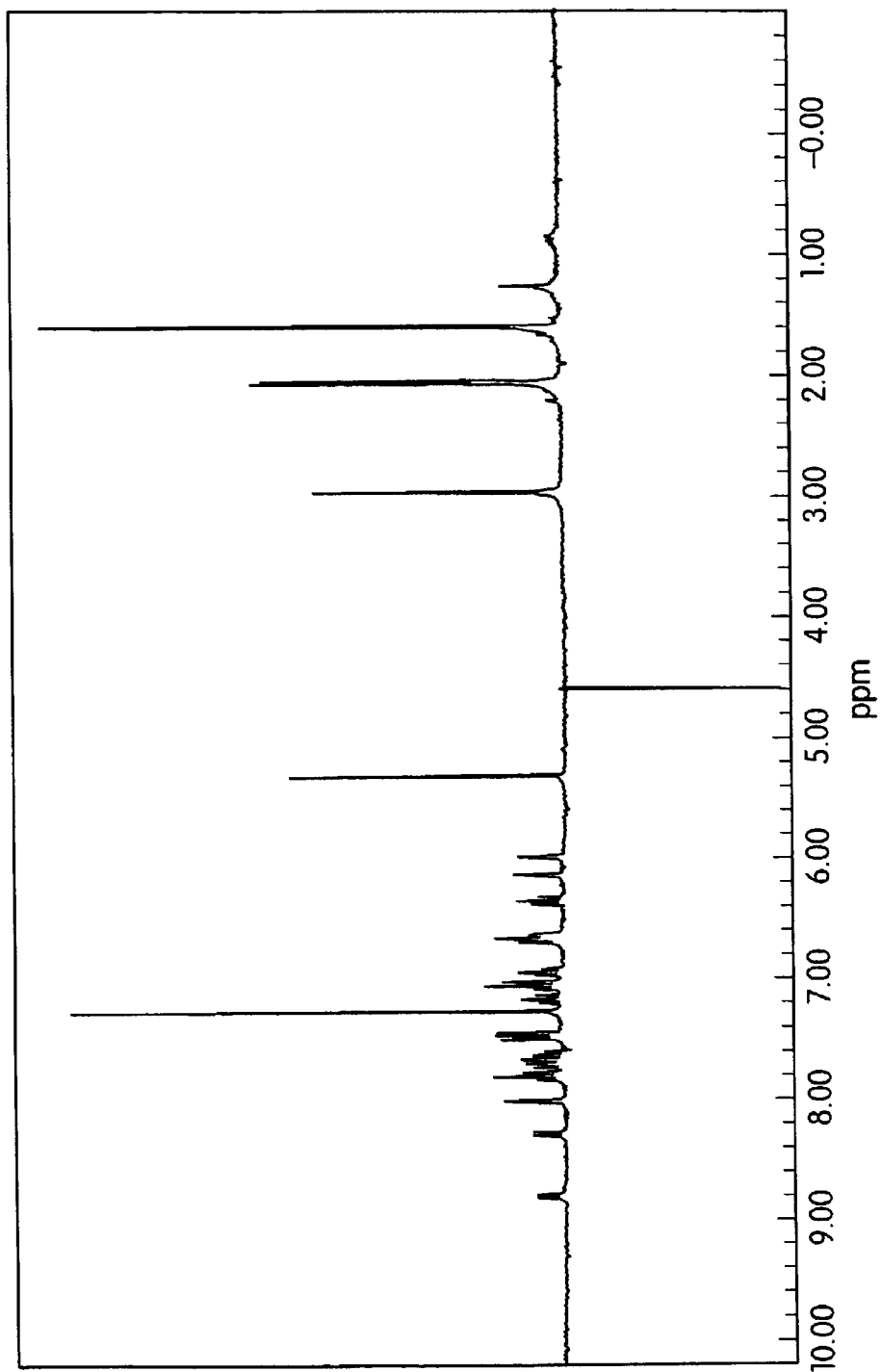
FIG. 19. Proton NMR spectrum of tpyIrsd (=typIrsd).
Figure 20:
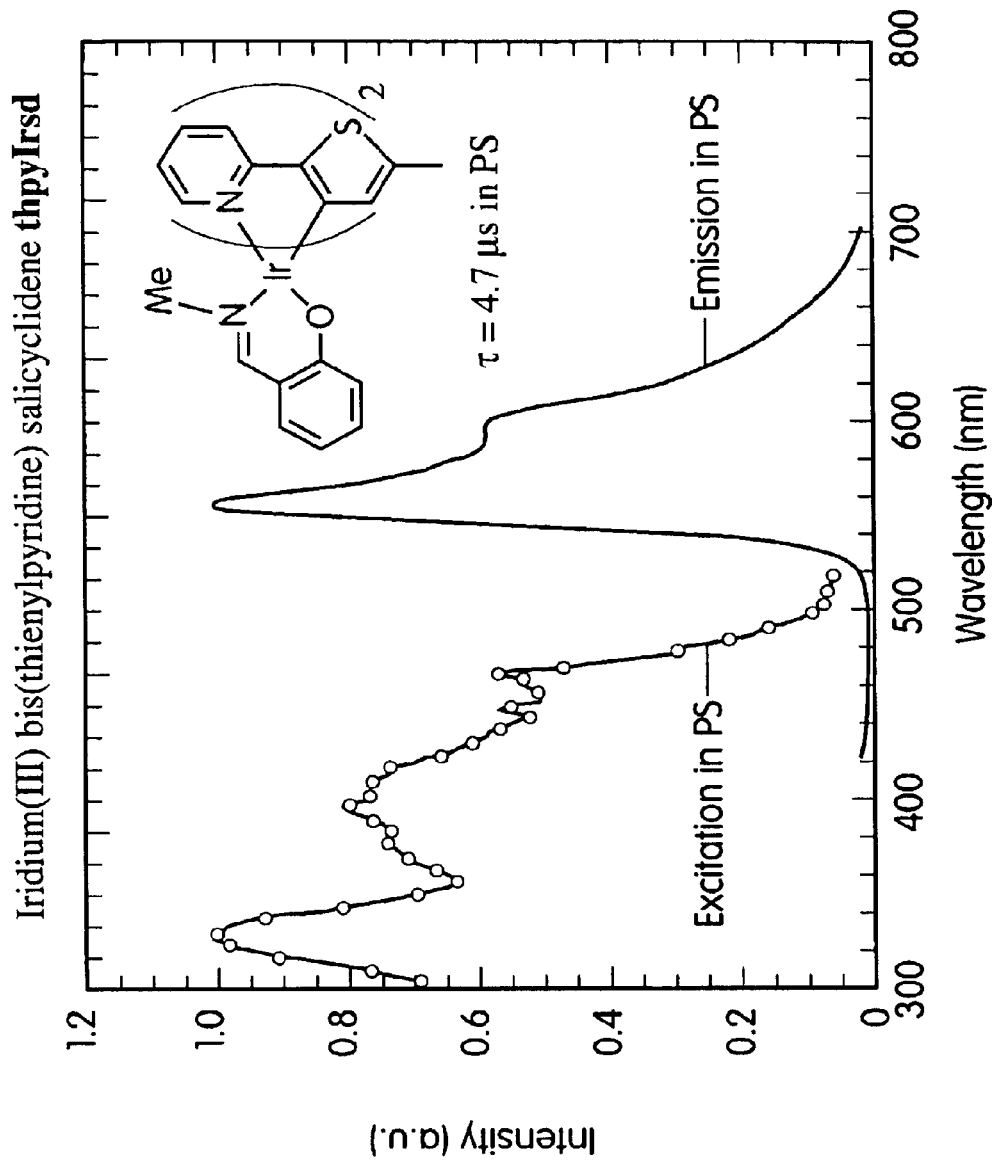
FIG. 20. Emission spectrum of thpyIrsd.
Figure 21:
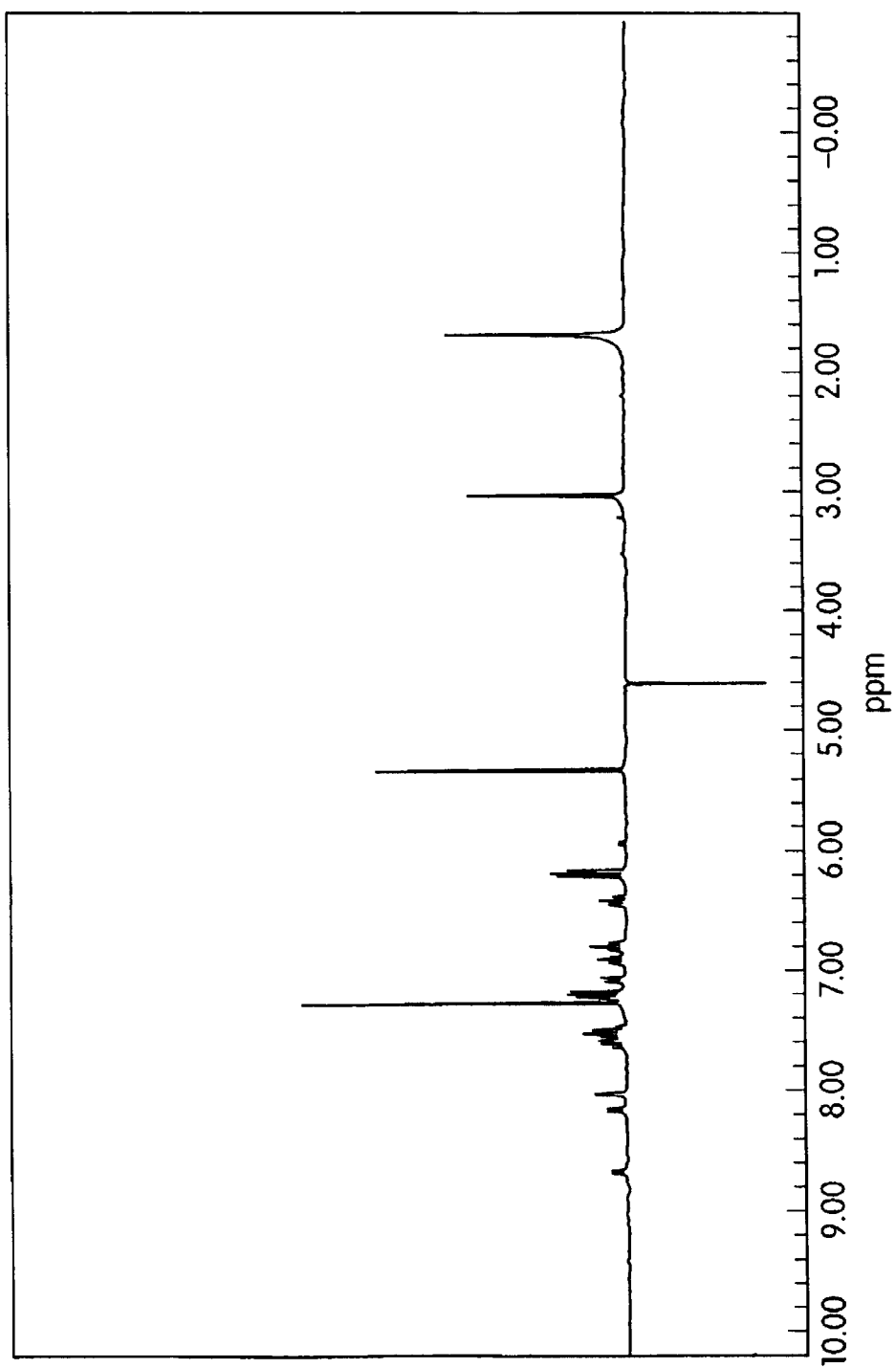
FIG. 21. Proton NMR spectrum of thpyIrsd.
Figure 22:
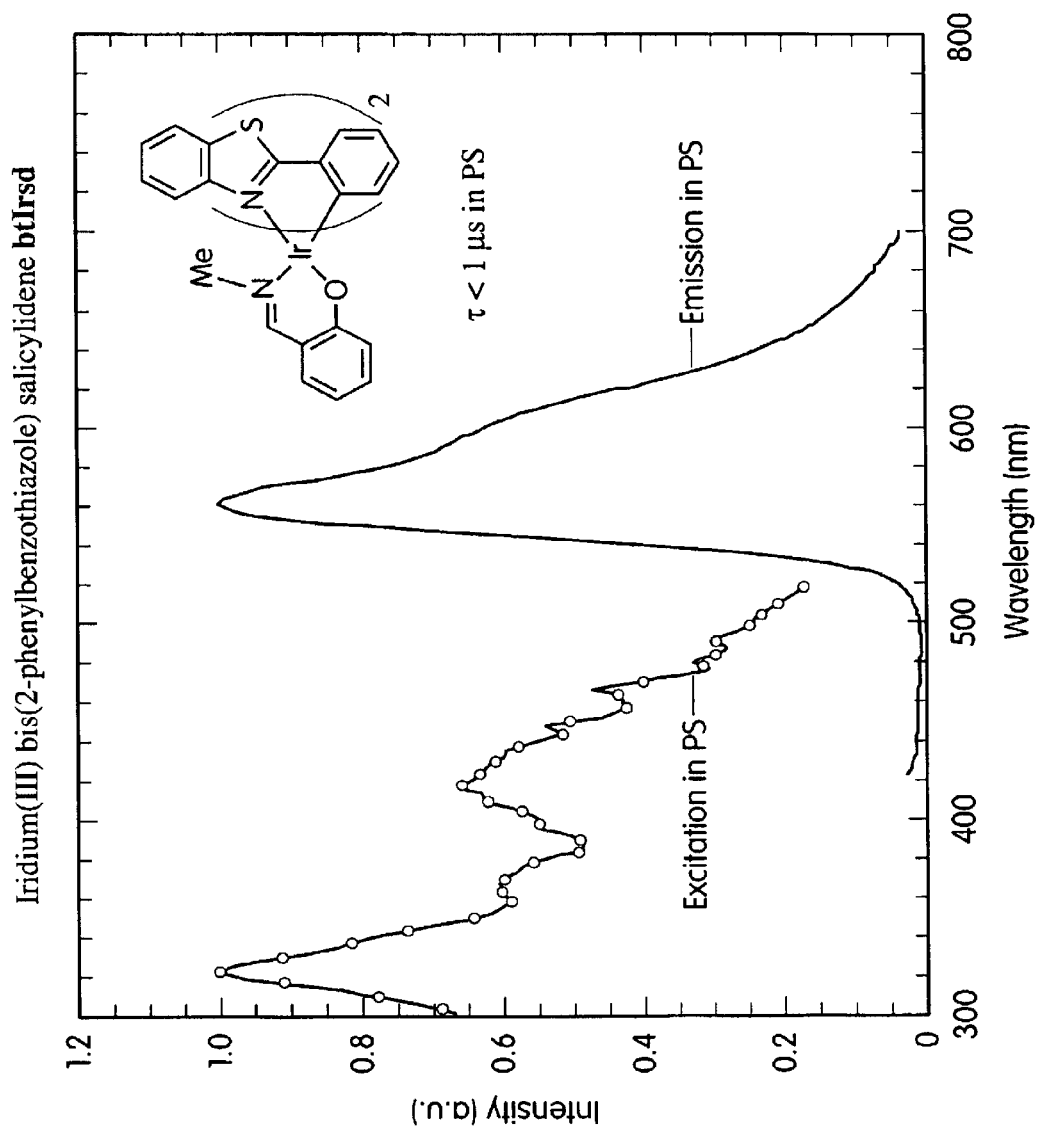
FIG. 22. Emission spectrum of btIrsd.
Figure 23:
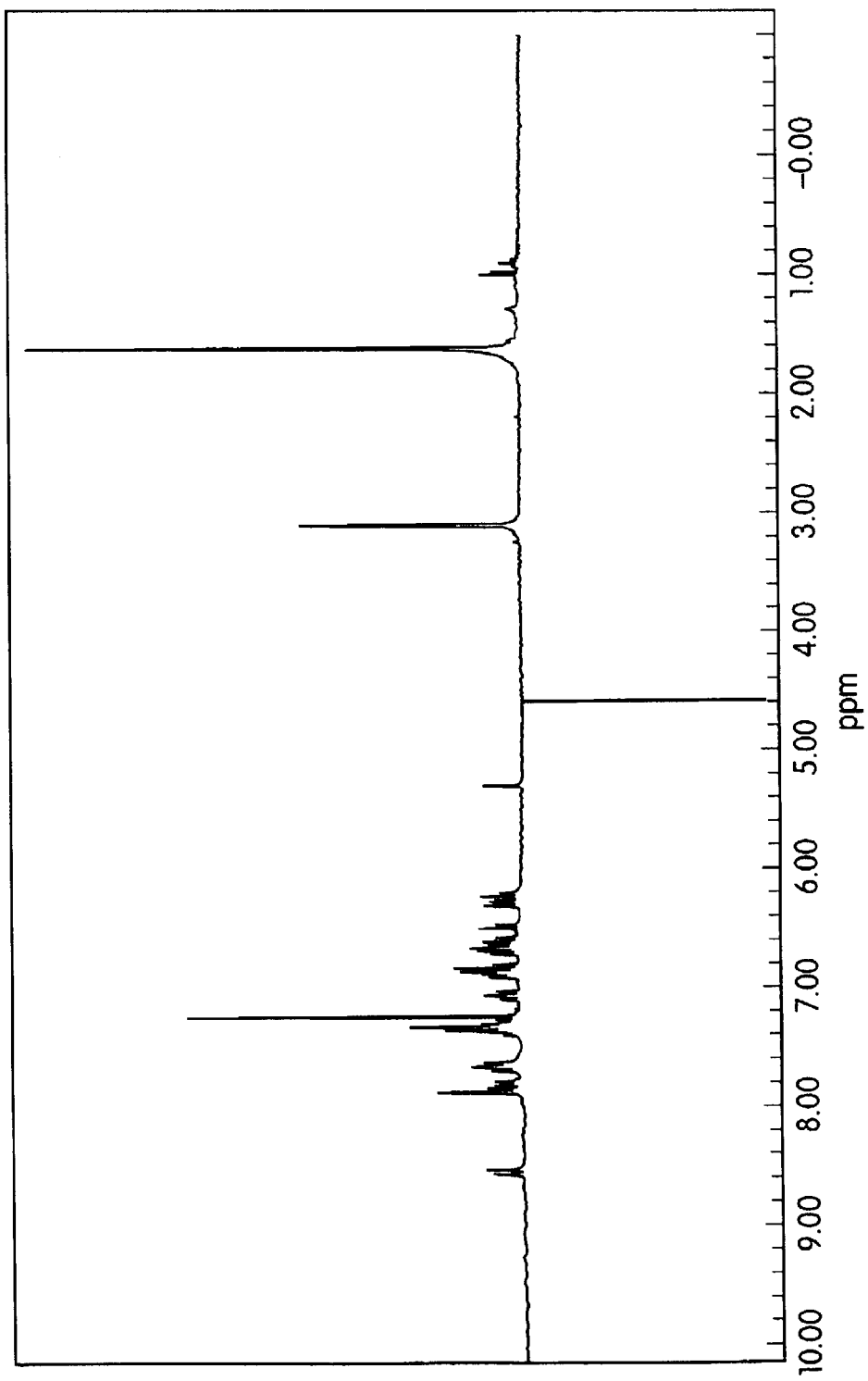
FIG. 23. Proton NMR spectrum of btIrsd.

Ir(3-MeOppy)$_3$. Ir(acac)$_3$ (0.57 g, 1.17 mmol) and 3-methoxy-2-phenylpyridine (1.3 g, 7.02 mmol) were mixed in 30 ml of glycerol and heated to 200° C. for 24 hrs under $N_2$. The resulting mixture was added to 100 ml of 1 M HCl. The precipitate was collected by filtration and purified by column chromatography using $CH_2Cl_2$ as the eluent to yield the product as bright yellow solids (0.35 g, 40%). MS (EI): m/z (relative intensity) 745 (M$^+$, 100), 561 (30), 372 (35). Emission spectrum in FIG. 17.

tpyIrsd. The chloride bridge dimer (tpyIrCl)$_2$ (0.07 g, 0.06 mmol), salicylidene (0.022 g, 0.16 mmol) and $Na_2CO_3$ (0.02 g, 0.09 mmol) were mixed in 10 ml of 1,2-dichloroethane and 2 ml of ethanol. The mixture was refluxed under $N_2$ for 6 hrs or until no dimer was revealed by TLC. The reaction was then cooled and the solvent evaporated. The excess salicylidene was removed by gentle heating under vacuum. The residual solid was redissolved in $CH_2Cl_2$ and the insoluble inorganic materials were removed by filtration. The filtrate was concentrated and column chromatographed using $CH_2Cl_2$ as the eluent to yield the product as bright yellow solids (0.07 g, 85%). MS (EI): m/z (relative intensity) 663 (M$^+$, 75), 529 (100), 332 (35). The emission spectrum is in FIG. 18 and the proton NMR spectrum is in FIG. 19.

thpyIrsd. The chloride bridge dimer (thpyIrCl)$_2$ (0.21 g, 0.19 mmol) was treated the same way as (tpyIrCl)$_2$. Yield: 0.21 g, 84%. MS (EI): m/z (relative intensity) 647 (M$^+$, 100), 513 (30), 486 (15), 434 (20), 324 (25). The emission spectrum is in FIG. 20 and the proton NMR spectrum is in FIG. 21.

btIrsd. The chloride bridge dimer (btIrCl)$_2$ (0.05 g, 0.039 mmol) was treated the same way as (tpyIrCl)$_2$. Yield: 0.05 g, 86%. MS (EI): m/z (relative intensity) 747 (M$^+$, 100), 613 (100), 476 (30), 374 (25), 286 (32). The emission spectrum is in FIG. 22 and the proton NMR spectrum is in FIG. 23.

Figure 24:
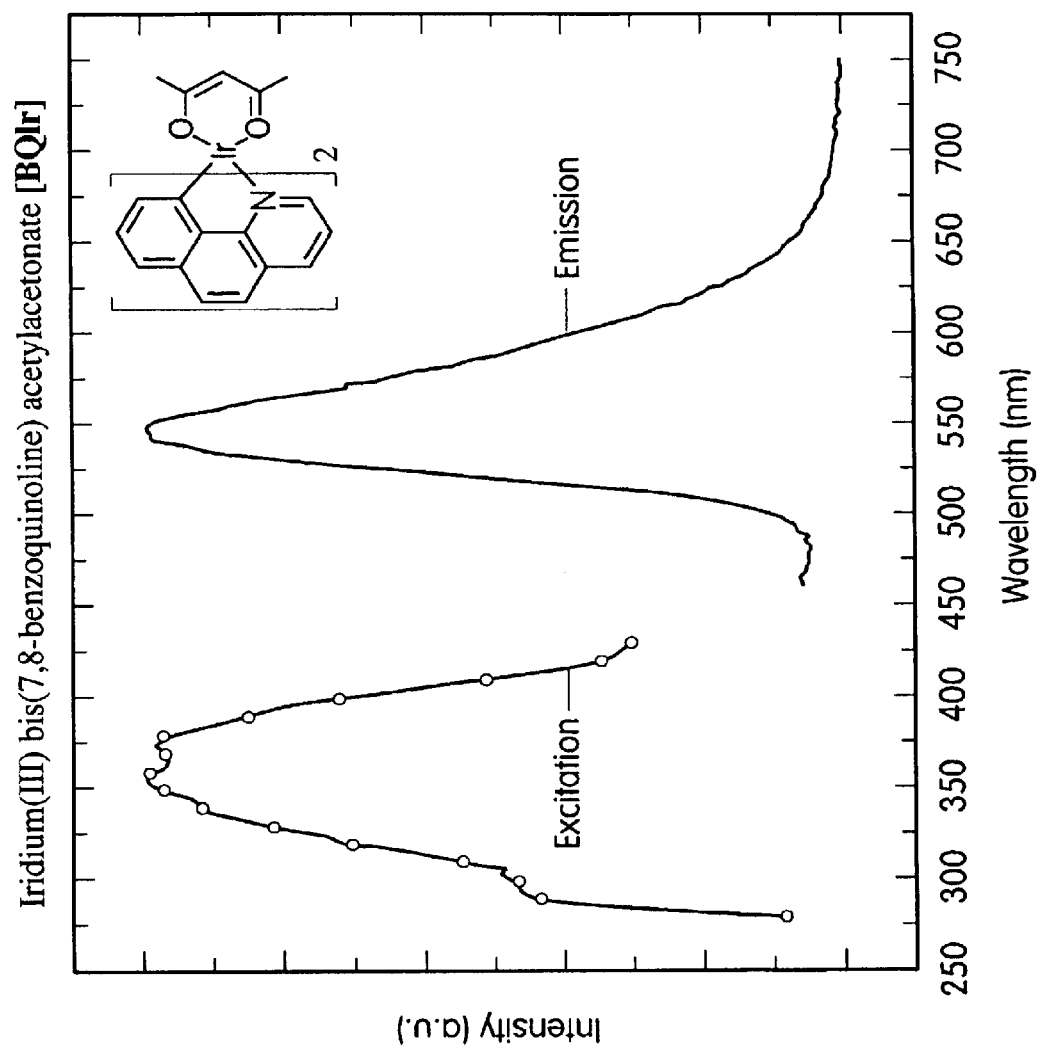
FIG. 24. Emission spectrum of BQIr.
Figure 25:
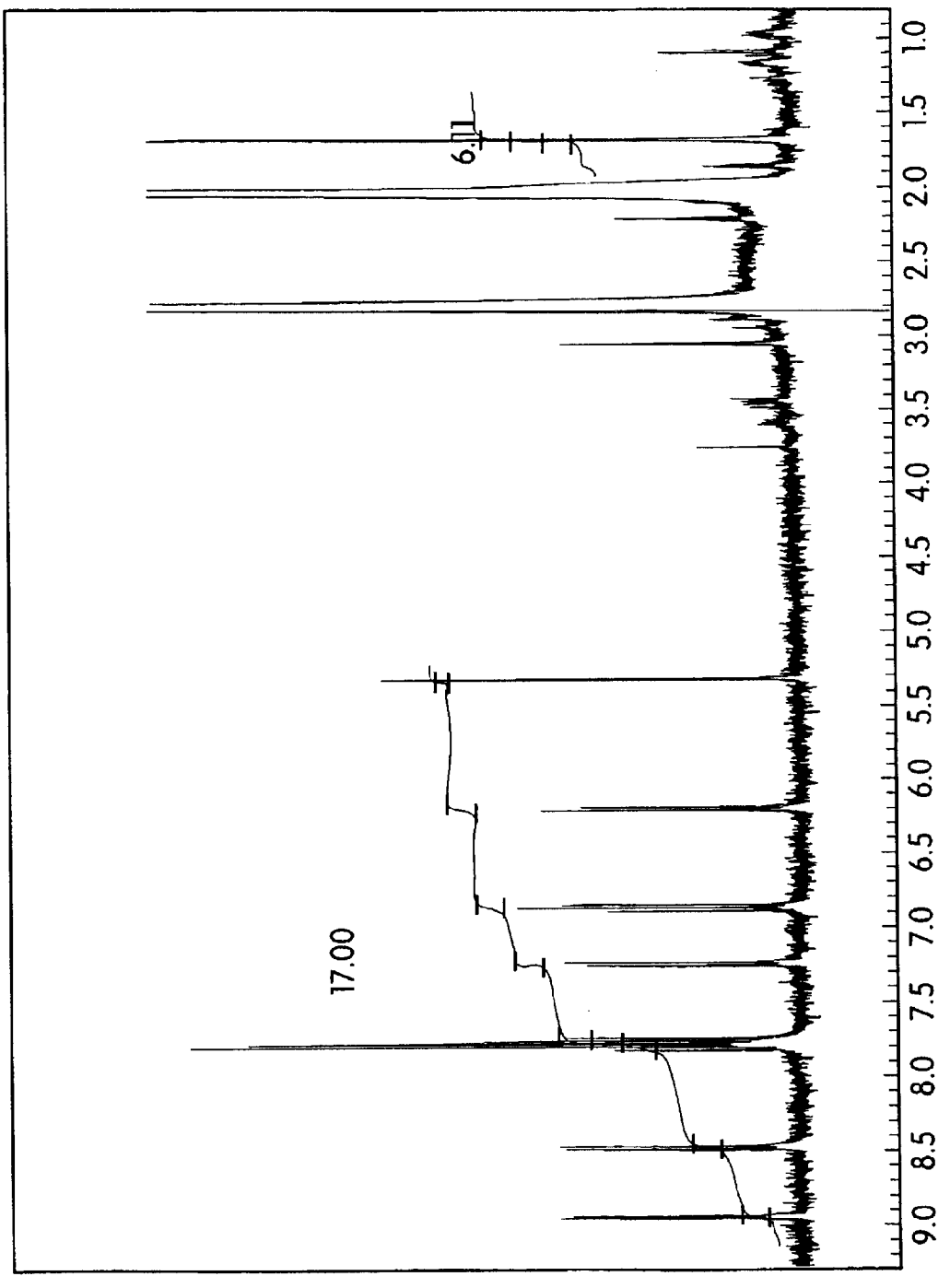
FIG. 25. Proton NMR spectrum of BQIr.

Ir(bq)$_2$(acac), BQIr. The chloride bridged dimer (Ir(bq)$_2$Cl)$_2$ (0.091 g, 0.078 mmol), acetylacetone (0.021 g) and sodium carbonate (0.083 g) were mixed in 10 ml of 2-ethoxyethanol. The mixture was refluxed under N$_2$ for 10 hrs or until no dimer was revealed by TLC. The reaction was then cooled and the yellow precipitate filtered. The product was purified by flash chromatography using dichloromethane. Product: bright yellow solids (yield 91%). $^1$H NMR (360 MHz, acetone-d$_6$), ppm: 8.93 (d,2H), 8.47 (d,2H), 7.78 (m,4H), 7.25 (d,2H), 7.15 (d,2H), 6.87 (d,2H), 6.21 (d,2H), 5.70 (s,1H), 1.63 (s,6H). MS, e/z: 648 (M+,80%), 549 (100%). The emission spectrum is in FIG. 24 and the proton NMR spectrum is in FIG. 25.

Figure 26:
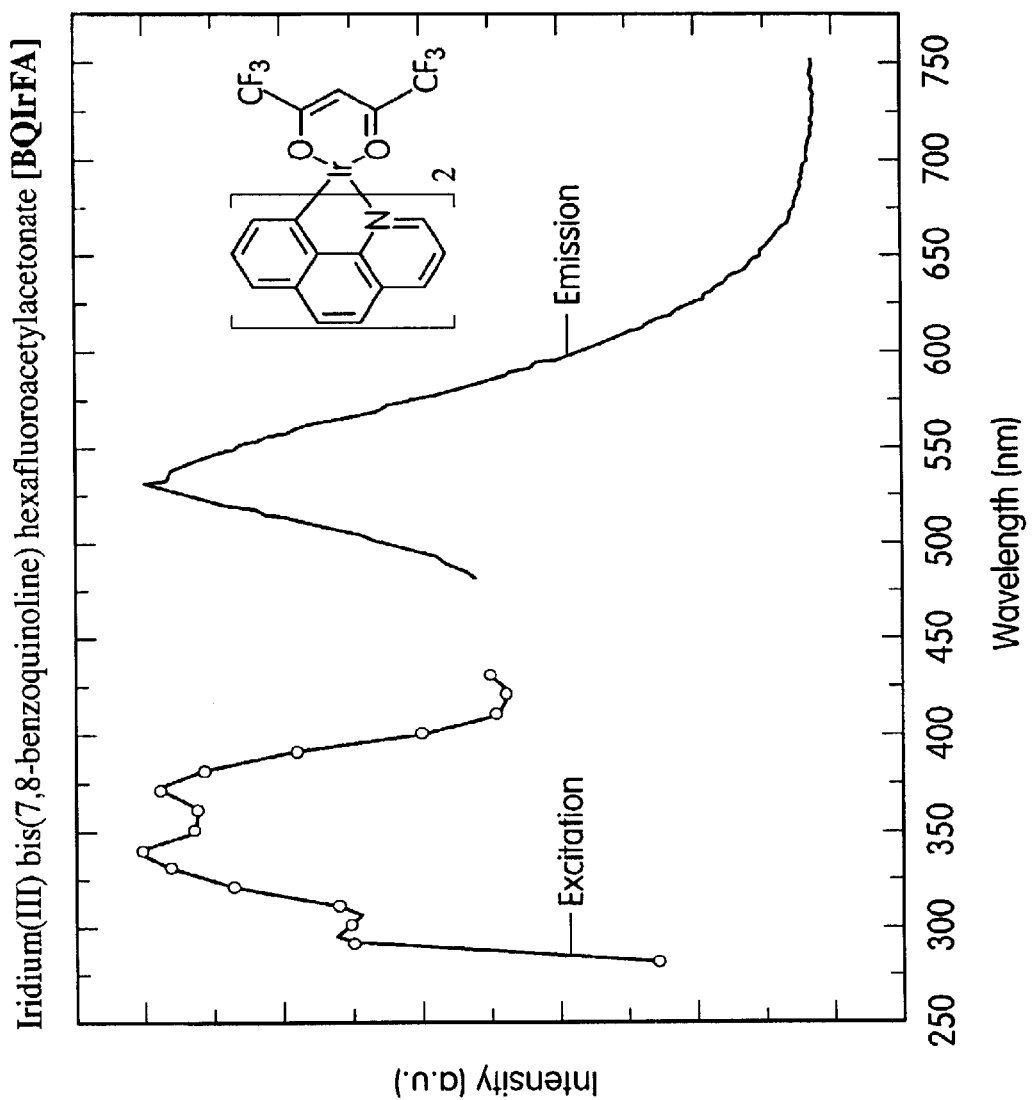
FIG. 26. Emission spectrum of BQIrFA.

Ir(bq)$_2$(Facac), BQIrFA. The chloride bridged dimer (Ir(bq)$_2$Cl)$_2$ (0.091 g, 0.078 mmol), hexafluoroacetylacetone (0.025 g) and sodium carbonate (0.083 g) were mixed in 10 ml of 2-ethoxyethanol. The mixture was refluxed under N$_2$ for 10 hrs or until no dimer was revealed by TLC. The reaction was then cooled and the yellow precipitate filtered. The product was purified by flash chromatography using dichloromethane. Product: yellow solids (yield 69%). $^1$H NMR (360 MHz, acetone-d$_6$), ppm: 8.99 (d,2H), 8.55 (d,2H), 7.86 (m,4H), 7.30 (d,2H), 7.14 (d,2H), 6.97 (d,2H), 6.13 (d,2H), 5.75 (s,1H). MS, e/z: 684 (M+,59%), 549 (100%). Emission spectrum in FIG. 26.

Figure 27:
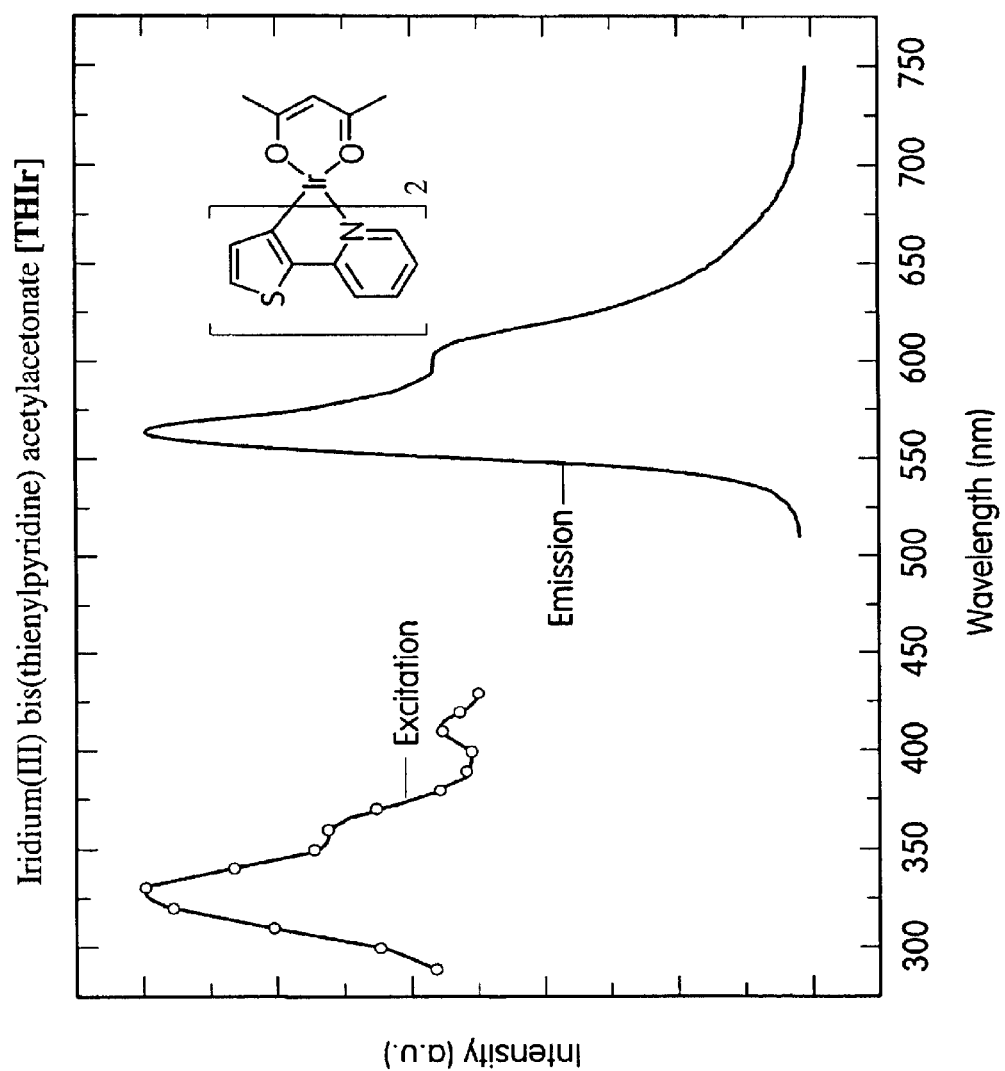
FIG. 27. Emission spectrum of THIr (=thpy; THPIr).
Figure 28:
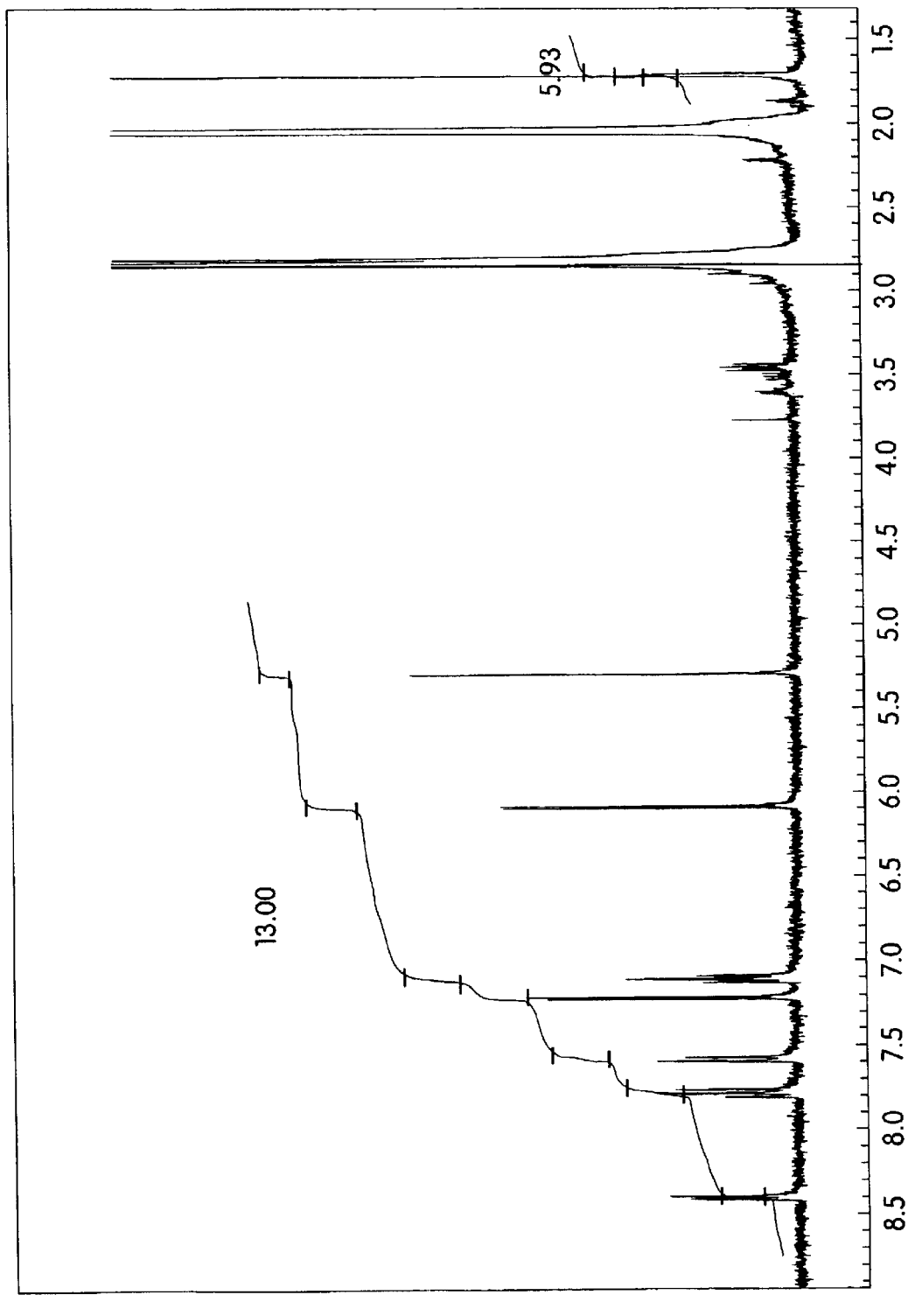
FIG. 28. Proton NMR spectrum of THPIr.

Ir(thpy)$_2$(acac), THPIr. The chloride bridged dimer (Ir(thpy)$_2$Cl)$_2$ (0.082 g, 0.078 mmol), acetylacetone (0.025 g) and sodium carbonate (0.083 g) were mixed in 10 ml of 2-ethoxyethanol. The mixture was refluxed under N$_2$ for 10 hrs or until no dimer was revealed by TLC. The reaction was then cooled and the yellow precipitate filtered. The product was purified by flash chromatography using dichloromethane. Product: yellow-orange solid (yield 80%). $^1$H NMR (360 MHz, acetone-d$_6$), ppm: 8.34 (d,2H), 7.79 (m,2H), 7.58 (d,2H), 7.21 (d,2H), 7.15 (d,2H), 6.07 (d,2H), 5.28 (s,1H), 1.70 (s,6H). MS, e/z: 612 (M+,89%), 513 (100%). The emission spectrum is in FIG. 27 (noted "THIr") and the proton NMR spectrum is in FIG. 28.

Figure 29:
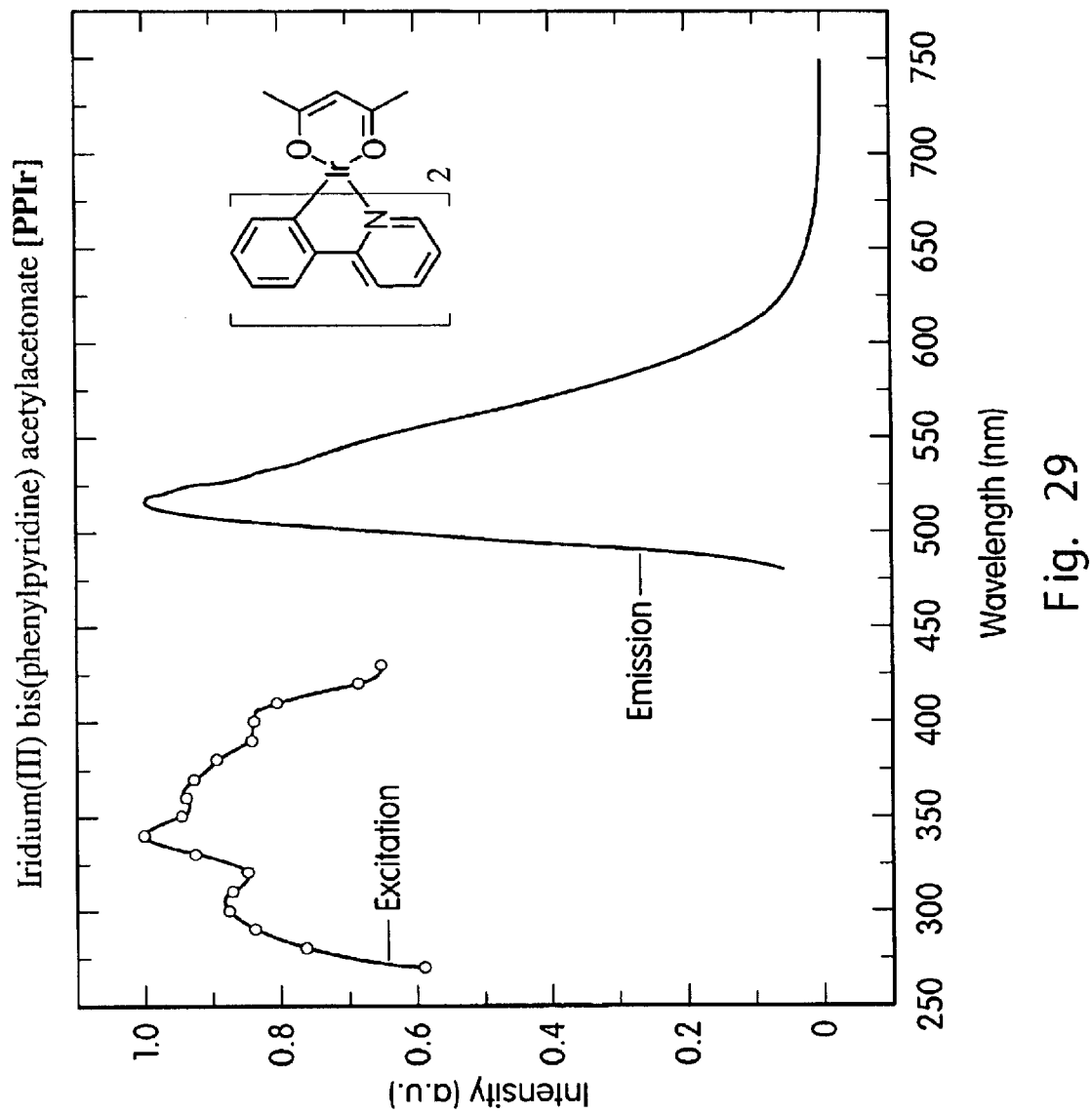
FIG. 29. Emission spectra of PPIr.
Figure 30:
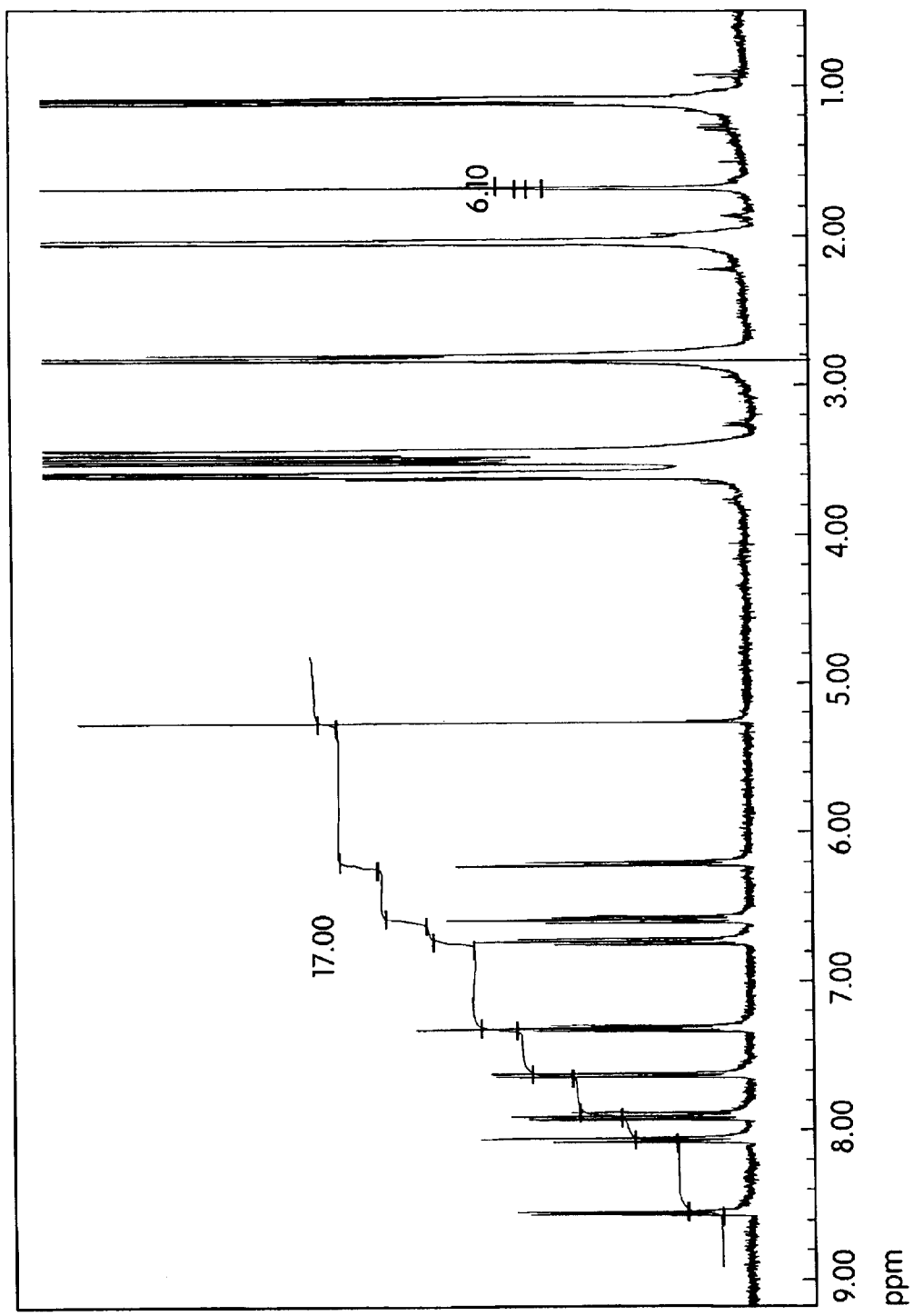
FIG. 30. Proton NMR spectrum of PPIr.

Ir(ppy)$_2$(acac), PPIr. The chloride bridged dimer (Ir(ppy)$_2$Cl)$_2$ (0.080 g, 0.078 mmol), acetylacetone (0.025 g) and sodium carbonate (0.083 g) were mixed in 10 ml of 2-ethoxyethanol. The mixture was refluxed under N$_2$ for 10 hrs or until no dimer was revealed by TLC. The reaction was then cooled and the yellow precipitate filtered. The product was purified by flash chromatography using dichloromethane. Product: yellow solid (yield 87%). $^1$H NMR (360 MHz, acetone-d$_6$), ppm: 8.54 (d,2H), 8.06 (d,2H), 7.92 (m,2H), 7.81 (d,2H), 7.35 (d,2H), 6.78 (m,2H), 6.69 (m,2H), 6.20 (d,2H), 5.12 (s,1H), 1.62 (s,6H). MS, e/z: 600 (M+, 75%), 501 (100%). The emission spectrum is in FIG. 29 and the proton NMR spectrum is in FIG. 30.

Figure 31:
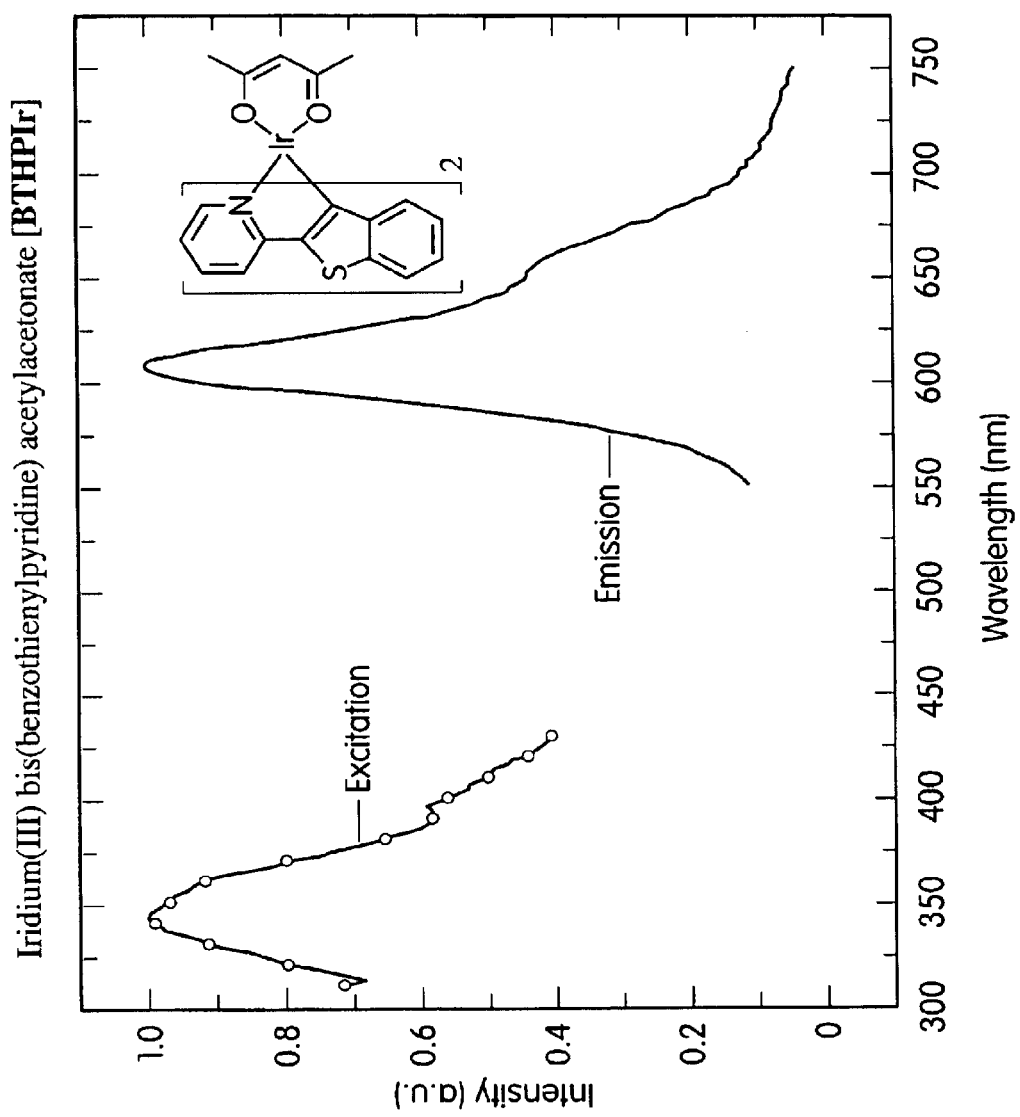
FIG. 31. Emission spectrum of BTHPIr (=BTPIr).

Ir(bthpy)$_2$(acac), BTPIr. The chloride bridged dimer (Ir(bthpy)$_2$Cl)$_2$ (0.103 g, 0.078 mmol), acetylacetone (0.025 g) and sodium carbonate (0.083 g) were mixed in 10 ml of 2-ethoxyethanol. The mixture was refluxed under N$_2$ for 10 hrs or until no dimer was revealed by TLC. The reaction was then cooled and the yellow precipitate filtered. The product was purified by flash chromatography using dichloromethane. Product: yellow solid (yield 49%). MS, e/z: 712 (M+,66%), 613 (100%). Emission spectrum is in FIG. 31.

[Ir(ptpy)$_2$Cl]$_2$. A solution of IrCl$_3$.xH$_2$O (1.506g, 5.030 mmol) and 2-(p-tolyl)pyridine (3.509 g, 20.74 mmol) in 2-ethoxyethanol (30 mL) was refluxed for 25 hours. The yellow-green mixture was cooled to room temperature and 20 mL of 1.0 M HCl was added to precipitate the product. The mixture was filtered and washed with 100 mL of 1.0 M HCl followed by 50 mL of methanol then dried. The product was obtained as a yellow powder (1,850 g, 65%).

[Ir(ppz)$_2$Cl]$_2$. A solution of IrCl$_3$.xH$_2$O (0.904 g, 3.027 mmol) and 1-phenylpyrazole (1.725 g, 11.96 mmol) in 2-ethoxyethanol (30 mL) was refluxed for 21 hours. The gray-green mixture was cooled to room temperature and 20 mL of 1.0 M HCl was added to precipitate the product. The mixture was filtered and washed with 100 mL of 1.0 M HCl followed by 50 mL of methanol then dried. The product was obtained as a light gray powder (1.133 g, 73%).

[Ir(C6)$_2$Cl]$_2$. A solution of IrCl$_3$.xH$_2$O (0.075 g, 0.251 mmol) and coumarin C6 [3-(2-benzothiazolyl)-7-(diethyl) coumarin] (Aldrich) (0.350 g, 1.00 mmol) in 2-ethoxyethanol (15 mL) was refluxed for 22 hours. The dark red mixture was cooled to room temperature and 20 mL of 1.0 M HCl was added to precipitate the product. The mixture was filtered and washed with 100 mL of 1.0 M HCl followed by 50 mL of methanol. The product was dissolved in and precipitated with methanol. The solid was filtered and washed with methanol until no green emission was observed in the filtrate. The product was obtained as an orange powder (0.0657 g, 28%).

Figure 32:
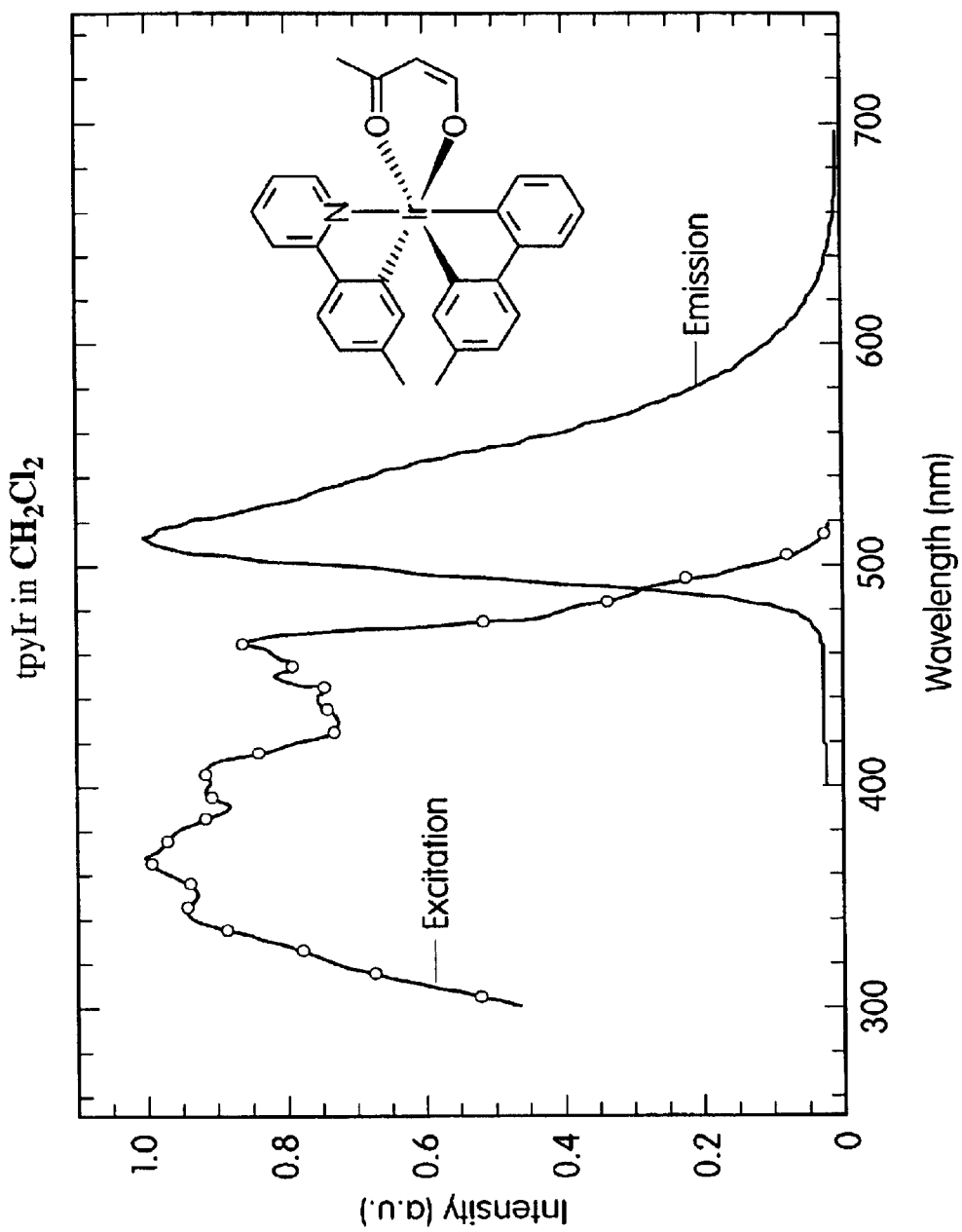
FIG. 32. Emission spectrum of tpyIr.
Figure 33:
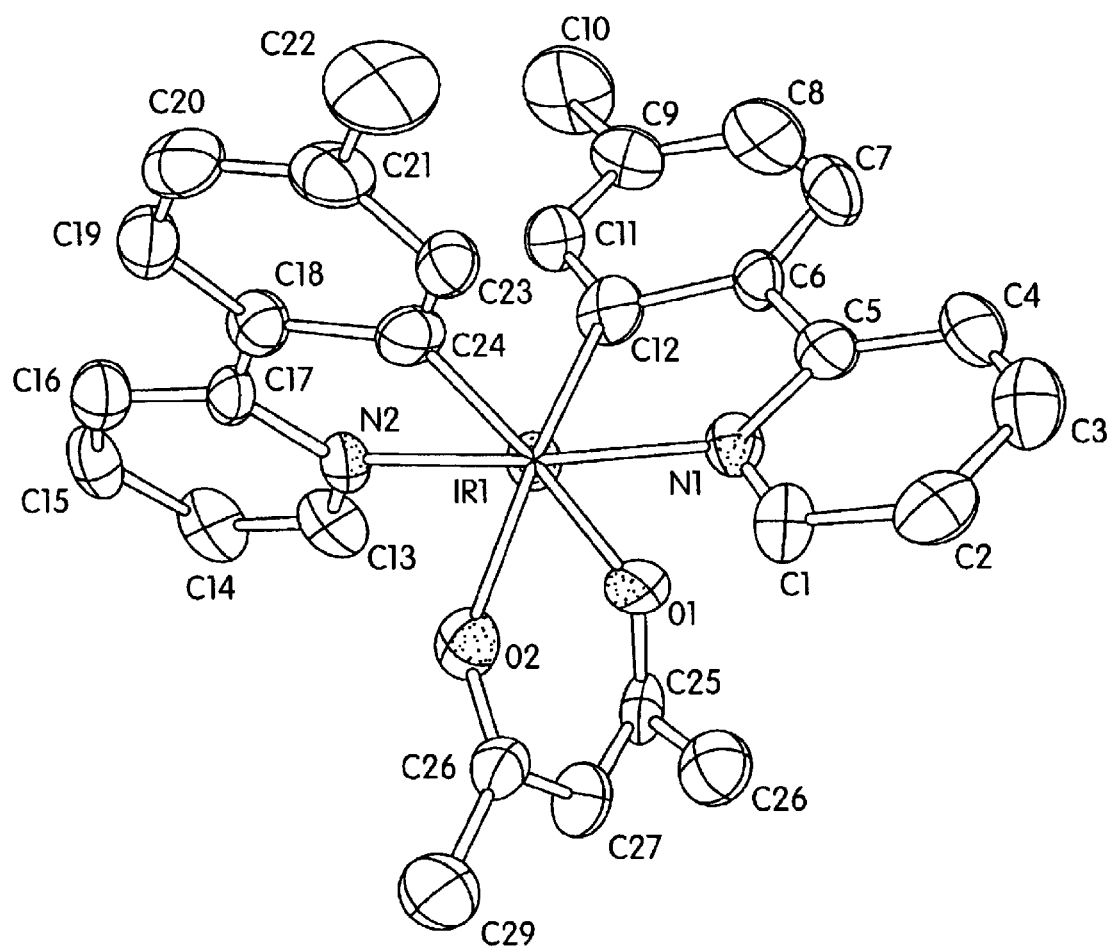
FIG. 33. Crystal structure of tpyIr showing trans arrangement of nitrogen.

Ir(ptpy)$_2$(acac) (tpylr). A solution of [Ir(ptpy)$_2$Cl]$_2$ (1.705 g, 1.511 mmol), 2,4-pentanedione (3.013 g, 30.08 mmol) and (1.802 g, 17.04 mmol) in 1,2-dichloroethane (60 mL) was refluxed for 40 hours. The yellow-green mixture was cooled to room temperature and the solvent was removed under reduced pressure. The product was taken up in 50 mL of CH$_2$Cl$_2$ and filtered through Celite. The solvent was removed under reduced pressure to yield orange crystals of the product (1.696 g, 89%). The emission spectrum is given in FIG. 32. The results of an x-ray diffraction study of the structure are given in FIG. 33. One sees that the nitrogen atoms of the tpy ("tolyl pyridyl") groups are in a trans configuration. For the x-ray study, the number of reflections was 4663 and the R factor was 5.4%.

Figure 34:
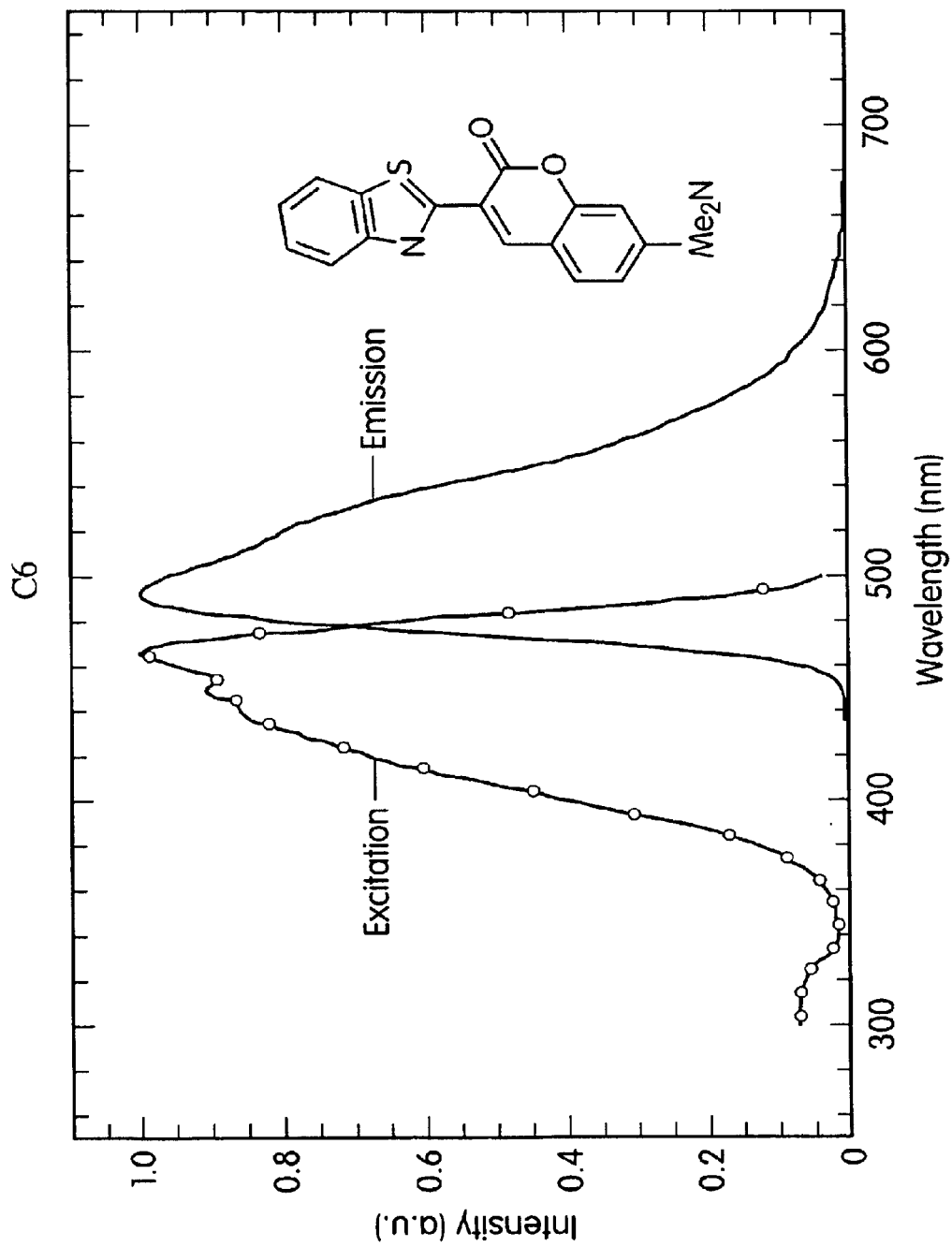
FIG. 34. Emission spectrum of C6.
Figure 35:
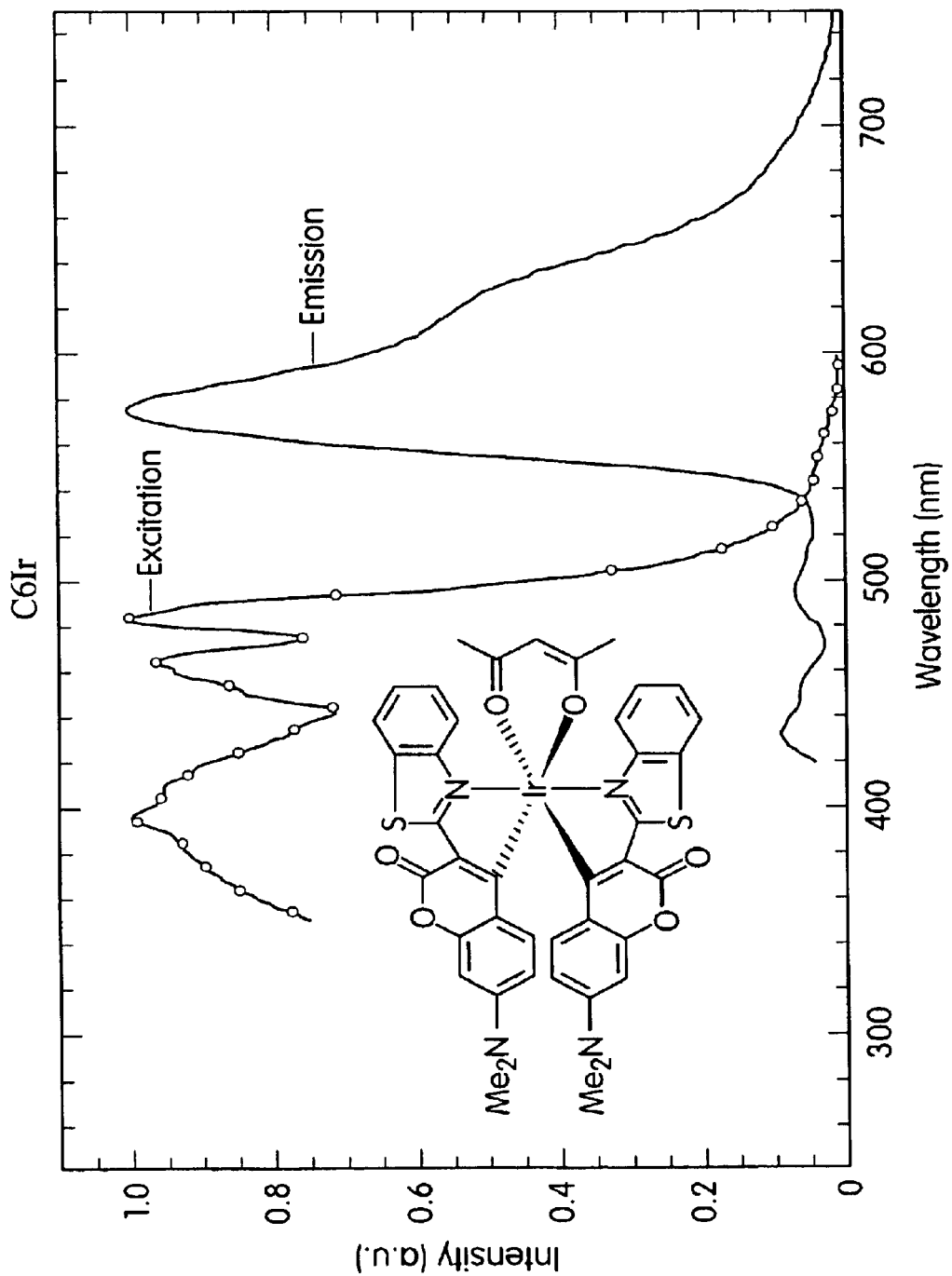
FIG. 35. Emission spectrum of C6Ir.

Ir(C6)$_2$(acac) (C6Ir). Two drops of 2,4-pentanedione and an excess of Na$_2$CO$_3$ was added to solution of [Ir(C6)$_2$Cl]$_2$ in CDCl$_3$. The tube was heated for 48 hours at 50° C. and then filtered through a short plug of Celite in a Pasteur pipet. The solvent and excess 2,4-pentanedione were removed under reduced pressure to yield the product as an orange solid. Emission of C6 in FIG. 34 and of C6Ir in FIG. 35.

Figure 36:
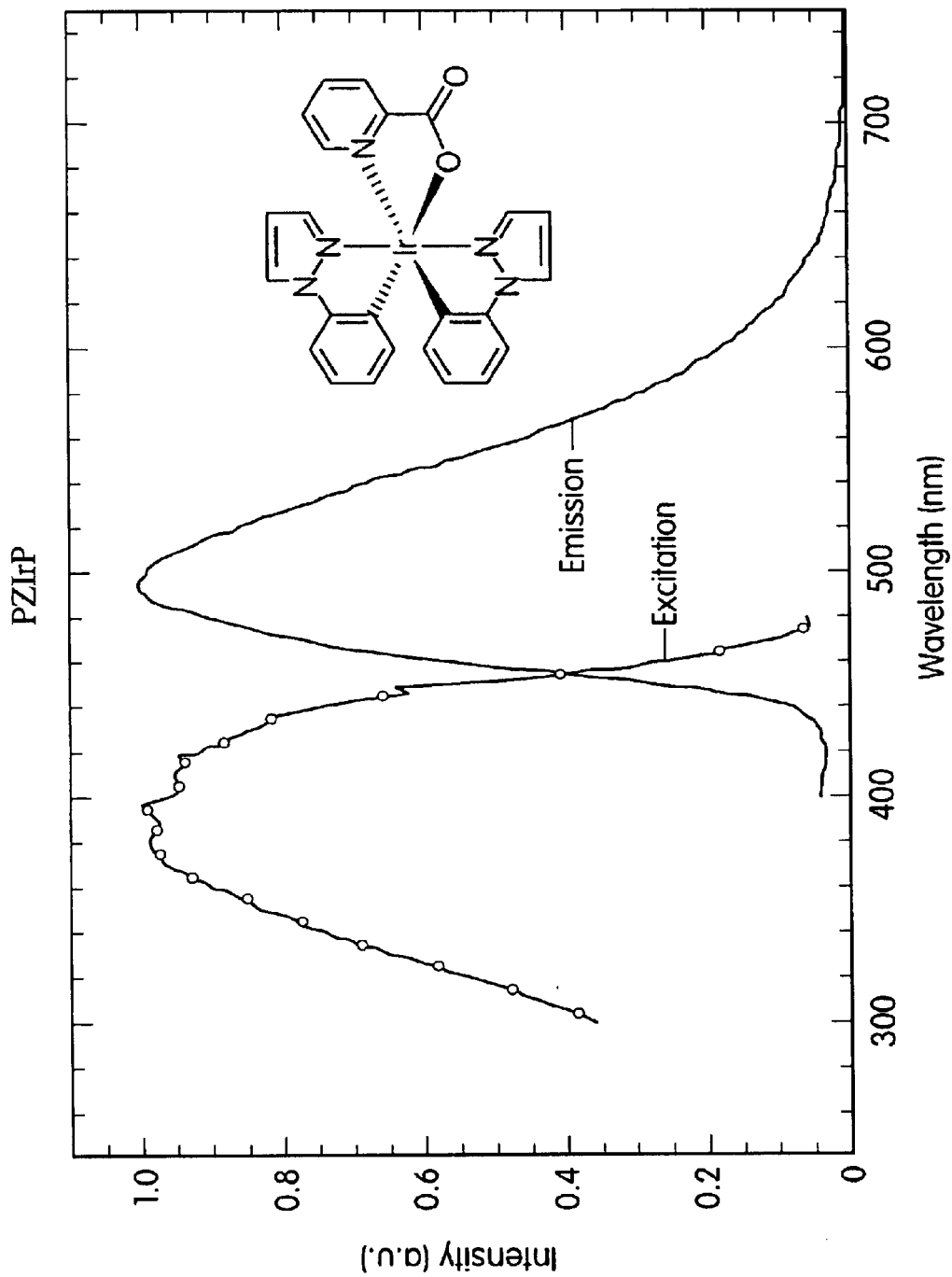
FIG. 36. Emission spectrum of PZIrP.

Ir(ppz)$_2$picolinate (PZIrp). A solution of [Ir(ppz)$_2$Cl]$_2$ (0.0545 g, 0.0530 mmol) and picolinic acid (0.0525 g, 0.426 mmol) in CH$_2$Cl$_2$ (15 mL) was refluxed for 16 hours. The light green mixture was cooled to room temperature and the solvent was removed under reduced pressure. The resultant solid was taken up in 10 mL of methanol and a light green solid precipitated from the solution. The supernatant liquid was decanted off and the solid was dissolved in CH$_2$Cl$_2$ and filtered through a short plug of silica. The solvent was removed under reduced pressure to yield light green crystals of the product (0.0075 g, 12%). Emission in FIG. 36.

2-(1-naphthyl)benzoxazole, (BZO-Naph). (11.06 g, 101 mmol) of 2-aminophenol was mixed with (15.867 g, 92.2 mmol) of 1-naphthoic acid in the presence of polyphosphoric acid. The mixture was heated and stirred at 240° C. under N$_2$ for 8 hrs. The mixture was allowed to cool to 100° C., this was followed by addition of water. The insoluble residue was collected by filtration, washed with water then reslurried in an excess of 10% Na$_2$CO$_3$. The alkaline slurry was filtered and the product washed thoroughly with water and dried under vacuum. The product was purified by vacuum distillation. BP 140° C. /0.3 mmHg. Yield 4.8 g (21%).

Tetrakis(2-(1-naphthyl)benzoxazoleC$^2$, N')($\mu$-dichloro) diiridium. ((Ir$_2$(BZO-Naph)$_4$Cl)$_2$). Iridium trichloride hydrate (0.388 g) was combined with 2-(1-naphthyl) benzoxazole (1.2 g, 4.88 mmol). The mixture was dissolved in 2-ethoxyethanol (30 mL) then refluxed for 24 hrs. The solution was cooled to room temperature, the resulting orange solid product was collected in a centrifuge tube. The dimer was washed with methanol followed by chloroform through four cycles of centrifuge/redispersion cycles. Yield 0.66 g.

Figure 37:
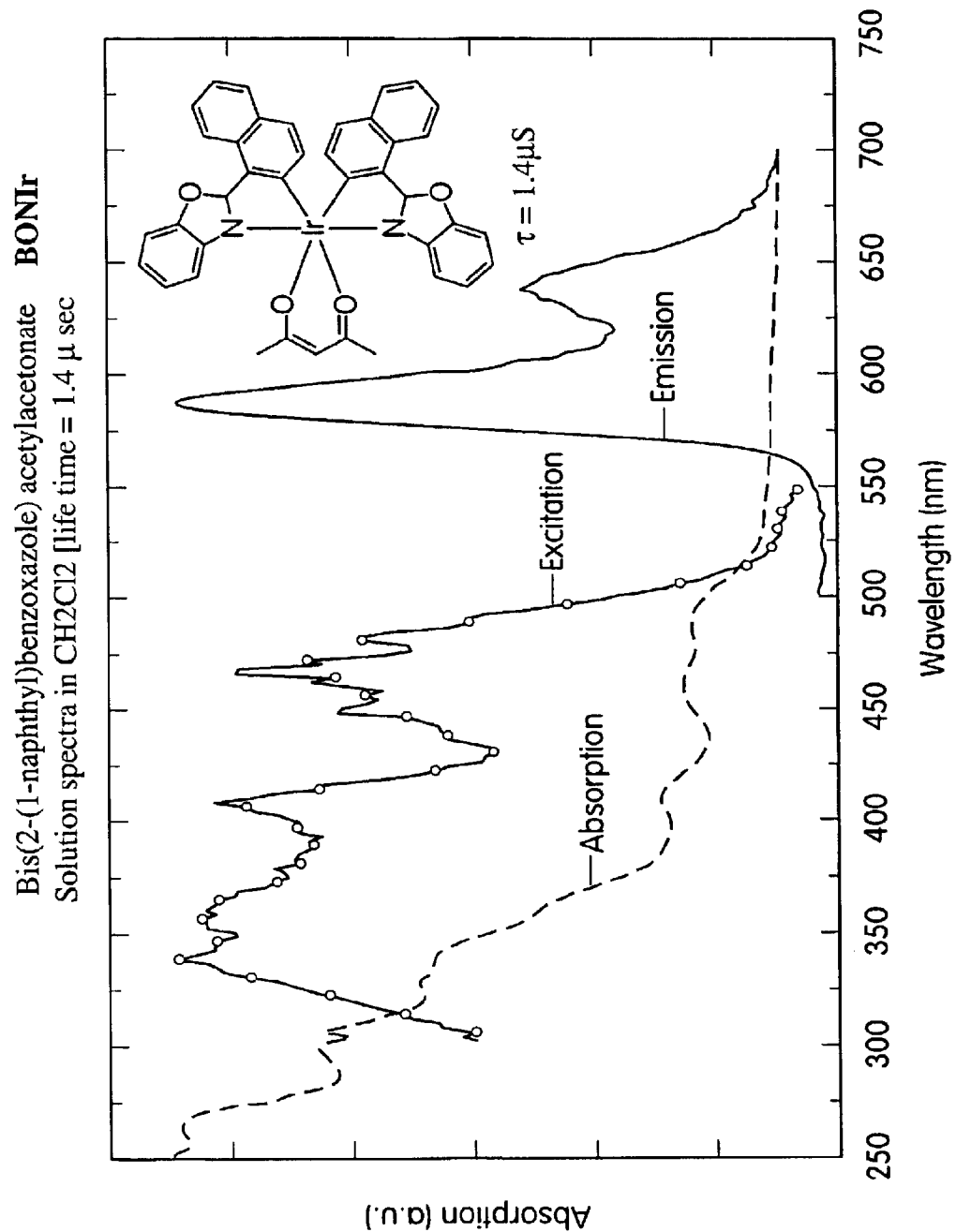
FIG. 37. Emission spectrum of BONIr.
Figure 38:
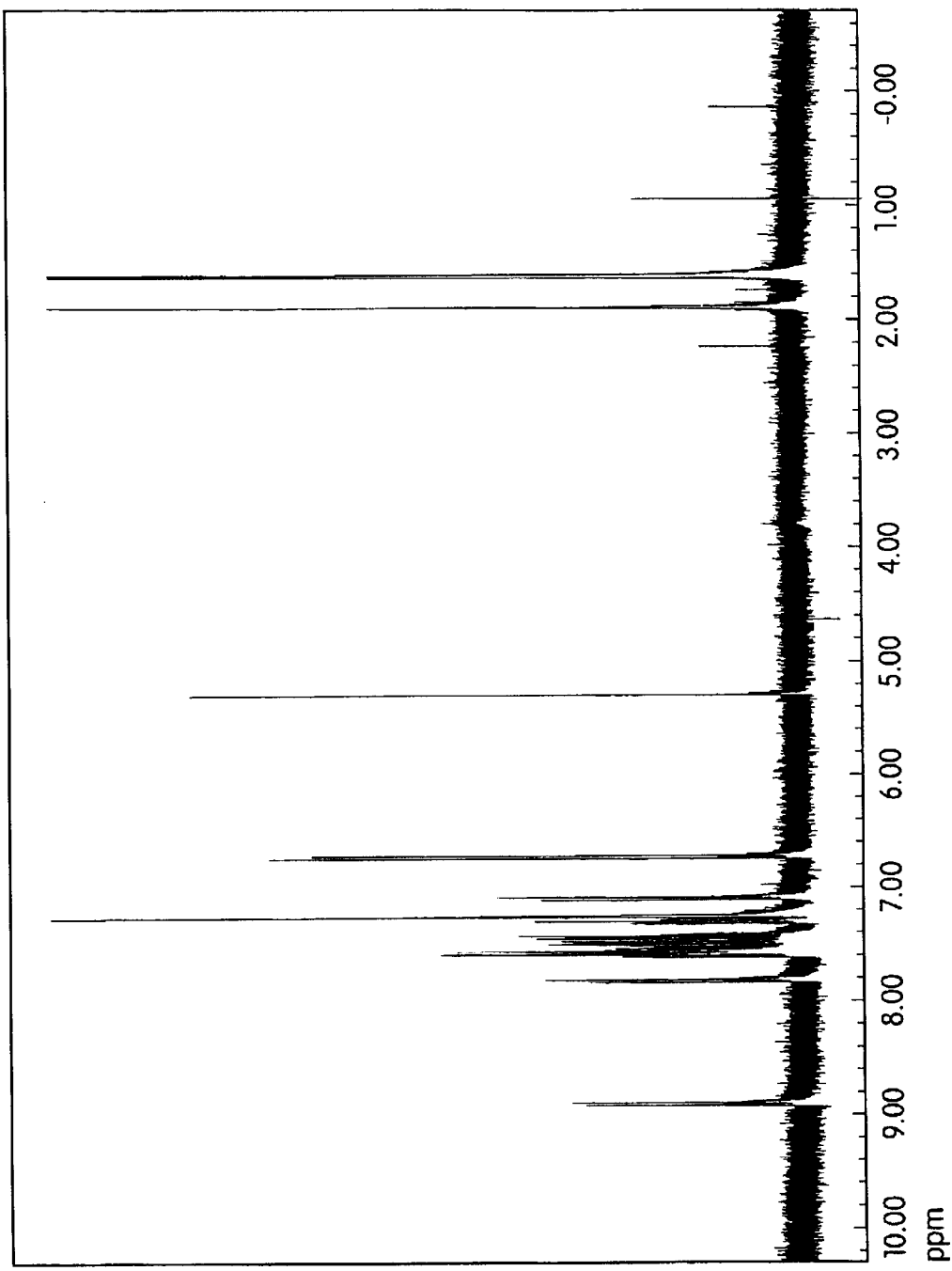
FIG. 38. Proton NMR spectrum of BONIr.

Bis(2-(1-naphthyl)benzoxazole) acetylacetonate, Ir(BZO-Naph)$_2$(acac), (BONIr). The chloride bridged dimer (Ir$_2$(BZO-Naph)$_4$Cl)$_2$ (0.66 g, 0.46 mmol), acetylacetone (0.185 g) and sodium carbonate (0.2 g) were mixed in 20 ml of dichloroethane. The mixture was refluxed under N$_2$ for 60 hrs. The reaction was then cooled and the orange/red precipitate was collected in centrifuge tube. The product was washed with water/methanol (1:1) mixture followed by methanol wash through four cycles of centrifuge/redispersion cycles. The orange/red solid product was purified by sublimation. SP 250° C./2×10$^{-5}$ torr, yield 0.57 g (80%). The emission spectrum is in FIG. 37 and the proton NMR spectrum is in FIG. 38.

Figure 39:
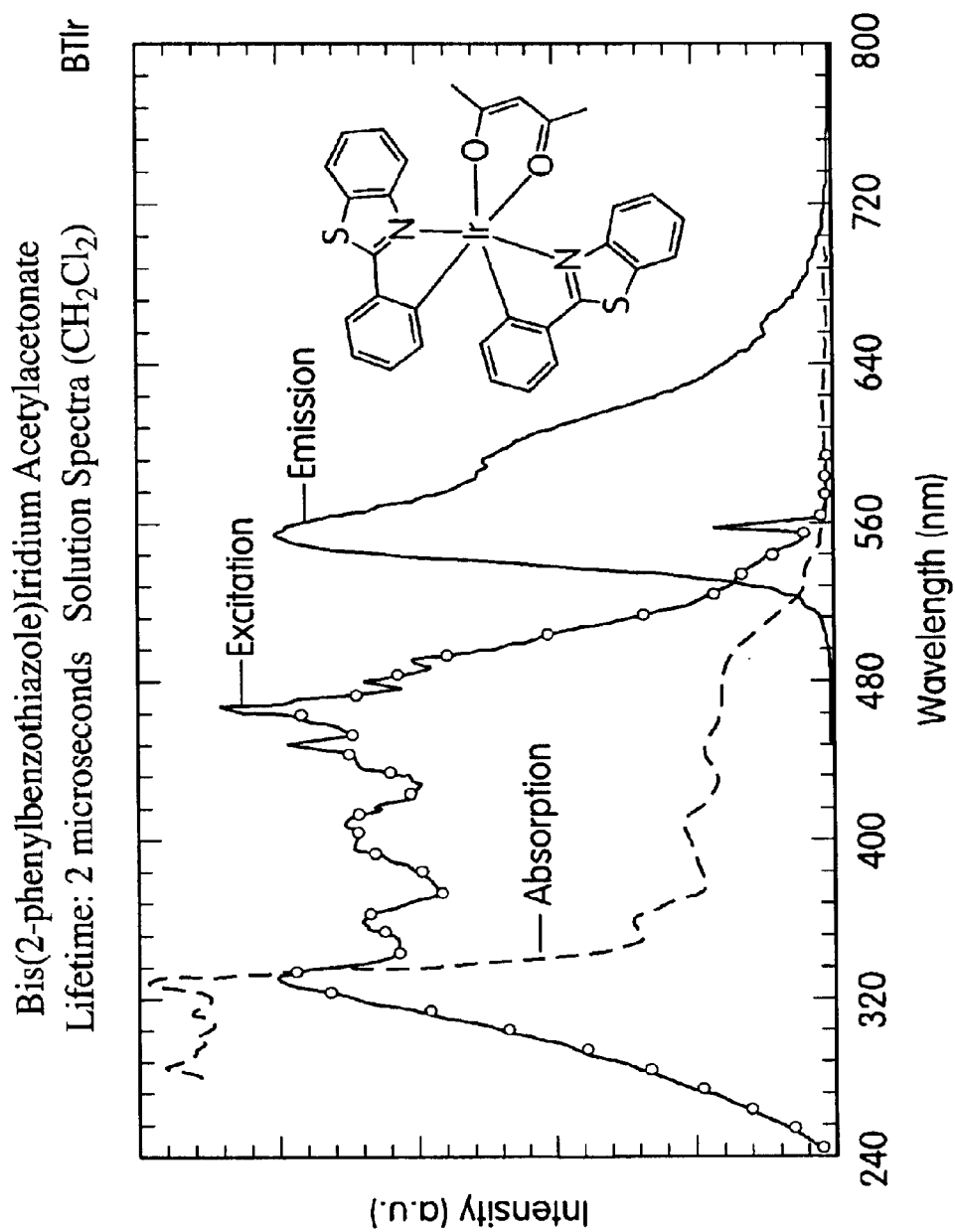
FIG. 39. Emission spectrum of BTIr.
Figure 40:
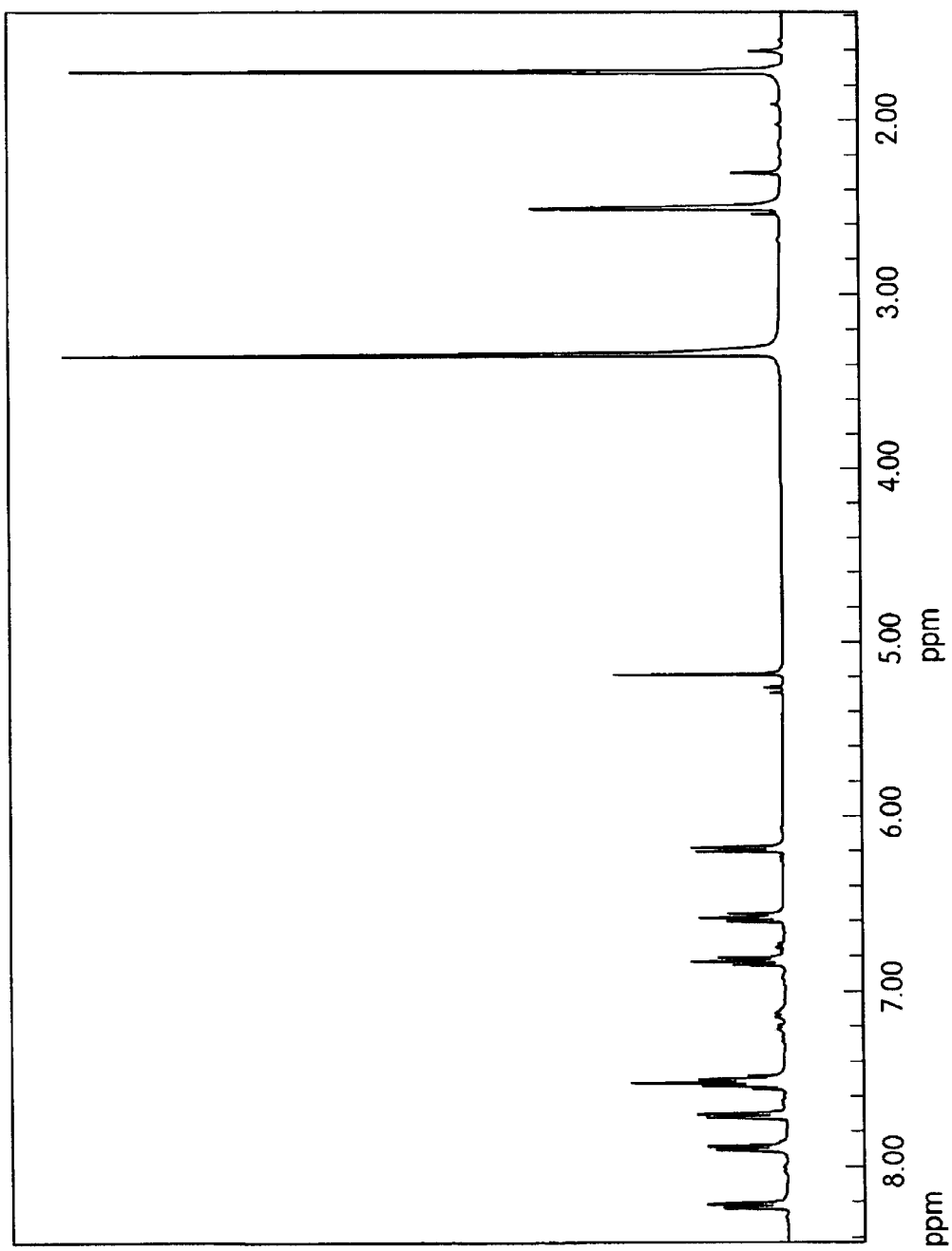
FIG. 40. Proton NMR spectrum of BTIr.

Bis(2-phenylbenzothiazole) Iridium acetylacetonate (BTIr). 9.8 mmol (0.98 g, 1.0 mL) of 2,4-pentanedione was added to a room-temperature solution of 2.1 mmol 2-phenylbenzothiazole Iridium chloride dimer (2.7 g) in 120 mL of 2-ethoxyethanol. Approximately 1 g of sodium carbonate was added, and the mixture was heated to reflux under nitrogen in an oil bath for several hours. Reaction mixture was cooled to room temperature, and the orange precipitate was filtered off via vacuum. The filtrate was concentrated and methanol was added to precipitate more product. Successive filtrations and precipitations afforded a 75% yield. The emission spectrum is in FIG. 39 and the proton NMR spectrum is in FIG. 40.

Figure 41:
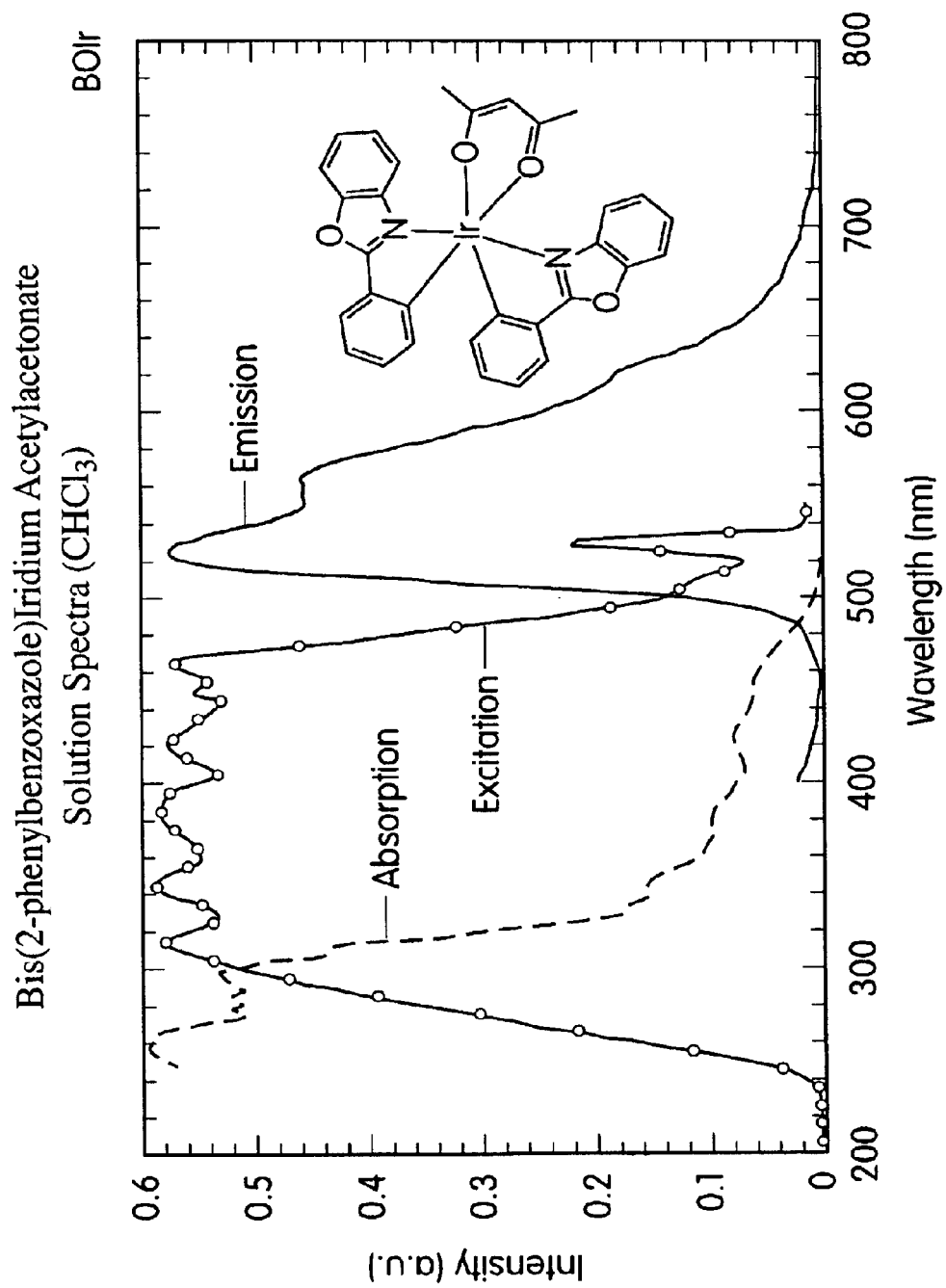
FIG. 41. Emission spectrum of BOIr.
Figure 42:
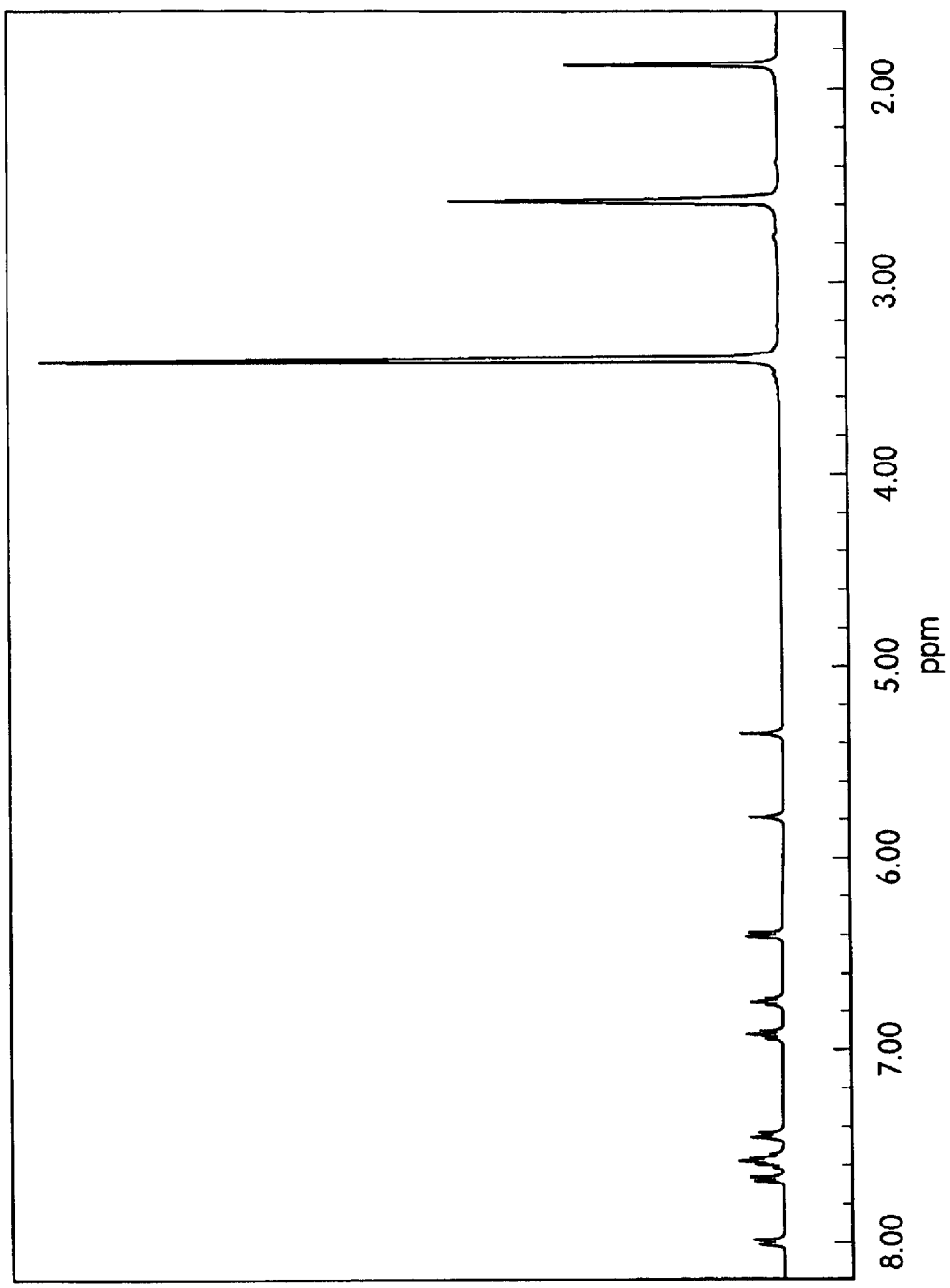
FIG. 42. Proton NMR spectrum of BOIr.

Bis(2-phenylbenzooxazole) Iridium acac (BOIr). 9.8 mmol (0.98 g, 1.0 mL) of 2,4-pentanedione was added to a room-temperature solution of 2.4 mmol 2-phenylbenzoxazole Iridium chloride dimer (3.0 g) in 120 mL of 2-ethoxyethanol. Approximately 1 g of sodium carbonate was added, and the mixture was heated to reflux under nitrogen in an oil bath overnight (~16 hrs.). Reaction mixture was cooled to room temperature, and the yellow precipitate was filtered off via vacuum. The filtrate was concentrated and methanol was added to precipitate more product. Successive filtrations and precipitations afforded a 60% yield. The emission spectrum is in FIG. 41 and the proton NMR spectrum is in FIG. 42.

Figure 43:
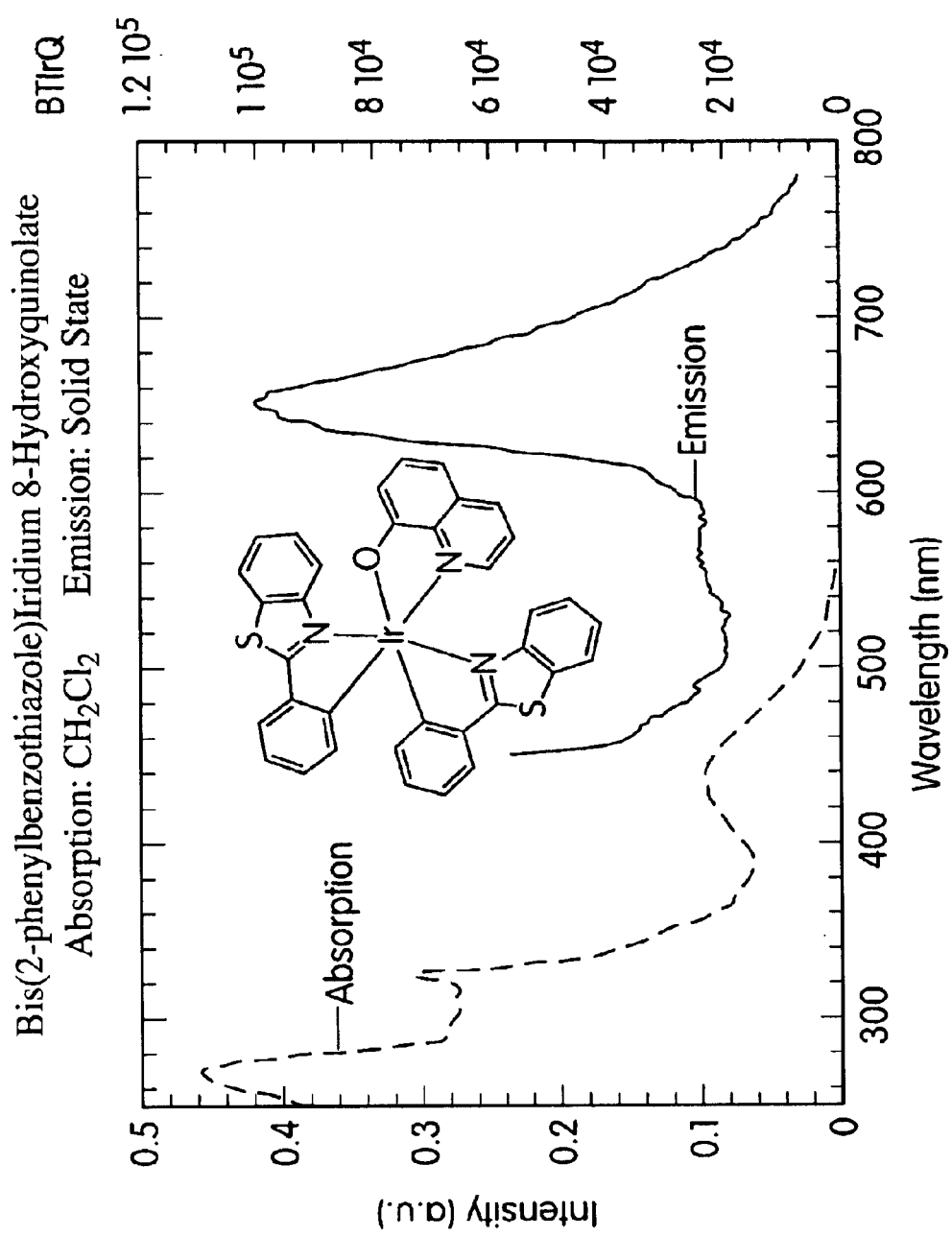
FIG. 43. Emission spectrum of BTIrQ.
Figure 44:
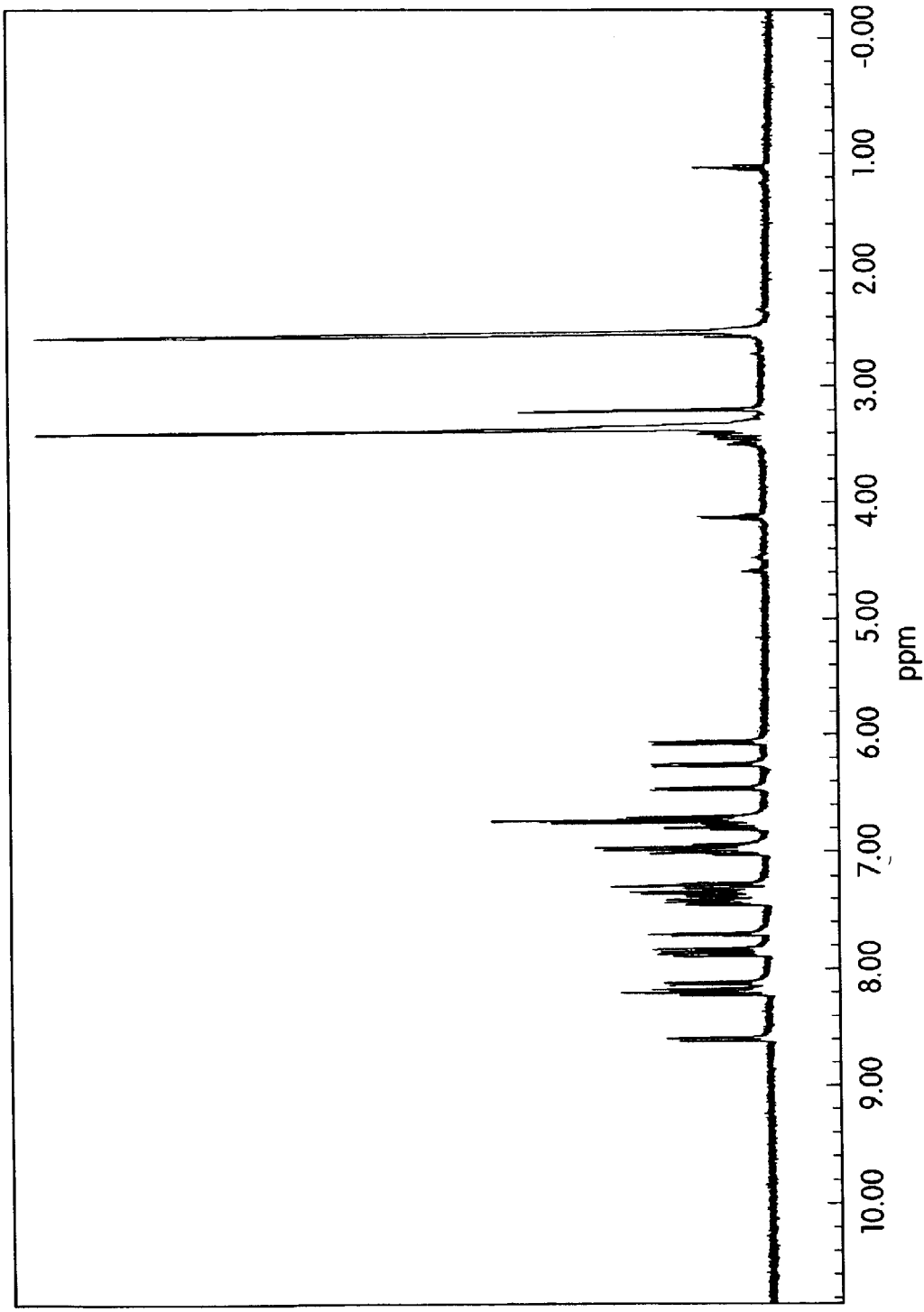
FIG. 44. Proton NMR spectrum of BTIrQ.

Bis(2-phenylbenzothiazole) Iridium (8-hydroxyquinolate) (BTIrQ). 4.7 mmol (0.68 g) of 8-hydroxyquinoline was added to a room-temperature solution of 0.14 mmol 2-phenylbenzothiazole Iridium chloride dimer (0.19 g) in 20 mL of 2-ethoxyethanol. Approximately 700 mg of sodium carbonate was added, and the mixture was heated to reflux under nitrogen in an oil bath overnight (23 hrs.). Reaction mixture was cooled to room temperature, and the red precipitate was filtered off via vacuum. The filtrate was concentrated and methanol was added to precipitate more product. Successive filtrations and precipitations afforded a 57% yield. The emission spectrum is in FIG. 43 and the proton NMR spectrum is in FIG. 44.

Figure 45:
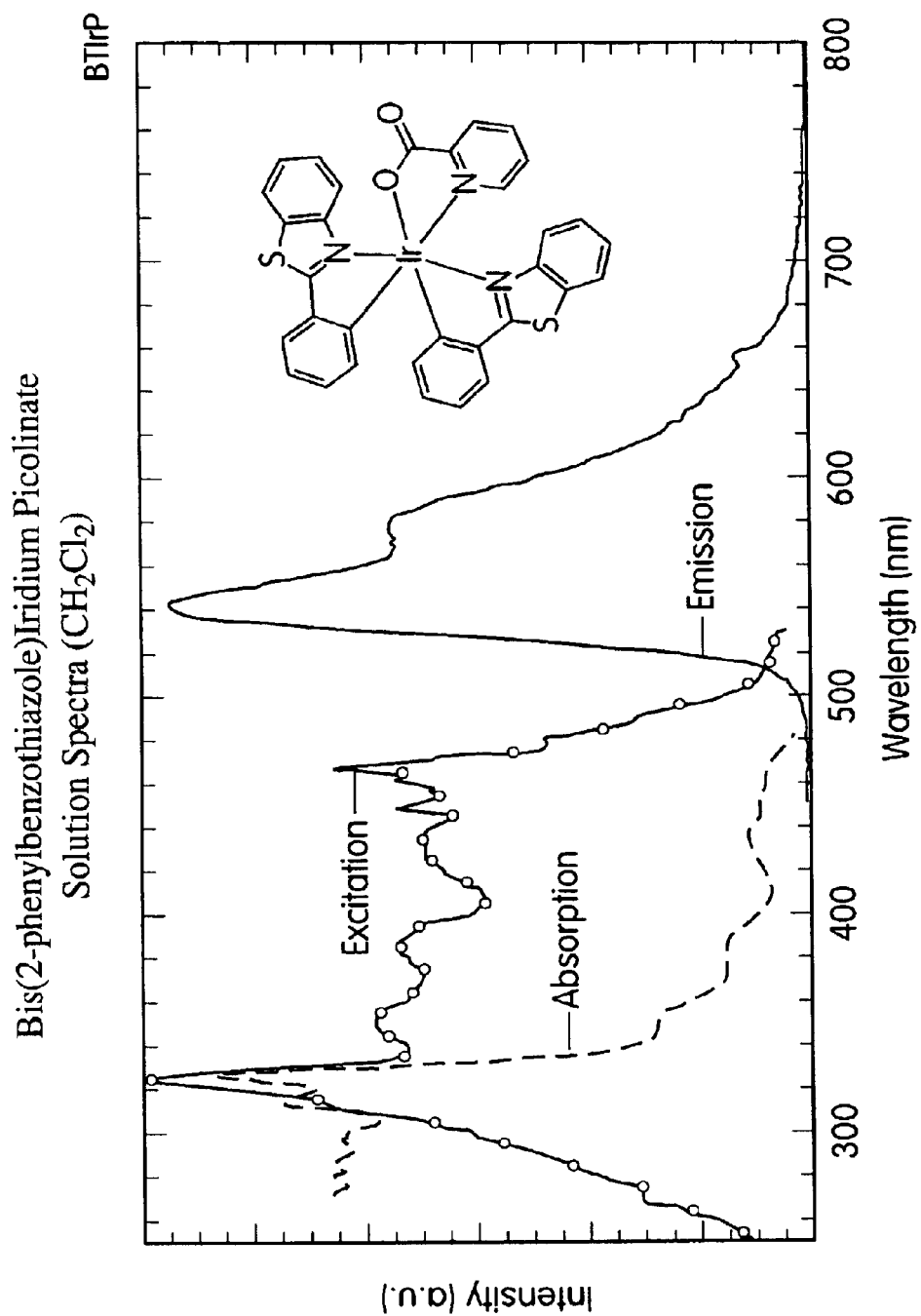
FIG. 45. Emission spectrum of BTIrP.

Bis(2-phenylbenzothiazole) Iridium picolinate (BTIrP). 2.14 mmol (0.26 g) of picolinic acid was added to a room-temperature solution of 0.80 mmol 2-phenylbenzothiazole Iridium chloride dimer (1.0 g) in 60 mL of dichloromethane. The mixture was heated to reflux under nitrogen in an oil bath for 8.5 hours. The reaction mixture was cooled to room temperature, and the yellow precipitate was filtered off via vacuum. The filtrate was concentrated and methanol was added to precipitate more product. Successive filtrations and precipitations yielded about 900 mg of impure product. Emission spectrum is in FIG. 45.

Figure 46:
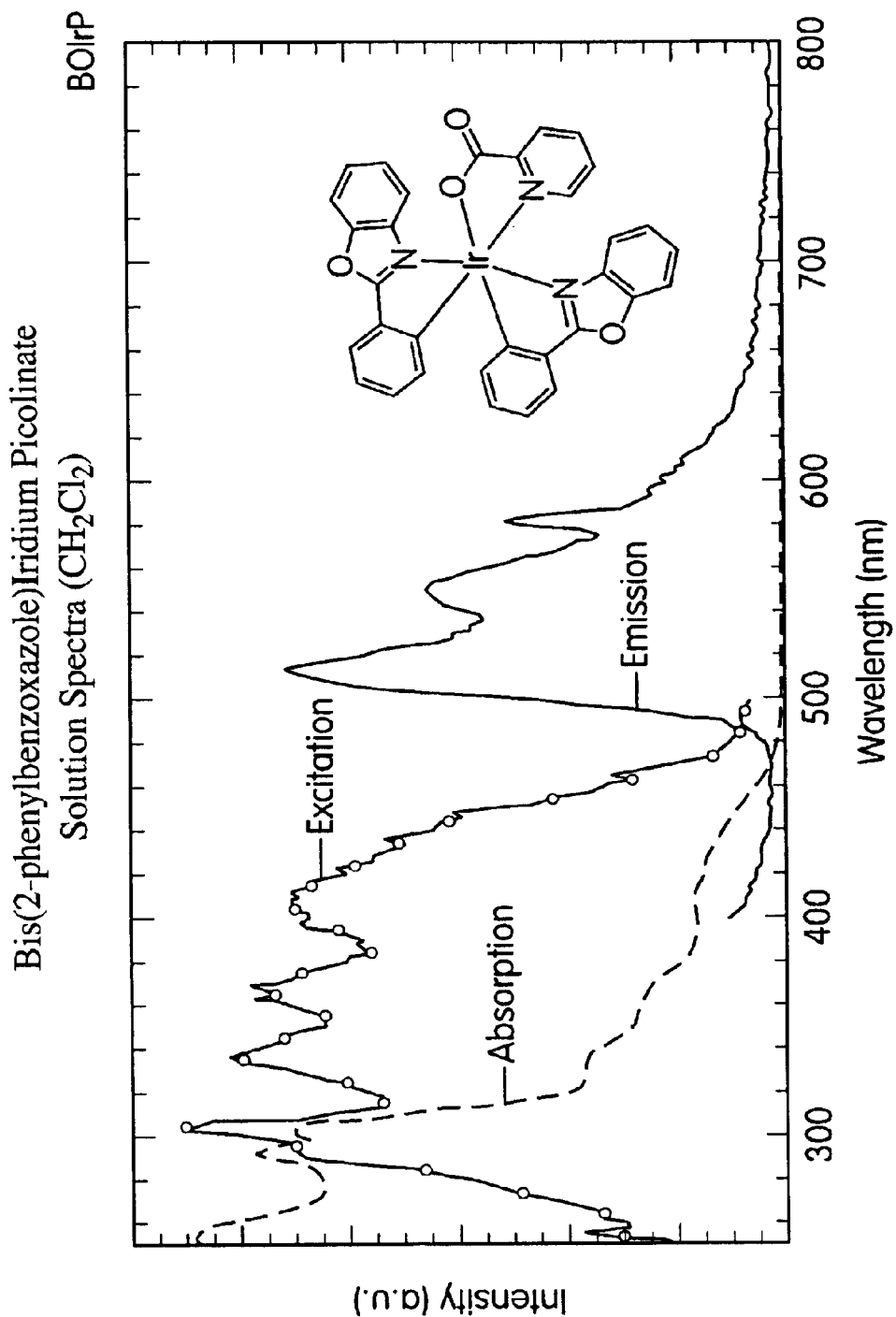
FIG. 46. Emission spectrum of BOIrP.

Bis(2-phenylbenzooxazole) Iridium picolinate (BOIrP). 0.52 mmol (0.064 g) of picolinic acid was added to a room-temperature solution of 0.14 mmol 2-phenylbenzoxazole Iridium chloride dimer (0.18 g) in 20 mL of dichloromethane. The mixture was heated to reflux under nitrogen in an oil bath overnight (17.5 hrs.). Reaction mixture was cooled to room temperature, and the yellow precipitate was filtered off via vacuum. The precipitate was dissolved in dichloromethane and transferred to a vial, and the solvent was removed. Emission spectrum is in FIG. 46.

Figure 47:
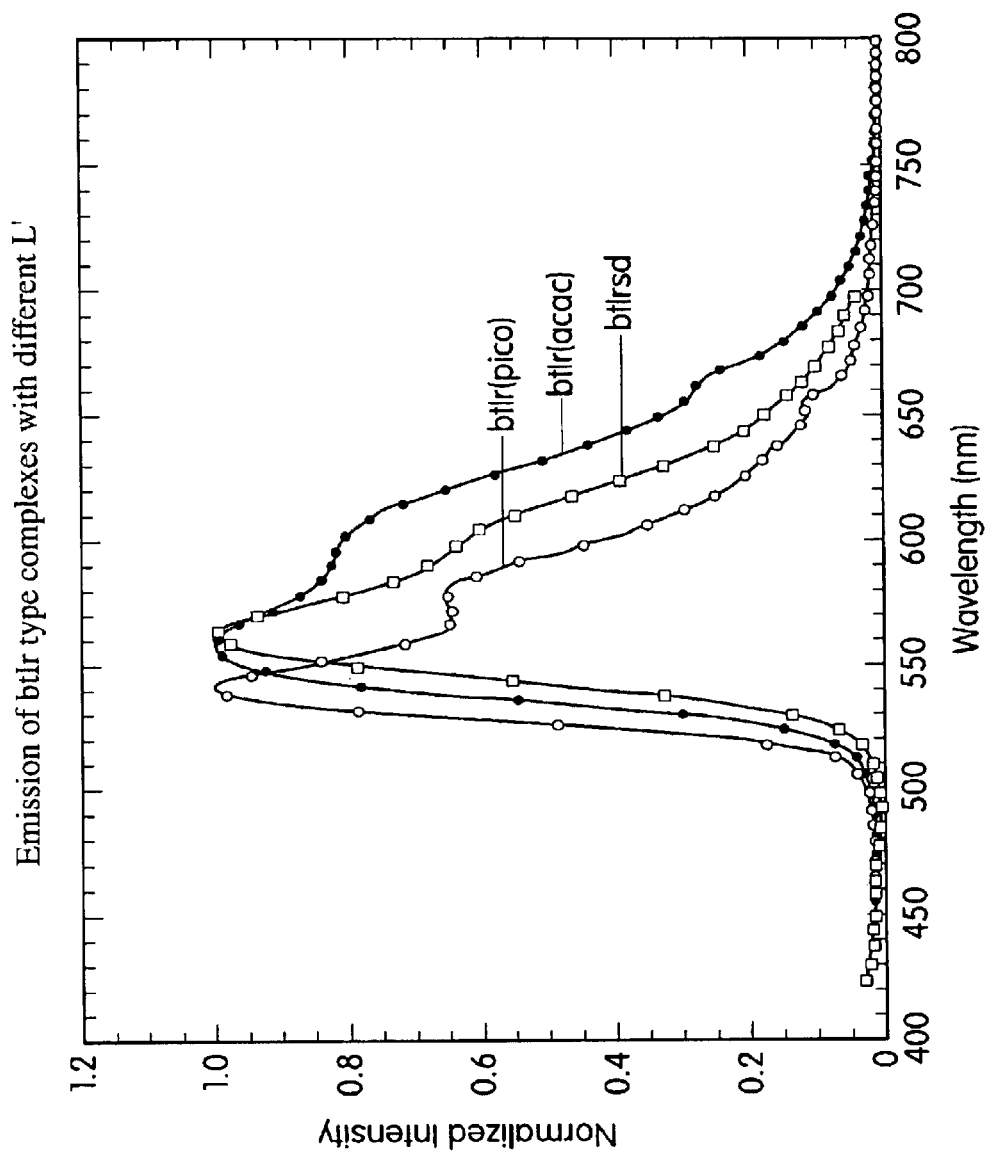
FIG. 47. Emission spectrum of btIr-type complexes with different ligands.

Comparative emission spectra for different L' in btIr complexes are shown in FIG. 47.

These syntheses just discussed have certain advantages over the prior art.

Compounds of formula PtL$_3$ cannot be sublimed without decomposition. Obtaining compounds of formula IrL$_3$ can be problematic. Some ligands react cleanly with Ir(acac)$_3$ to give the tris complex, but more than half of the ligands we have studied do not react cleanly in the reaction:

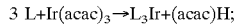
3 L+Ir(acac)$_3$→L$_3$Ir+(acac)H;

typically 30% yield, L=2-phenylpyridine, benzoquinoline, 2-thienylpyridine. A preferred route to Ir complexes can be through the chloride-bridged dimer L$_2$M($\mu$-Cl)$_2$ML$_2$ via the reaction:

4 L+IrCl$_3$.nH$_2$O→L$_2$M($\mu$-Cl)$_2$ML$_2$+4HCl

Although fewer than 10% of the ligands we have studied failed to give the Ir dimer cleanly and in high yield, the conversion of the dimer into the tris complex IrL$_3$ is problematic working for only a few ligands. L$_2$M($\mu$-Cl)$_2$ML$_2$+2Ag$^+$+2L→L$_3$Ir+2AgCl.

We have discovered that a far more fruitful approach to preparing phosphorescent complexes is to use chloride bridged dimers to create emitters. The dimer itself does not emit strongly, presumably because of strong self quenching by the adjacent metal (e.g., iridium) atoms. We have found that the chloride ligands can be replaced by a chelating ligand to give a stable, octahedral metal complex through the chemistry:

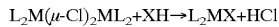
L$_2$M($\mu$-Cl)$_2$ML$_2$+XH→L$_2$MX+HCl

We have extensively studied the system wherein M=iridium. The resultant iridium complexes emit strongly, in most cases with lifetimes of 1–3 microseconds ("$\mu$sec"). Such a lifetime is indicative of phosphorescence (see Charles Kittel, Introduction to Solid State Physics). The transition in these materials is a metal ligand charge transfer ("MLCT").

Figure 11:
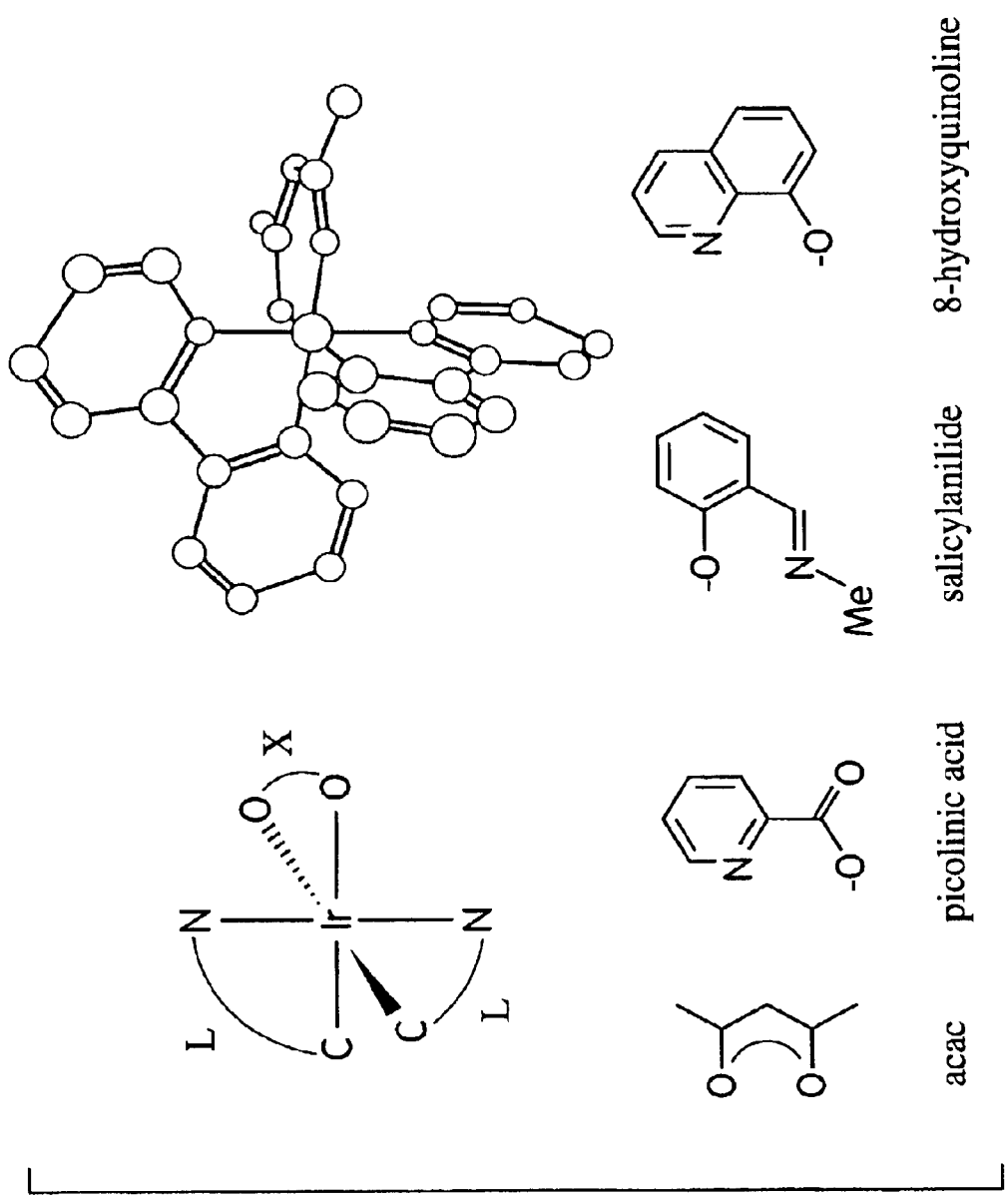
FIG. 11. Expected structure of $L_2IrX$ complexes along with the structure expected for PPIr. Four examples of X ligands used for these complexes are also shown. The structure shown is for an acac derivative. For the other X type ligands, the O—O ligand would be replaced with an N—O ligand.

In the discussion that follows below, we analyze data of emission spectra and lifetimes of a number of different complexes, all of which can be characterized as L$_2$MX (M=Ir), where L is a cyclometallated (bidentate) ligand and X is a bidentate ligand. In nearly every case, the emission in these complexes is based on an MLCT transition between Ir and the L ligand or a mixture of that transition and an intraligand transition. Specific examples are described below. Based on theoretical and spectroscopic studies, the complexes have an octahedral coordination about the metal (for example, for the nitrogen heterocycles of the L ligand, there is a trans disposition in the Ir octahedron). Specifically, in FIG. 11, we give the structure for L$_2$IrX, wherein L=2-phenyl pyridine and X=acac, picolinate (from picolinic acid), salicylanilide, or 8-hydroxyquinolinate.

Figure 12:
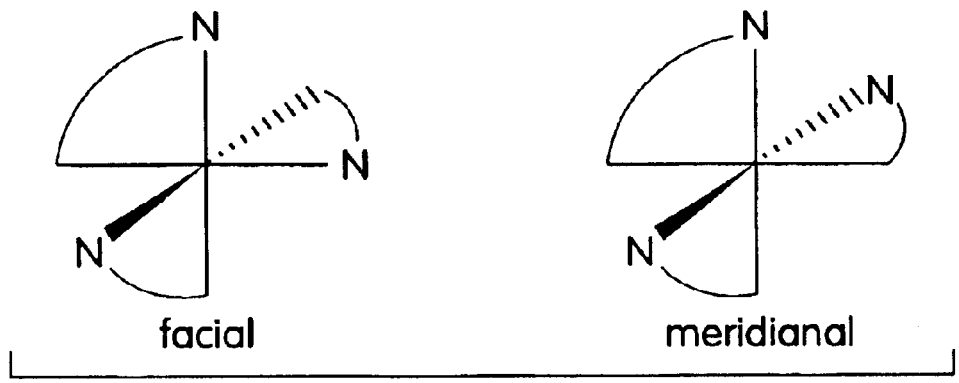
FIG. 12. Comparison of facial and meridianal isomers of $L_3M$.

A slight variation of the synthetic route to make L$_2$IrX allows formation of meridianal isomers of formula L$_3$Ir. The L$_3$Ir complexes that have been disclosed previously all have a facial disposition of the chelating ligands. Herewith, we disclose the formation and use of meridianal L₃Ir complexes as phosphors in OLEDs. The two structures are shown in FIG. 12.

The facial L₃Ir isomers have been prepared by the reaction of L with Ir(acac)₃ in refluxing glycerol as described in equation 2 (below). A preferred route into L₃Ir complexes is through the chloride bridged dimer (L₂Ir(μ-Cl)₂IrL₂), equation 3+4 (below). The product of equation 4 is a facial isomer, identical to the one formed from Ir(acac)₃. The benefit of the latter prep is a better yield of facial-L₃Ir. If the third ligand is added to the dimer in the presence of base and acetylacetone (no Ag⁺), a good yield of the meridianal isomer is obtained. The meridianal isomer does not convert to the facial one on recrystallization, refluxing in coordinating solvents or on sublimation. Two examples of these meridianal complexes have been formed, mer-Irppy and mer-Irbq (FIG. 13); however, we believe that any ligand that gives a stable facial-L₃Ir can be made into a meridianal form as well.

3 L+Ir(acac)₃→facial-L₃Ir+acacH     (2)

typically 30% yield, L=2-phenylpyridine, bezoquinoline, 2-thienylpyridine

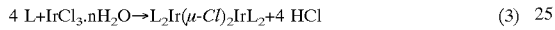

4 L+IrCl₃.nH₂O→L₂Ir(μ-Cl)₂IrL₂+4 HCl     (3)

typically>90% yield, see attached spectra for examples of L, also works well for all ligands that work in equation (2)

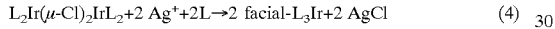

L₂Ir(μ-Cl)₂IrL₂+2 Ag⁺+2L→2 facial-L₃Ir+2 AgCl     (4)

typically 30% yield, only works well for the same ligands that work well for equation (2)

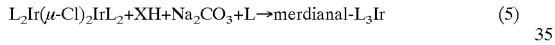

L₂Ir(μ-Cl)₂IrL₂+XH+Na₂CO₃+L→merdianal-L₃Ir     (5)

typically>80% yield, XH=acetylacetone

Figure 14:
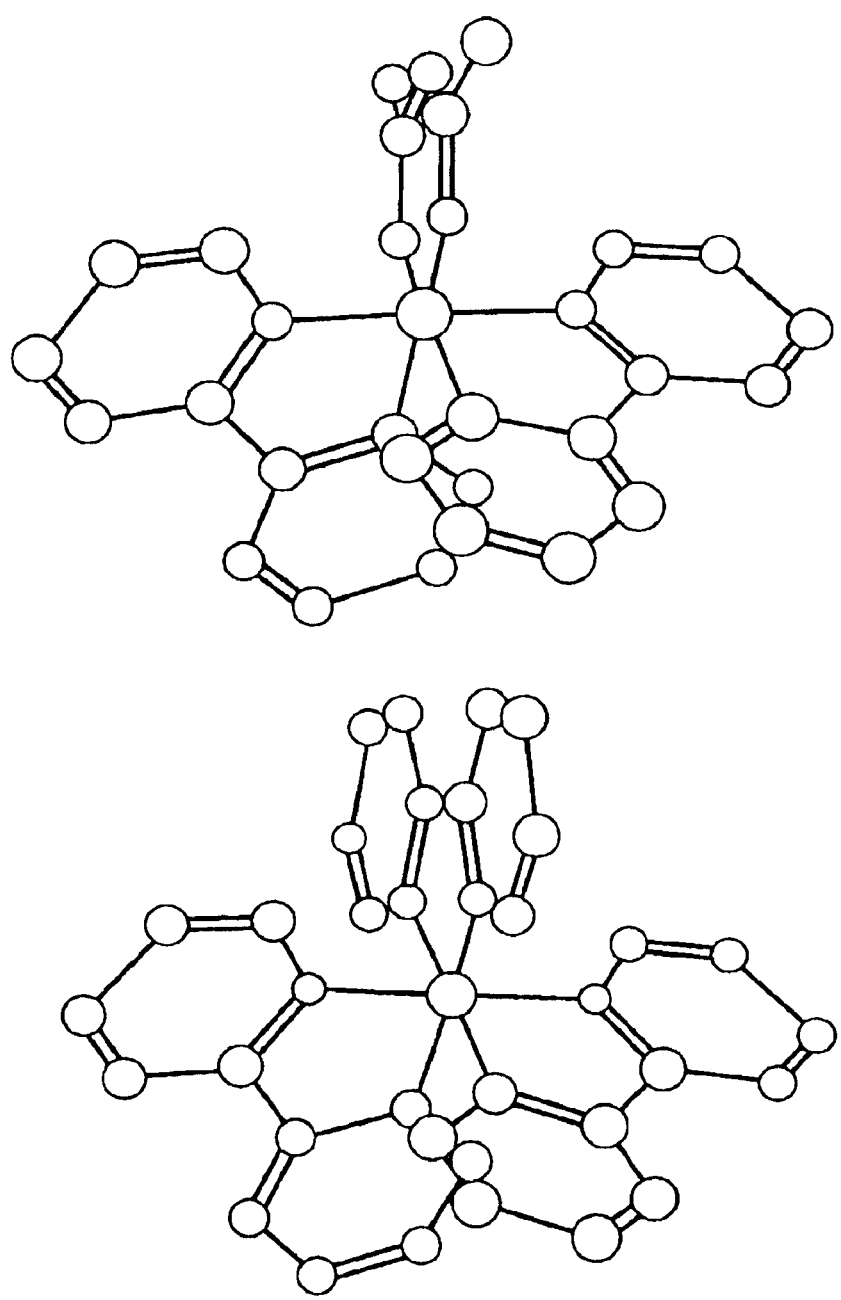
FIG. 14. Models of mer-$Ir(ppy)_3$ (left) and $(Ppy)_2Ir(acac)$ (right).

Surprisingly, the photophysics of the meridianal isomers is different from that of the facial forms. This can be seen in the details of the spectra discussed below, which show a marked red shift and broadening in the meridianal isomer relative to its facial counterpart. The emission lines appear as if a red band has been added to the band characteristic of the facial-L₃Ir. The structure of the meridianal isomer is similar to those of L₂IrX complexes, with respect, for example, to the arrangement of the N atoms of the ligands about Ir. Specifically, for L=ppy ligands, the nitrogen of the L ligand is trans in both mer-Ir(ppy)₃ and in (ppy)₂Ir(acac). Further, one of the L ligands for the mer-L₃Ir complexes has the same coordination as the X ligand of L₂IrX complexes. In order to illustrate this point a model of mer-Ir(ppy)₃ is shown next to (ppy)₂Ir(acac) in FIG. 14. One of the ppy ligands of mer-Ir(ppy)₃ is coordinated to the Ir center in the same geometry as the acac ligand of (ppy)₂Ir(acac).

Figure 13:
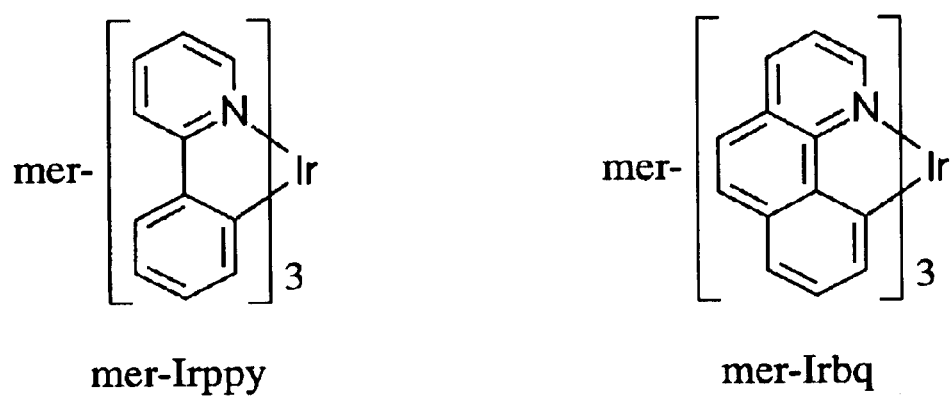
FIG. 13. Molecular formulae of mer- isomers disclosed herewith: mer-$Ir(ppy)_3$ and mer-$Ir(bq)_3$. PPY (or ppy) denotes phenyl pyridyl and BQ (or bq) denotes 7,8-benzoquinoline.

The HOMO and LUMO energies of these L₃Ir molecules are clearly affected by the choice of isomer. These energies are very important is controlling the current-voltage characteristics and lifetimes of OLEDs prepared with these phosphors. The syntheses for the two isomers depicted in FIG. 13 are as follows.

Syntheses of Meridianal Isomers mer-Irbq: 91 mg (0.078 mmol) of [Ir(bq)₂Cl]₂ dimer, 35.8 mg (0.2 mmol) of 7,8-benzoquinolin 0.02 ml of acetylacetone (ca. 0.2 mmol) and 83 mg (0.78 mmol) of sodium carbonate were boiled in 12 ml of 2-ethoxyethanol (used as received) for 14 hours in inert atmosphere. Upon cooling yellow-orange precipitate forms and is isolated by filtration and flash chromatography (silica gel, CH₂Cl₂) (yield 72%).

Figure 48:
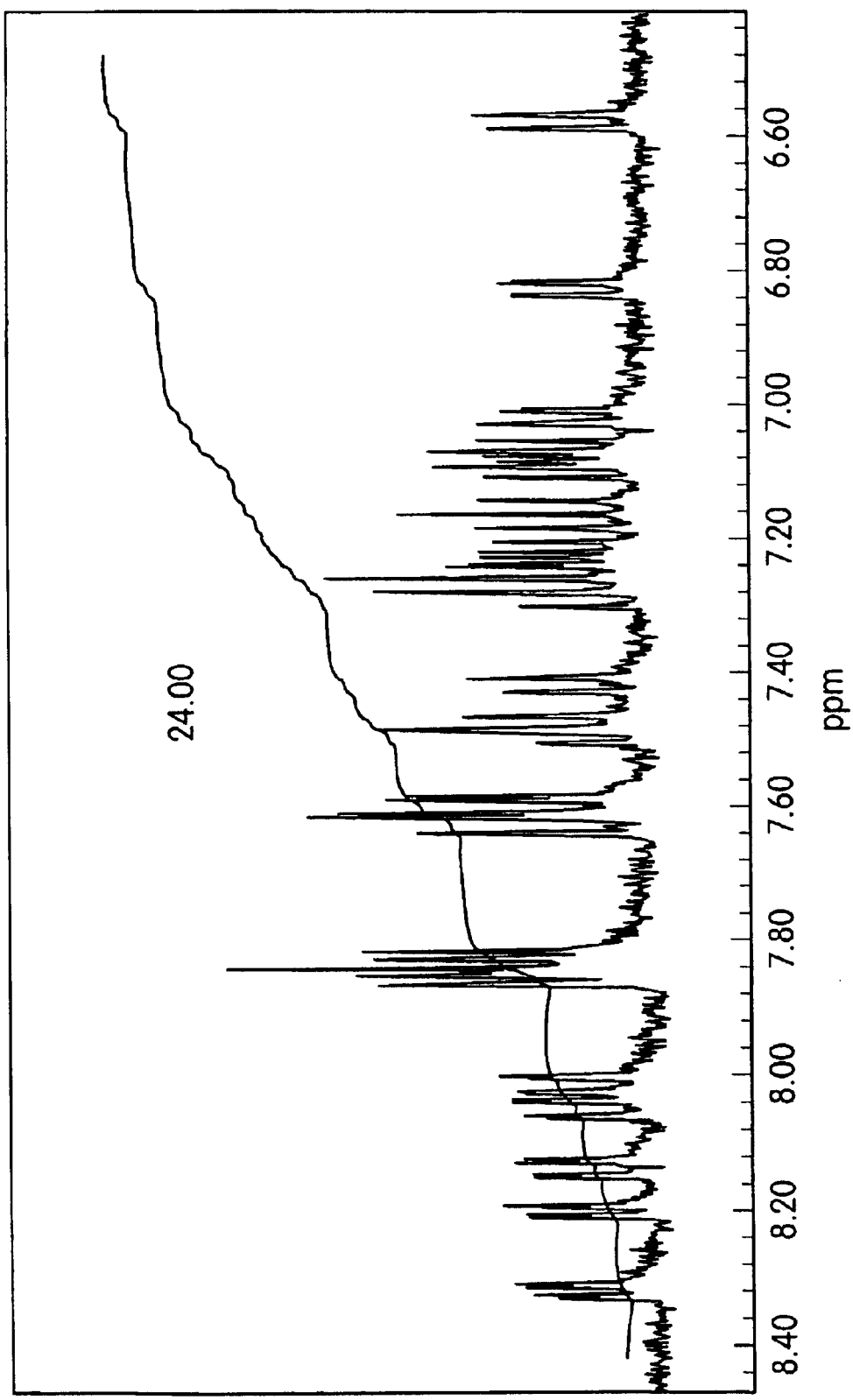
FIG. 48. Proton NMR spectrum of mer-Irbq.

1H NMR (360 MHz, dichloromethane-d2), ppm: 8.31 (q,1H), 8.18 (q,1H), 8.12 (q, 1H), 8.03(m,2H), 7.82 (m, 3H), 7.59 (m,2H), 7.47 (m,2H), 7.40 (d,1H), 7.17 (m,9), 6.81 (d,1H), 6.57 (d,1H). MS, e/z: 727 (100%, M+). NMR spectrum in FIG. 48.

mer-Ir(tpy)₃: A solution of IrCl₃.xH₂O (0.301 g, 1.01 mmol), 2-(p-tolyl)pyridine (1.027 g, 6.069 mmol), 2,4-pentanedione (0.208 g, 2.08 mmol) and Na₂CO₃ (0.350 g, 3.30 mmol) in 2-ethoxyethanol (30 mL) was refluxed for 65 hours. The yellow-green mixture was cooled to room temperature and 20 mL of 1.0 M HCl was added to precipitate the product. The mixture was filtered and washed with 100 mL of 1.0 M HCl followed by 50 mL of methanol then dried and the solid was dissolved in CH₂Cl₂ and filtered through a short plug of silica. The solvent was removed under reduced pressure to yield the product as a yellow-orange powder (0.265 g, 38%).

This invention is further directed toward the use of the above-noted dopants in a host phase. This host phase may be comprised of molecules comprising a carbazole moiety. Molecules which fall within the scope of the invention are included in the following.

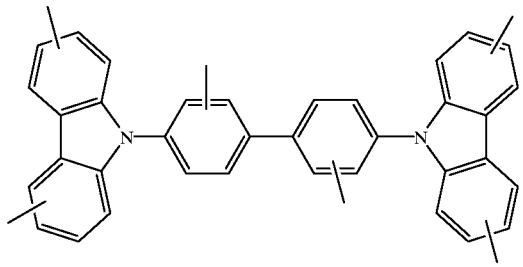

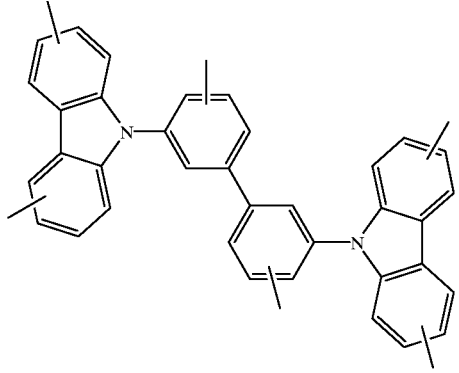

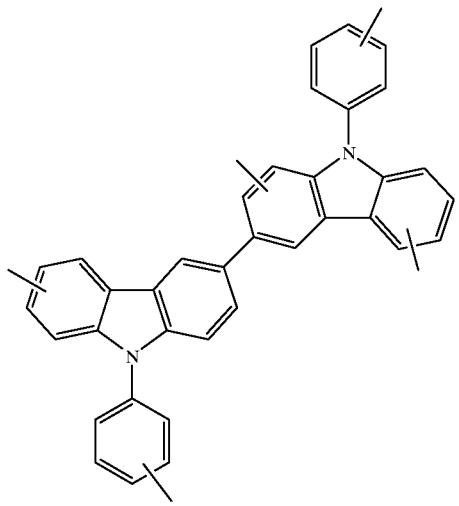

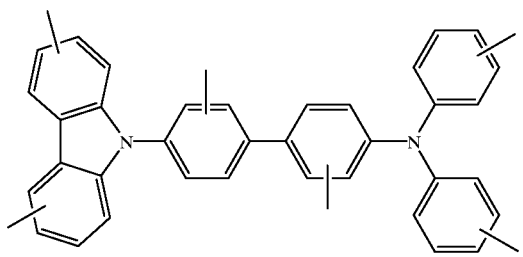

[A line segment denotes possible substitution at any available carbon atom or atoms of the indicated ring by alkyl or aryl groups.]

An additional preferred molecule with a carbazole functionality is 4,4'-N,N'-dicarbazole-biphenyl (CBP), which has the formula:

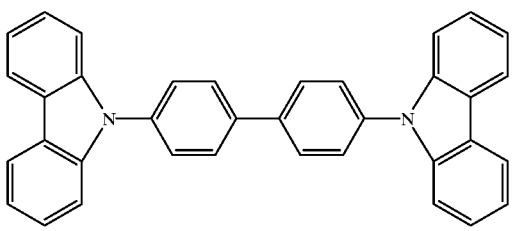

The light emitting device structure that we chose to use is very similar to the standard vacuum deposited one. As an overview, a hole transporting layer ("HTL") is first deposited onto the ITO (indium tin oxide) coated glass substrate. For the device yielding 12% quantum efficiency, the HTL consisted of 30 nm (300 Å) of NPD. Onto the NPD a thin film of the organometallic compound doped into a host matrix is deposited to form an emitter layer. In the example, the emitter layer was CBP with 12% by weight bis(2-phenylbenzothiazole) iridium acetylacetonate (termed "BTIr"), and the layer thickness was 30 nm (300 Å). A blocking layer is deposited onto the emitter layer. The blocking layer consisted of bathcuproine ("BCP"), and the thickness was 20 nm (200 Å). An electron transport layer is deposited onto the blocking layer. The electron transport layer consisted of Alq$_3$ of thickness 20 nm. The device is finished by depositing a Mg—Ag electrode onto the electron transporting layer. This was of thickness 100 nm. All of the depositions were carried out at a vacuum less than $5\times10^{-5}$ Torr. The devices were tested in air, without packaging.

When we apply a voltage between the cathode and the anode, holes are injected from ITO to NPD and transported by the NPD layer, while electrons are injected from MgAg to Alq and transported through Alq and BCP. Then holes and electrons are injected into EML and carrier recombination occurs in CBP, the excited states were formed, energy transfer to BTIr occurs, and finally BTIr molecules are excited and decay radiatively.

Figure 15A:
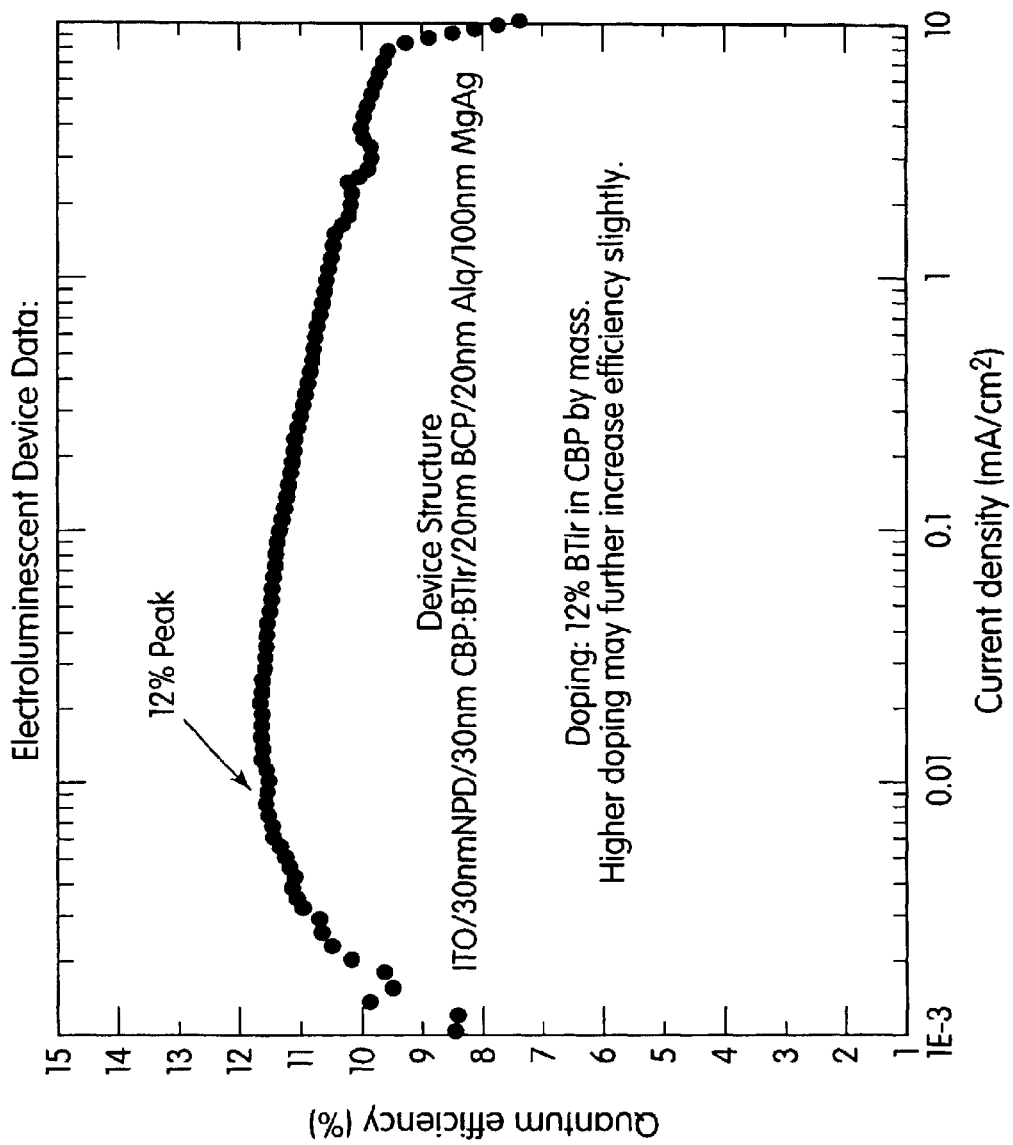
FIG. 15. (a) Electroluminescent device data (quantum efficiency vs. current density) for 12% by mass "BTIr" in CBP. BTIr stands for bis (2-phenylbenzothiazole) iridium acetylacetonate; (b) Emission spectrum from same device FIG. 16. Representative molecule to trap holes ($L_2IrX$ complex).
Figure 15B:
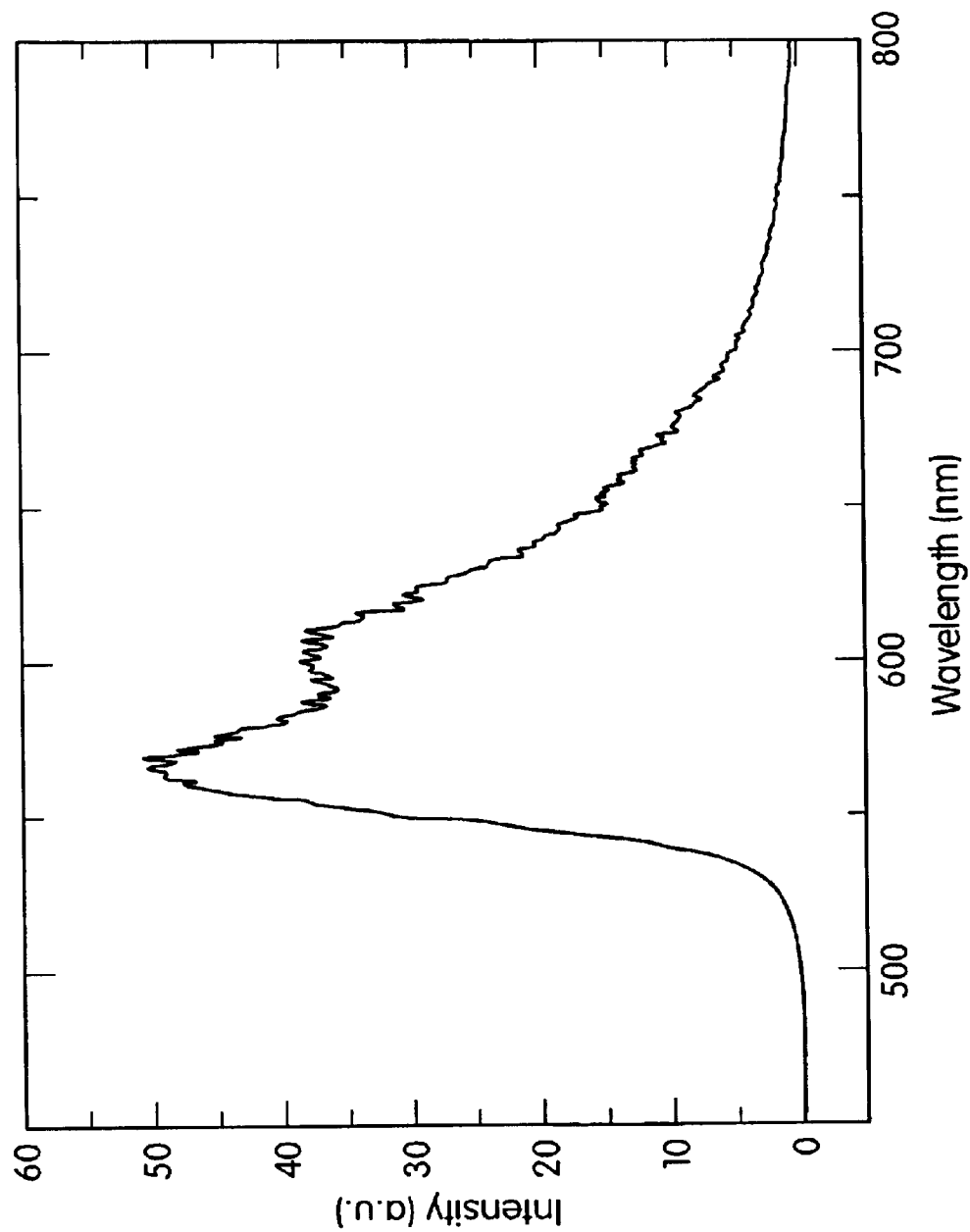

As illustrated in FIG. 15, the quantum efficiency of this device is 12% at a current density of about 0.01 mA/cm$^2$. Pertinent terms are as follows: ITO is a transparent conducting phase of indium tin oxide which functions as an anode; ITO is a degenerate semiconductor formed by doping a wide band semiconductor; the carrier concentration of the ITO is in excess of $10^9$/cm$^3$; BCP is an exciton blocking and electron transport layer; Alq$_3$ is an electron injection layer; other hole transport layer materials could be used, for example, TPD, a hole transport layer, can be used.

BCP functions as an electron transport layer and as an exciton blocking layer, which layer has a thickness of about 10 nm (100 Å). BCP is 2,9-dimethyl-4,7-diphenyl-1,10-phenanthroline (also called bathocuproine) which has the formula:

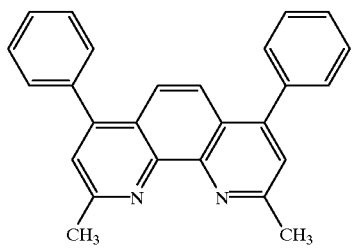

The Alq$_3$, which functions as an electron injection/electron transport layer has the following formula:

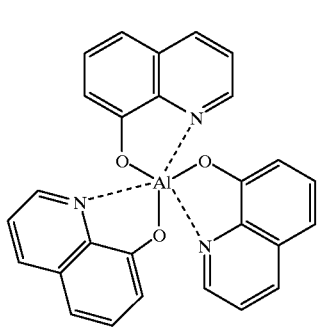

In general, the doping level is varied to establish the optimum doping level.

As noted above, fluorescent materials have certain advantages as emitters in devices. If the L ligand that is used in making the L$_2$MX (for example, M=Ir) complex has a high fluorescent quantum efficiency, it is possible to use the strong spin orbit coupling of the Ir metal to efficiently intersystem cross in and out of the triplet states of the ligands. The concept is that the Ir makes the L ligand an efficient phosphorescent center. Using this approach, it is possible to take any fluorescent dye and make an efficient phosphorescent molecule from it (that is, L fluorescent but L$_2$MX (M=Ir) phosphorescent).

As an example, we prepared a L$_2$IrX wherein L=coumarin and X=acac. We refer to this as coumarin-6 ["C6Ir"]. The complex gives intense orange emission, whereas coumarin by itself emits green. Both coumarin and C6Ir spectra are given in the Figures.

Other fluorescent dyes would be expected to show similar spectral shifts. Since the number of fluorescent dyes that have been developed for dye lasers and other applications is quite large, we expect that this approach would lead to a wide range of phosphorescent materials.

One needs a fluorescent dye with suitable functionality such that it can be metallated by the metal (for example, iridium) to make a 5- or 6-membered metallocycle. All of the L ligands we have studied to date have sp$^2$ hybridized carbons and heterocyclic N atoms in the ligands, such that one can form a five membered ring on reacting with Ir.

Potential degradation reactions, involving holes or electrons, can occur in the emitter layer. The resultant oxidation or reduction can alter the emitter, and degrade performance. In order to get the maximum efficiency for phosphor doped OLEDs, it is important to control the holes or electrons which lead to undesirable oxidation or reduction reactions. One way to do this is to trap carriers (holes or electrons) at the phosphorescent dopant. It may be beneficial to trap the carrier at a position remote from the atoms or ligands responsible for the phosphorescence. The carrier that is thus remotely trapped could readily recombine with the opposite carrier either intramolecularly or with the carrier from an adjacent molecule.

Figure 16:
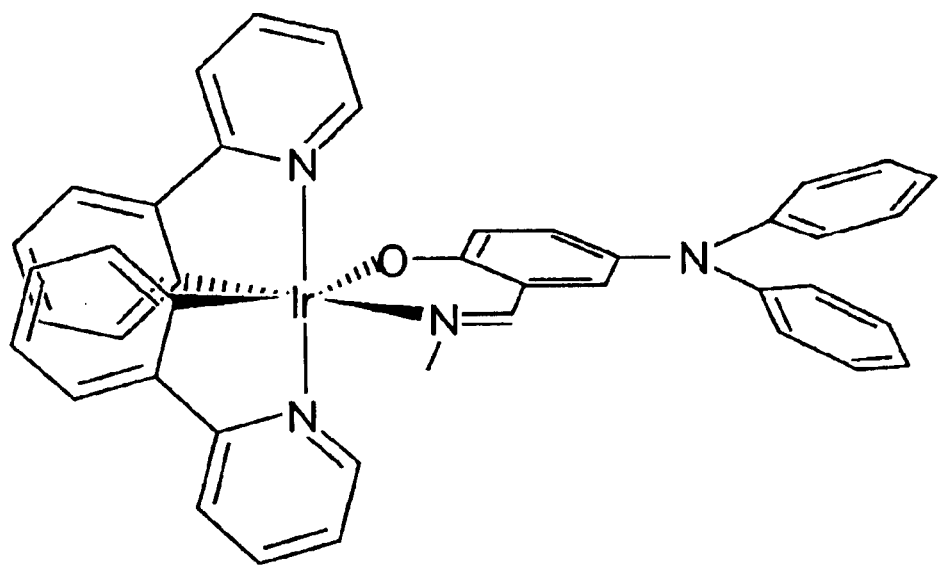

An example of a phosphor designed to trap holes is shown in FIG. 16. The diarylamine group on the salicylanlide group is expected to have a HOMO level 200–300 mV above that of the Ir complex (based on electrochemical measurements), leading to the holes being trapped exclusively at the amine groups. Holes will be readily trapped at the amine, but the emission from this molecule will come from MLCT and intraligand transitions from the Ir(phenylpyridine) system. An electron trapped on this molecule will most likely be in one of the pyridyl ligands. Intramolecular recombination will lead to the formation of an exciton, largely in the Ir(phenylpyridine) system. Since the trapping site is on the X ligand, which is typically not involved extensively in the luminescent process, the presence of the trapping site will not greatly affect the emission energy for the complex. Related molecules can be designed in which electron carriers are trapped remoted to the $L_2Ir$ system.

As found in the $IrL_3$ system, the emission color is strongly affected by the L ligand. This is consistent with the emission involving either MLCT or intraligand transitions. In all of the cases that we have been able to make both the tris complex (i.e., $IrL_3$ ) and the $L_2IrX$ complex, the emission spectra are very similar. For example $Ir(ppy)_3$ and $(ppy)_2Ir$ (acac) (acronym=PPIr) give strong green emission with a $\lambda_{max}$ of 510 nm. A similar trend is seen in comparing $Ir(BQ)_3$ and $Ir(thpy)_3$ to their $L_2Ir(acac)$ derivatives, i.e., in some cases, no significant shift in emission between the two complexes.

However, in other cases, the choice of X ligand affects both the energy of emission and efficiency. Acac and salicylanilide $L_2IrX$ complexes give very similar spectra. The picolinic acid derivatives that we have prepared thus far show a small blue shift (15 nm) in their emission spectra relative to the acac and salicylanilide complexes of the same ligands. This can be seen in the spectra for BTIr, BTIrsd and BTIrpic. In all three of these complexes we expect that the emission becomes principally form MLCT and Intra-L transitions and the picolinic acid ligands are changing the energies of the metal orbitals and thus affecting the MLCT bands.

If an X ligand is used whose triplet levels fall lower in energy than the "$L_2Ir$" framework, emission from the X ligand can be observed. This is the case for the BTIRQ complex. In this complex the emission intensity is very weak and centered at 650 nm. This was surprising since the emission for the BT ligand based systems are all near 550 nm. The emission in this case is almost completely from Q based transitions. The phosphorescence spectra for heavy metal quinolates (e.g., $IrQ_3$ or $PtQ_2$) are centered at 650 nm. The complexes themselves emit with very low efficiency, <0.01. Both the energy and efficiency of the $L_2IrQ$ material is consistent "X" based emission. If the emission from the X ligand or the "IrX" system were efficient this could have been a good red emitter. It is important to note that while all of the examples listed here are strong "L" emitters, this does not preclude a good phosphor from being formed from "X" based emission.

The wrong choice of X ligand can also severely quench the emission from $L_2IrX$ complexes. Both hexafluoro-acac and diphenyl-acac complexes give either very weak emission of no emission at all when used as the X ligand in $L_2IrX$ complexes. The reasons why these ligands quench emission so strong are not at all clear, one of these ligands is more electron withdrawing than acac and the other more electron donating. We give the spectrum for BQIrFA in the Figures.

The emission spectrum for this complex is slightly shifted from BQIr, as expected for the much stronger electron withdrawing nature of the hexafluoroacac ligand. The emission intensity from BQIrFA is at least 2 orders of magnitude weaker than BQIr. We have not explored the complexes of these ligands due to this severe quenching problem.

CBP was used in the device described herein. The invention will work with other hole-transporting molecules known by one of ordinary skill to work in hole transporting layers of OLEDs. Specifically, the invention will work with other molecules comprising a carbazole functionality, or an analogous aryl amine functionality.

The OLED of the present invention may be used in substantially any type of device which is comprised of an OLED, for example, in OLEDs that are incorporated into a larger display, a vehicle, a computer, a television, a printer, a large area wall, theater or stadium screen, a billboard or a sign.

What is claimed is:

1. An organic light emitting device comprising an anode, a cathode and an emissive layer, wherein the emissive layer is located between the anode and the cathode and the emissive layer comprises a phosphorescent organometallic compound, wherein the phosphorescent organometallic compound is an iridium compound including a carbon-metal bond.

2. The organic light emitting device of claim 1, wherein the iridium compound includes a cyclometallated ring having a carbon-metal bond.

3. The organic light emitting device of claim 1, wherein the iridium compound is fac-tris(2-phenylpyridine) iridium, as denoted by the formula:

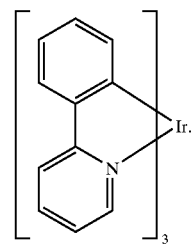

4. The organic light emitting device of claim 1, wherein the phosphorescent organometallic compound is a cyclometallated compound including a cycle closed with at least one metal-X bond, wherein X is selected from the group consisting of nitrogen, sulfur, phosphorous, arsenic and oxygen, and including a cycle closed with at least one carbon-metal bond.

5. The organic light emitting device of claim 4, wherein X is nitrogen.

6. The organic light emitting device of claim 1, wherein the iridium compound is denoted by the formula:

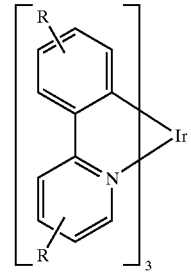

wherein R is an alkyl or aryl group.

7. The organic light emitting device of claim 6, wherein the R group an alkyl group.

8. The organic light emitting device of claim 6, wherein the R group is an aryl group.

9. An organic light emitting device comprising an anode, a cathode and an emissive layer, wherein the emissive layer is located between the anode and the cathode, and the emissive layer comprises a host material and a phosphorescent organometallic compound present as a dopant in said host material, wherein the phosphorescent organometallic compound includes a carbon-metal bond and is selected from the group consisting of osmium compounds including a cyclometallated ring having a carbon-metal bond, iridium compounds and platinum compounds.

10. The organic light emitting device of claim 9, wherein the phosphorescent organometallic compound is an iridium compound.

11. The organic light emitting device of claim 10, wherein the iridium compound includes a cyclometallated ring having a carbon-metal bond.

12. The organic light emitting device of claim 10, wherein the iridium compound is fac-tris(2-phenylpyridine) iridium, as denoted by the formula:

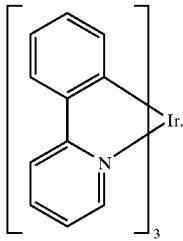

13. The organic light emitting device of claim 10, wherein the iridium compound is denoted by the formula:

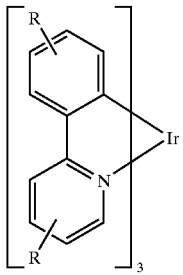

wherein R is an alkyl or aryl group.

14. The organic light emitting device of claim 13, wherein the R group is an alkyl group.

15. The organic light emitting device of claim 13, wherein the R group is an aryl group.

16. The organic light emitting device of claim 9, wherein the phosphorescent organometallic compound is a cyclometallated osmium compound.

17. The organic light emitting device of claim 9, wherein the phosphorescent organometallic compound is a platinum compound.

18. The organic light emitting device of claim 9, wherein the phosphorescent organometallic compound is a cyclometallated compound including a cycle closed with at least one metal-X bond, wherein X is selected from the group consisting of nitrogen, sulfur, phosphorous, arsenic and oxygen, and including a cycle closed with at least one carbon-metal bond.

19. The organic light emitting device of claim 18, wherein the phosphorescent organometallic compound is a cyclometallated platinum compound.

20. The organic light emitting device of claim 18, wherein X is nitrogen.

21. The organic light emitting device of claim 9, wherein the host material is a polymeric host material.

22. The organic light emitting device of claim 21, wherein the polymeric host material is a polyvinylcarbazole.

23. The organic light emitting device of claim 9, wherein the phosphorescent organometallic compound is substituted with an electron donor group.

24. The organic light emitting device of claim 9, wherein the phosphorescent organometallic compound is substituted with an electron acceptor group.

25. An organic light emitting device comprising an anode, a cathode and an emissive layer, wherein the emissive layer is located between the anode and the cathode and the emissive layer comprises a phosphorescent organometallic compound, wherein the phosphorescent organometallic compound is a cyclometallated compound including a cyclometallated ring having a carbon-metal bond.

26. The organic light emitting device of claim 25, wherein the cyclometallated compound is a platinum compound.

27. The organic light emitting device of claim 25, wherein the cyclometallated compound further includes a cycle closed with at least one metal-X bond, wherein X is selected from the group consisting of nitrogen, sulfur, phosphorous, arsenic and oxygen.

28. The organic light emitting device of claim 27, wherein the cyclometallated compound is a platinum compound.

29. The organic light emitting device of claim 27, wherein X is nitrogen.

* * * * *